US012709613B2

(12) United States Patent
Han et al.

(10) Patent No.: US 12,709,613 B2
(45) Date of Patent: Aug. 18, 2026

(54) NAPHTHYRIDINONE DERIVATIVE HAVING INHIBITORY ACTIVITY AGAINST ECTONUCLEOTIDE PYROPHOSPHATASE-PHOSPHODIESTERASE AND USE THEREOF

(71) Applicant: TXINNO BIOSCIENCE INC., Gyeonggi-Do (KR)

(72) Inventors: Seo Jung Han, Seoul (KR); Chan Sun Park, Gyeonggi-Do (KR); Sung Joon Kim, Gyeonggi-Do (KR); Jae Eun Cheong, Seoul (KR); Jung Hwan Choi, Gyeonggi-Do (KR); Ali Imran, Gyeonggi-Do (KR); Sun Woo Lee, Gyeonggi-Do (KR); Yong Yea Park, Gyeonggi-Do (KR); Ah Ran Yu, Gyeonggi-Do (KR); Sun Young Park, Gyeonggi-Do (KR)

(73) Assignee: TXINNO BIOSCIENCE INC., Gyeonggi-Do (KR)

( * ) Notice: Subject to any disclaimer, the term of this patent is extended or adjusted under 35 U.S.C. 154(b) by 360 days.

(21) Appl. No.: 18/269,609

(22) PCT Filed: Dec. 29, 2021

(86) PCT No.: PCT/KR2021/020143

§ 371 (c)(1),
(2) Date: Jun. 26, 2023

(87) PCT Pub. No.: WO2022/146022

PCT Pub. Date: Jul. 7, 2022

(65) Prior Publication Data

US 2024/0140944 A1 May 2, 2024

(30) Foreign Application Priority Data

Dec. 29, 2020 (KR) ........................ 10-2020-0185961
Dec. 28, 2021 (KR) ........................ 10-2021-0189895

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 2010/0197924 | A1 | 8/2010 | Gould et al. | |
| 2011/0118470 | A1 | 5/2011 | Funahashi et al. | |
| 2011/0269758 | A1* | 11/2011 | Xiao | A61P 1/16 514/264.11 |
| 2020/0039979 | A1 | 2/2020 | Vankayalapati | |

FOREIGN PATENT DOCUMENTS

| | | | |
|---|---|---|---|
| CN | 102083831 | A | 6/2011 |
| CN | 105061421 | A | 11/2015 |
| CN | 110575458 | A | 12/2019 |
| JP | 2006-517976 | A | 8/2006 |
| JP | 2009-519908 | A | 5/2009 |
| JP | 2011-526912 | A | 10/2011 |
| JP | 2015-506353 | A | 3/2015 |
| JP | 2020-15670 | A | 1/2020 |
| JP | 2020-532526 | A | 11/2020 |
| KR | 10-2011-0025856 | A | 3/2011 |
| RU | 2264389 | C2 | 11/2005 |
| WO | 2002/032872 | A1 | 4/2002 |
| WO | 2004/073628 | A2 | 9/2004 |
| WO | 2007/067444 | A1 | 6/2007 |
| WO | 2010/002779 | A2 | 1/2010 |
| WO | 2010/090716 | A1 | 8/2010 |
| WO | 2014/206343 | A1 | 12/2014 |
| WO | 2016/038389 | A1 | 3/2016 |
| WO | 2017146246 | A1 | 8/2017 |
| WO | 2018/119325 | A1 | 6/2018 |
| WO | 2018/119328 | A1 | 6/2018 |
| WO | 2019/018583 | A1 | 1/2019 |
| WO | 2019/023635 | A1 | 1/2019 |
| WO | 2019/046778 | A1 | 3/2019 |
| WO | 2019/051269 | A1 | 3/2019 |
| WO | 2019/177971 | A1 | 9/2019 |
| WO | 2019/200120 | A1 | 10/2019 |
| WO | 2019/233300 | A1 | 12/2019 |
| WO | 202012357 | A1 | 1/2020 |
| WO | 2020/151756 | A1 | 7/2020 |
| WO | 2020/188049 | A1 | 9/2020 |
| WO | 2021/043245 | A1 | 3/2021 |
| WO | 2022146022 | A1 | 7/2022 |

OTHER PUBLICATIONS

6. CAS RN 1203509-61-8 (entered into STN on Jan. 25, 2010) (Year: 2010).*
International Search Report issued in PCT/KR2021/020143, mailed Apr. 11, 2022.
Knuyants, Chemical Encyclopedia Dictionary (1983), pp. 1, 130-131.
Healy A.M. et al., "Pharmaceutical solvates, hydrates and amorphous forms: A special emphasis on cocrystals" Advanced Drug Delivery Review 117(2017) pp. 25-46.

(Continued)

*Primary Examiner* — Craig D Ricci

(74) *Attorney, Agent, or Firm* — Troutman Pepper Locke LLP; Scott D. Wofsy

(57) ABSTRACT

The present invention relates to a novel naphthyridinone derivative compound, a pharmaceutically acceptable salt thereof, a hydrate thereof, or a stereoisomer thereof, which are each relevant to a compound for inhibiting ENPP1, a composition for inhibiting ENPP1, and a method for inhibiting ENPP1.

7 Claims, No Drawings

(56) References Cited

OTHER PUBLICATIONS

Belikov, Farmatsevticheskaya Khimiya (Pharmaceutical Chemistry), fourth edition (2007), pp. 27-29.

Pier Luigi Ferrarini et al. , "Synthesis of 1,8-naphthyridine derivatives: potential antihypertensive agents—Part VIII", Eur. J. Med. Chem., 34/6, p. 505-513, Jun. 1, 1999 (Jan. 6, 1999).

CAS Registry for 5-[[(1R, 1aR,6bR)-1-amino-1a,6b-dihydro-1H-cyclopropa[b]benzofuran-5-yl]oxy] -3,4-dihydro-1,8-naphthyridin-2(1H)-one.

* cited by examiner

NAPHTHYRIDINONE DERIVATIVE HAVING INHIBITORY ACTIVITY AGAINST ECTONUCLEOTIDE PYROPHOSPHATASE-PHOSPHODIESTERASE AND USE THEREOF

CROSS-REFERENCE TO RELATED APPLICATIONS

This application is a U.S. National Phase Application filed under 35 U.S.C. § 371, based on International PCT Patent Application No. PCT/KR2021/020143, filed Dec. 29, 2021, which claims priority to Korean Patent Application No. 10-2021-0189895, filed on Dec. 28, 2021 and Korean Patent Application No. 10-2020-0185961, filed on Dec. 29, 2020. The entire contents of these applications is incorporated herein by reference.

TECHNICAL FIELD

The present invention relates to a compound selected from a novel naphthyridinone derivative compound having inhibitory activity against ectonucleotide pyrophosphatase-phosphodiesterase (ENPP), a pharmaceutically acceptable salt thereof, a hydrate thereof and a stereoisomer thereof, a method for preparing the compound, and a pharmaceutical composition for preventing, alleviating or treating cancer containing the compound.

BACKGROUND ART

Disclosure

Cancer is a disease associated with uncontrolled cell proliferation that invades or proliferates to other organs, thus reducing quality of life and eventually leading to death. Although genetic aberrations are a direct cause of uncontrolled proliferation of cancer cells, failure of immune surveillance and/or lack of an adequate immune counterattack of the immune system against cancer cells is another cause of cancer cell proliferation. Also, this leads to the formation of primary tumors having a tumor microenvironment (TME) with suppressed anticancer immunity. Then, cancer cells pass through a locally advanced cancer stage and eventually develop into metastatic cancer that penetrates other organs, causing decrease in the cure rate and survival rate of cancer patients. Therapeutic agents for treating such fatal diseases may be broadly divided into two categories. The first category directly targets the cancer cells, and the second category targets the components of the tumor microenvironment (TME) to prevent further proliferation or survival of cancer cells.

Cancer immunotherapy is a therapeutic approach that targets immune factors present in the TME to cause immune cells to attack tumor cells. In some cases, cancer immunotherapy aims to promote recognition of tumor cells through the release of tumor-associated antigens in the TME (e.g., cancer vaccines). In other cases, cancer immunotherapy aims to promote attack on tumor cells by regulating the activity of innate and/or adaptive immune cells (e.g., immune checkpoint blockade). In other cases, cancer immunotherapy aims to induce tumor death by manipulating patient-derived lymphocytes ex vivo to express chimeric antigen receptors, recognize antigens on the tumor surface and enhance the activity of lymphocytes (e.g., chimeric antigen receptor T cell therapy (CAR-T Cell therapy)).

Microbial infections cause a variety of diseases all over the world. Pathogenic microorganisms are diverse and include viruses, bacteria, fungi and protozoa. In some cases, a therapeutic agent is a chemical that directly prevents microbial growth. In other cases, therapeutic agents are therapeutic substances for enhancing or stimulating host immune function against pathogenic microorganisms.

The tumor microenvironment (TME) contains malignant tumor cells as well as various types of immune cells (e.g., macrophages, lymphocytes, NK cells and dendritic cells) and non-immune cells (e.g., cancer-associated fibroblasts, pericytes, endothelial cells, and adipocytes). Meanwhile, the presence of tumor-infiltrating lymphocytes has been reported to cause positive clinical outcomes in response to multiple pipelines of immunotherapy in different types of cancer. Preclinical studies reported that modulation or upregulation of other types of immune cells other than lymphocytes, particularly innate immune cells, modulates the responsiveness of anticancer therapies to tumors. The innate immune system is one of the two major components of the host immune defense system in vertebrates. The main functions of innate immunity include 1) to identify and remove foreign substances (e.g., bacteria, viruses) from body tissues, 2) to recruit immune cells to specific sites by producing cytokines and promoting adaptive immune responses, and 3) to activate the complement cascade. Such innate immunity may be activated by recognizing molecular patterns derived from microbial pathogens (pathogen-associated molecular patterns, PAMPs) or residues of destroyed cells (damage-associated molecular patterns, DAMPs).

Pattern recognition receptors (PRRs) are several different types of receptors that are mainly expressed by innate immune cells and can recognize specific PAMPs or DAMPs depending on the ligand specificity thereof. Cytoplasmic DNA is a type of molecular pattern recognized by cytoplasmic DNA sensors (a type of PRR) and triggers an innate immune response. The cGAS-STING pathway (cGAS, cyclic GMP-AMP synthase; STING, stimulator of interferon genes), which is a type of cytoplasmic DNA sensor, is involved in 1) cytoplasmic DNA recognition resulting from microbial infection or self-DNA damage and 2) type 1 interferons (IFNs) by generation of chemical factors, mainly activation of the IRE3 transcription factor.

Type 1 IFN produced by TME due to transformed cancer cells promotes recruitment and activation of inflammatory cells, including NK cells, at the tumor site, and induces both tumor cell death and production of chemoattractants that promote adaptive immune responses.

Systemic administration of type 1 IFN showed verified efficacy in cancer environments based on tumor regression and improved survival rate by systemic injection of IFN-beta in a preclinical mouse model. However, systemic administration of type 1 IFN has a problem in that a high dose is required to reach a therapeutically effective amount to obtain therapeutic efficacy. In this case, tolerance issues were reported.

Recently published clinical outcomes of exogenous STING agonists (modified cyclic dinucleotides) have shown lower disease control rates than expected despite an apparent increase in pro-inflammatory cytokine production.

Therefore, there is a need for research on novel therapeutic methods that can activate the cGAS-STING pathway.

PRIOR ART LITERATURE

Patent Literature

Chinese Patent Publication No. CN 110575458 A
International Publication No. WO 2019/233300 A1

International Publication No. WO 2018/119325 A1
International Publication No. WO 2018/119328 A1
International Publication No. WO 2019/046778 A1
International Publication No. WO 2019/177971 A1
Japanese Patent Publication No. JP 2020-15670
International Publication No. WO 2019/051269 A1
US Patent Publication No. US 2020/0039979 A1
International Publication No. WO 2019/023635 A1
International Publication No. WO 2019/051269 A1

Disclosure

Technical Problem

In order to solve the above problems, the present invention provides a method for increasing the activity of a cGAS-STING pathway.

It is one object of the present invention to provide a novel naphthyridinone derivative compound having inhibitory activity against ENPP1. It is another aspect of the present invention to provide a novel naphthyridinone derivative compound for improving and/or modulating the production of type 1 interferons (IFNs) in vivo.

It is another object of the present invention to provide a pharmaceutical composition useful for the treatment, prevention and alleviation of cancer containing, as an active ingredient, a novel naphthyridinone derivative compound, a pharmaceutically acceptable salt thereof, a hydrate thereof, a solvate thereof or a stereoisomer thereof.

It is another object of the present invention to provide a method for preventing, alleviating or treating cancer including administering the novel naphthyridinone derivative compound or the pharmaceutical composition containing the same to a patient or subject in need thereof.

It is another object of the present invention to provide a method for preventing, alleviating or treating an infectious disease including administering the novel naphthyridinone derivative compound or the pharmaceutical composition containing the same to a patient or subject in need thereof.

It is another object of the present invention to provide a method for preventing, alleviating or treating periodontal disease including administering the novel naphthyridinone derivative compound or the pharmaceutical composition containing the same to a patient or subject in need thereof.

It is another object of the present invention to provide a method for preventing, alleviating or treating pathological mineralization of soft tissue including administering the novel naphthyridinone derivative compound or the pharmaceutical composition containing the same to a patient or subject in need thereof.

It is another object of the present invention to implement the following mechanism with an active ingredient of a novel naphthyridinone derivative compound, a pharmaceutically acceptable salt thereof, a hydrate thereof, a solvate thereof, or an isomer thereof. In one aspect, the method includes priming cancer with an agent for inducing immunogenic cell death (ICD) prior to stimulation of the cGAS-STING pathway. In another aspect, the method includes blocking degradation of an endogenous STING ligand prior to priming the cancer with the agent for inducing ICD. In another aspect, the method includes the use of an inhibitor for 2',3'-cGAMP degrading polypeptide in combination with the agent for inducing ICD for the treatment of cancer. In one aspect, the present invention provides a method for designing an inhibitor for 2',3'-cGAMP-degrading polypeptide and a detailed assay method for evaluating the enzymatic activity of cGAMP-degrading polypeptide.

Technical Solution

In order to solve the technical problems described above, in one aspect, the present invention provides a compound selected from a naphthyridinone derivative compound represented by the following Formula 1, a pharmaceutically acceptable salt thereof, a hydrate thereof, a solvate thereof and a stereoisomer thereof:

[Formula 1]

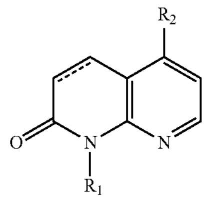

wherein $R_1$ is hydrogen, a $C_1$-$C_{13}$ alkyl group, or a $C_3$-$C_{10}$ cyclic group;

$R_2$ is —Z—$R_3$—$(R_4)_m$;

Z is present or absent, wherein when Z is present, Z is —O—, —CO—, —COO—, —$C_nH_{n+2}$, —O($C_nH_{n+2}$)—, —$(OC_2H_4)_n$—, —$(C_2H_4O)_n$—, —($C_nH_{n+2}$)O—, —($C_nH_{n+2}$)CO—, —($C_nH_{n+2}$)O($C_mH_{m+2}$)—, —$NR_6$($C_nH_{n+2}$)—, —$(NR_6C_2H_4)_n$—, —$(C_2H_4NR_6)_n$—, or —($C_nH_{n+2}$)$NR_6$—;

n is an integer from 0 to 8;

$R_3$ is a $C_3$-$C_{10}$ cyclic group, a $C_3$-$C_{10}$ heterocyclic group, a $C_6$-$C_{10}$ aryl group, or a $C_3$-$C_{10}$ heteroaryl group;

$R_4$ is hydrogen, a hydroxyl group, a halogen group, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclic group, a $C_3$-$C_{10}$ heteroaryl group, a $C_3$-$C_{10}$ heterocyclic group, —C(O)—($C_1$-$C_{13}$ alkyl), a tert-butyloxycarbonyl group (Boc), an amino group (—$NR_5R_6$), —($C_mH_{m+2}$)$NR_5R_6$, a nitro group (—$N(O)_2$), an amide group (—(C═O)$NR_5R_6$), an ester group (—C(O)$OR_6$), a carboxylic group (—C(O)OH), a nitrile group (—CN), a sulfonamide group (—$NHS(O)_2R_6$), a urea group, a sulfamoyl group (—$NHS(O)_2NHR_6$), a sulfonamide group, a sulfamoylalkyl group (—($C_mH_{m+2}$)$NHS(O)_2NHR_6$), a sulfamoylalkyl group (—($C_mH_{m+2}$)$NR_5S(O)_2NHR_6$), a sulfide group (—$SR_6$), a sulfone group (—$S(O)_2R_6$), or a phosphoryl group (—P(O)$R_5R_6$), or is bonded to the same carbon as the carbon bonded to $R_3$ to form a 3- to 7-membered saturated ring, is bonded to the same carbon as the carbon bonded to $R_3$ to form a 3- to 7-membered saturated heterocycle containing at least one heteroatom of N, O and S, is bonded to the carbon adjacent to the carbon bonded to $R_3$ to form a 3- to 7-membered saturated ring, or is bonded to the carbon adjacent to the carbon bonded to $R_3$ to form a 3- to 7-membered saturated heterocycle containing at least one heteroatom of N, O and S;

m is an integer from 1 to 4;

wherein the $C_1$-$C_6$ alkyl group, the $C_1$-$C_{13}$ alkyl group or the $C_3$-$C_{10}$ cyclic group includes at least one substituent selected from the group consisting of hydrogen, a hydroxyl group, a halogen group, a $C_1$-$C_{13}$ alkyl group, a $C_1$-$C_6$ alkoxy group, an amino group (—$NR_5R_6$), a nitro group (—$N(O)_2$), an amide group (—(C═O) $NR_5R_6$), a carboxylic group (—C(O)OH), a nitrile group (—CN), a urea group (—$NR_5$(C═O)$NR_6$—), a sulfonamide group (—$NHS(O)_2$—), a sulfide group (—S—), a sulfonyl group (—$S(O)_2$—), a phosphoryl group (—P(O) $R_5R_6$), a $C_6$-$C_{10}$ aryl group, a $C_3$-$C_{10}$ heteroaryl group, and a $C_3$-$C_{10}$ heterocyclic group, and the $C_6$-$C_{10}$ aryl group, the $C_3$-$C_{10}$ heteroaryl group or the $C_3$-$C_{10}$ heterocyclic group includes at least one substituent selected from the group consisting of hydrogen, a hydroxyl group, a halogen group, a carbonyl group (—(C═O)$R_5R_6$), a $C_1$-$C_3$ alkyl group substituted or unsubstituted with halogen or a $C_3$-$C_{10}$ heterocyclic group, a $C_1$-$C_3$ alkoxy group substituted or unsubstituted with halogen or a $C_3$-$C_{10}$ heterocyclic group, $C_6$-$C_{10}$ phenoxy, an amino group (—$NR_5R_6$), a nitro group (—$N(O)_2$), an amide group (—(C═O) $NR_5R_6$), a carboxylic group (—C(O)OH), a nitrile group (—CN), a urea group (—$NR_5$(C═O)$NR_6$—), a sulfonamide group (—$NHS(O)_2$—), a sulfide group (—S—), a sulfonyl group (—$S(O)_2$—), a phosphoryl group (—P(O)$R_5R_6$), a $C_6$-$C_{10}$ aryl group, a $C_3$-$C_{10}$ heteroaryl group and a $C_3$-$C_{10}$ heterocyclic group; and $R_5$ and $R_6$ are each independently hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, a $C_3$-$C_{10}$ heterocyclic group, or $R_5$, together with a nitrogen or carbon atom bonded to $R_6$, forms a 3- to 7-membered saturated ring, which includes at least one of N, O, S, NH, C═N, C═O, —NHC(O)—, —NHC(O)NH—, —$NHS(O)_2$—, or $SO_2$, and is substituted with at least one of hydrogen, a $C_1$-$C_{13}$ alkyl group, a $C_6$-$C_{10}$ aryl group, a $C_3$-$C_{10}$ heteroaryl group, a hydroxyl group, a halide group or a cyano group, wherein the $C_3$-$C_{10}$ heteroaryl group and the $C_3$-$C_{10}$ heterocyclic group include at least one heteroatom selected from the group consisting of N, O, and S.

Advantageous Effects

The compound according to the present invention is capable of effectively inhibiting the activity of ENPP1. Therefore, the compound may be used for the treatment, prevention and alleviation of cancer diseases caused by abnormal cell growth.

The compound according to the present invention, the pharmaceutically acceptable salt or the hydrate thereof, and the pharmaceutical composition for preventing or treating cancer containing the same as an active ingredient effectively inhibit ENPP1 to activate the STING pathway and are thus useful for the prevention or treatment of cancer and prevention of cancer metastasis.

Cancer diseases that can be treated, prevented and alleviated by the administration of the compound according to the present invention include gastric cancer, lung cancer, liver cancer, colorectal cancer, small intestine cancer, pancreatic cancer, brain cancer, bone cancer, melanoma, breast cancer, scleroderma, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, and myelodysplastic syndrome), lymphoma (including Hodgkin's disease and non-Hodgkin's lymphoma), psoriasis, fibroadenoma, and the like.

In particular, the compound according to the present invention is effective in preventing, alleviating or treating diseases involving ENPP 1.

BEST MODE

Definitions

Unless the context clearly indicates otherwise, all numbers, figures and/or expressions that represent ingredients, reaction conditions, polymer compositions, and amounts of mixtures used in the specification are approximations that reflect various uncertainties of measurement occurring inherently in obtaining these figures, among other things. For this reason, it should be understood that, in all cases, the term "about" should be understood to modify all numbers, figures, and/or expressions. In addition, when numerical ranges are disclosed in the description, these ranges are continuous and include all numbers from the minimum to the maximum, including the maximum within each range, unless otherwise defined. Furthermore, when the range refers to an integer, it includes all integers from the minimum to the maximum, including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5, and 6.5 to 9, between appropriate integers that fall within the range. In addition, for example, the range of "10% to 30%" encompasses all integers, including numbers such as 10%, 11%, 12% and 13% as well as 30%, and any sub-ranges, such as ranges of 10% to 15%, 12% to 18%, or 20% to 30%, as well as any numbers, such as 10.5%, 15.5% and 25.5%, between appropriate integers that fall within the range.

As used herein, the terms "individual(s)," "subject(s)," and "patient(s)" mean any mammal(s). In some embodiments, the mammal is a human. In some embodiments, the mammal is not a human. Any one of the terms does not require the situation characterized by the supervision (e.g., permanent or intermittent) of health care workers (e.g., physicians, regular nurses, apprentice nurses, physician's assistants, handymen or hospice workers) or is not limited to the situation.

The term "treatment" is an attempt intended to prevent the development or alteration of a lesion of a disease. Accordingly, the term "treatment" refers to both therapeutic and prophylactic actions. Those in need of treatment include the state in which a disease has developed and the state in which the disease should be prevented. In the treatment of tumors, a therapeutic agent may function to directly reduce the pathology of tumor cells or make the tumor cells more susceptible to treatment through other therapeutic agents, for example, radiation, chemotherapy and/or immunotherapy. As used herein, the term "alleviated" or "treated" means a sign that approaches a normalized value measured by conventional statistical tests. The sign approaching a normalized value is, for example, a value obtained from a healthy patient or individual which has a difference from the normalized value by less than 50%, preferably by less than 25%, and more preferably by less than 10%, and even more preferably has a slight difference from the normalized value.

The term "treatment of cancer" means any one or more of the following effects: 1) inhibition of tumor growth, including i) slowing or ii) complete growth arrest; 2) reduction in the number of tumor cells; 3) maintenance of tumor size; 4) reduction in tumor size; 5) inhibition of infiltration of tumor cells into peripheral organs including i) reduction or ii) slowing or iii) complete prevention; 6) inhibition of metastasis, including i) reduction or ii) slowing or iii) complete prevention; and 7) enhancement of the anti-tumor immune response, which may cause i) maintenance of tumor size, ii) reduction in tumor size, iii) slowing of growth of a tumor, or iv) reduction, slowing or prevention of invasion.

As used herein, the term "effective amount" or "therapeutically effective amount" refers to a sufficient amount of the compound disclosed herein that relieves to some extent the symptoms of a disease or condition to be treated (e.g., cancer or inflammatory disease, periodontal disease, or mineralization of soft tissue). In some embodiments, the outcome is 1) reduction and/or alleviation of the signs, symptoms or causes of a disease, or 2) any other desirable alteration of a biological system in clinical environments. In some embodiments, an appropriate "effective" amount for any individual case is determined using techniques such as dose escalation studies.

In some embodiments, the term "effective amount" refers to an effective amount to inhibit ENPP1 by about 20% (20% inhibition), at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), upon administration of an amount of the compound disclosed herein, i.e., one or more doses, in a single therapy or combination therapy, when compared to ENPP1 activity in a subject not treated with the compound, or when compared in ENPP1 activity before or after treatment with the compound.

In some embodiments, the term "therapeutically effective amount" refers to an effective amount to reduce a tumor burden of a subject by about 20%, at least about 30%, at least about 40%, at least about 50%, at least about 60%, at least about 70%, at least about 80%, or at least about 90%, upon administration of an amount of the compound disclosed herein, i.e., one or more doses, in a single therapy or combination therapy, when compared to a tumor burden of a subject not treated with the compound, or when compared in the tumor burden of a subject before or after treatment with the compound. As used herein, the term "tumor burden" means the total mass of tumor tissue of a subject with cancer.

In some embodiments, the term "therapeutically effective amount" refers to a dose used for radiotherapy required to observe tumor shrinkage in a subject by about 20%, at least about 30%, at least about 40%, at least about 50%, at least about 60%, at least about 70%, at least about 80%, or at least about 90%, upon administration of an amount of the compound disclosed herein, i.e., one or more doses, in a single therapy or combination therapy, when compared to the dose of radiotherapy required to observe tumor shrinkage in a subject not treated with the compound.

Hereinafter, the present invention will be described in detail.

As a result of continuous research to solve the above problems, the present inventors developed a compound for inhibiting ENPP1, a composition for inhibiting ENPP1, and a method for inhibiting ENPP1. In one aspect, the present inventors developed the novel naphthyridinone derivative compound for inhibiting ENPP1, a pharmaceutically acceptable salt thereof, a hydrate and a stereoisomer thereof, a method for preparing the same, and a pharmaceutical composition for preventing or treating cancer containing the same as an active ingredient. In one embodiment, the method includes treating a sample with a cell-permeable ENPP1 inhibitor to inhibit cGAMP hydrolysis attributable to ENPP1. In one embodiment, the method includes administering to the patient or subject a therapeutically effective amount of cell-permeable ENPP1 inhibitor to treat cancer. The compound according to one aspect of the present invention, a composition containing the same, or the compound and the composition may be used for various applications or diseases requiring inhibition of ENPP1.

cGAS-STING Pathway, Immunogenic Apoptosis, and Production of Type 1 IFNs

Cytoplasmic double-stranded DNA may be introduced from outside cells through microbial infection or vesicular transfer from adjacent dead cells. Cytoplasmic DNA may also be derived from damaged genomic DNA or mitochondrial DNA inside cells. Once cytoplasmic DNA is present, it may be detected by various DNA sensors such as RNA polymerase III, DDX41, DAI, IFI6, cGAS, LEEFIP1, DHX9, DHX36, Ku70 and AIM2.

Cyclic-GMP-AMP synthase (cGAS) is a cytoplasmic protein present as a dimer and consists of two DNA-binding domains and a nucleotidyltransferase domain (that converts ATP and GTP to cyclic dinucleotide 2',3-cGAMP having 2',5' and 3',5' phosphodiesters bonds). In addition, cGAMP acts as a secondary messenger and binds to STING with high affinity (Kd~4 nM) to induce type 1 IFN expression.

STING (also known as TMEM173, MITA, or MPYS) is an endoplasmic reticulum (ER) anchor protein containing four transmembrane domains at the N-terminus and a dimerization domain at the C-terminus. Upon binding to cGAMP, STING forms a tetramer and translocates from the ER to the ER-Golgi intermediate compartment. In the Golgi apparatus, STING attracts and activates tank binding kinase 1 (TBK1), the activated TBK1 phosphorylates the C-terminal domain of STING, and STING recruits and activates interferon regulatory factor 3 (IRF3). Then, the activated IRF3 migrates to the nucleus and promotes the expression of immune-stimulated genes (ISG) and type 1 IFN. After activation, STING is transferred to endolysosomes and is then degraded. At this time, cGAS-STING pathway activation is terminated.

Immunogenic Cell Death (ICD)

Immunogenic cell death (ICD), which is a type of cell death, refers to a cellular phenomenon that induces activation of a controlled immune response. Cell death is characterized by an apoptotic morphology and maintains the integrity of the biological membrane. ICD is also characterized by the secretion of DAMPs (e.g., calreticulin, high mobility group box 1 (HMGB1), ATP and Hsp70/90 proteins) as well as exposure of polypeptides formed by native or mutated proteins to the cells. The exposed polypeptides (acting as antigens) are recognized by dendritic cells (DCs) and subsequently prime effector T-cell lymphocytes to activate an adaptive immune response.

ICD may also be further classified based on different types of ICD inducers, such as 1) radiation (e.g., UV radiation or gamma radiation), 2) small chemotherapy molecules (e.g., doxorubicin or paclitaxel), and 3) biological agents (e.g., polypeptides, oligosaccharides, lipids or nucleic acids).

Radiation Therapy

Radiation therapy is well known and used for the treatment of patients suffering from a variety of diseases. Radiation therapy is typically used to inhibit the death or growth of undesirable tissue (e.g., cancerous tissue). The determined amount of high-energy electromagnetic radiation and/or high-energy particles aims to minimize unintended damage to desirable or healthy tissue while directly damaging undesirable tissues or lesions on the path through which the radiation passes.

The results of research so far showed that, since the effect on normal tissue depends more greatly on the fraction size than the dose, the 1.8-2.0-Gy fractional dose is regarded as the standard of the conventional radiation therapy and thus the treatment time is longer. In fact, a small dose per fraction induces the tumor effect by mitotic death of cancer cells and restores sublethal damage to normal tissues after administration. Stereotactic body radiation therapy (SBRT) is an improved radiation therapy that uses sophisticated image guidance to pinpoint the three-dimensional location of tumors so that radiation can be delivered more accurately to cancer cells. In addition to direct cytotoxicity, SBRT has substantial effects on tumor cell death at high doses accompanying microvascular damage, thus adding a novel mechanism of radiation-induced damage. However, a recent report has shown that high-dose radiation induces the expression of nuclease enzymes to attenuate the effects of radiation on STING-mediated innate immune activation.

Pathogen

As described above, intracellular invasion of nucleic acids derived from pathogens activates the cGAS-STING pathway, thereby increasing the immune response to pathogens. In some cases, the pathogen is a virus, such as a DNA virus or RNA virus. In some cases, the pathogen is a retrovirus. Examples of viruses that activate the cGAS-STING pathway include, but are not limited to, herpes simplex virus 1 (HSV-1), Kaposi's sarcoma-associated herpesvirus (KSHV), vaccinia virus (VACV), adenovirus, human papilloma virus (HPV), hepatitis B virus (HBV), hepatitis C virus (HCV), dengue virus (DENV), Zika virus (ZIKV), influenza A virus (IAV), human immunodeficiency virus (HIV), or human cytomegalovirus (HCMV). In other embodiments, the pathogen is a bacterium. Examples of bacteria include, but are not limited to, *Listeria monocytogenes, Mycobacterium tuberculosis, Francisella novicida, Legionella pneumophila, Chlamydia trachomatis, Streptococcus pneumoniae*, and *Neisseria gonorrhoeae*.

Phosphodiesterases

Phosphodiesterases (PDEs) include cyclic nucleotide phosphodiesterases, phospholipases C and D, autotaxin, sphingomyelin phosphodiesterases, DNases, RNases, restriction endonucleases, and a number of less well known small molecule phosphodiesterases. A group of exemplary PDE enzymes are important for hydrolysis of the cyclic nucleotides adenosine 3',5'-cyclic monophosphate (cAMP) and guanosine 3',5'-cyclic monophosphate (cGMP) into the inactive 5' monophosphate thereof.

Cyclic nucleotide phosphodiesterases contain a group of enzymes that cleave phosphodiester bonds of the cyclic nucleotide secondary messenger molecules, namely, cAMP and cGMP. They regulate the localization, persistence and amplification of cyclic nucleotide signals in subcellular domains.

Ecto-Nucleotide Pyrophosphatases/Phosphodiesterase

The class of phosphodiesterases also includes ecto-nucleotide pyrophosphatases/phosphodiesterases. Ecto-nucleotide pyrophosphatases/phosphodiesterase (ENPP) or nucleotide pyrophosphatase/phosphodiesterase (NPP) is a group of enzymes of ectonucleotidases that hydrolyze the pyrophosphate and phosphodiester bonds of substrates thereof to form nucleotide 5'-monophosphates (or phospholipids and phosphocholines). In some embodiments, the ENPP enzyme group includes seven enzymes of ectonucleotidases (ENPP-1, ENPP-2, ENPP-3, ENPP-4, ENPP-5, ENPP-6 and ENPP-7) having a similar protein structure on the cell surface.

ENPP enzymes usually have a modular structure including a catalytic domain of 400 amino acids. This catalytic domain is not related to phospholipase, Nudix hydrolase or ectonucleoside triphosphate diphosphohydrolase, although it exhibits partially overlapping activities. ENPPs 1 and 3 are predicted to have a transmembrane domain at the N-terminus thereof and a nuclease-like domain at the C-terminus thereof and to be type 2 single-spanning transmembrane proteins whose catalytic domains are directed towards the extracellular domain. ENPP 2, which lacks a transmembrane domain at either the N- or C-terminus thereof, is expected to have a signal peptide at the N-terminus thereof and to be secreted extracellularly. ENPPs 4, 5, 6, and 7 containing putative N-terminal signal peptides and C-terminal transmembrane domains are also predicted to be type 1 single-spanning transmembrane proteins whose catalytic domains are directed to the extracellular domain.

ENPPs 1, 2 and 3 are known to generate nucleoside monophosphates (ENPPs 1, 2 and 3) or nucleoside diphosphates (ENPPs 1 and 2) using nucleotides and derivatives thereof as substrates. It is known that only ENPP2 uses lysophospholipids. ENPPs 6 and 7 are known to produce choline phosphates using choline phosphate esters as substrates. For ENPPs 4 and 5, there is no known substrate.

ENPP1, which is also called NPP1 or PC-1, is a type 2 transmembrane glycoprotein and is expressed in a variety of tissues (pancreas, kidney, bladder and liver). ENPP1 is essential for purinergic signaling, which plays an important role in the regulation of cardiovascular, neuronal, immune and blood functions in mammals. ENPP1 catalyzes the hydrolysis of ATP or GTP to AMP or GMP to produce inorganic pyrophosphate (PPi). In general, since inorganic pyrophosphate regulates the mineralization of bone and cartilage, the production of PPi by ENPP1 makes ENPP1 a central regulator of bone and cartilage development. In contrast to the inhibitory effect of excessive PPi produced by ENPP1 in joint tissue, formation of calcium phosphate from PPi produced by ENPP1 is essential for mineralization of bone tissue. ENPP1 has broad specificity and hydrolyzes a variety of substrates, including phosphodiester linkages of nucleotides and nucleotide sugars and pyrophosphate linkages of nucleotides and nucleotide sugars.

Recently, ENPP1 has been found to play an important role in the immunological response to various extrinsic signals that activate the cGAS-STING pathway. An exploratory study of enzymatic activity degrading cGAMP molecules revealed that ENPP1 functions as a major hydrolase of cGAMP. Consistent with these findings, it was reported that the half-life of cGAMP was greatly dependent on ENPP1 based on verification of a much longer cGAMP half-life in ENPP1 knockout mice.

The bisphosphothionate analogue of cGAMP, which is resistant to ENPP1 hydrolysis, was shown to activate STING ten times more effectively than cGAMP, which indicates that delay or reduction of cGAMP hydrolysis by inhibition of ENPP1 can greatly increase the activation of STING. It has been reported that inhibition of ENPP1 induces the presence of persistent cGAMP to activate the STING pathway, thereby attenuating pseudorabies virus infection and reducing *Mycobacterium tuberculosis* infection.

Accordingly, in one aspect, the present invention provides an inhibitor of ENPP1, which is a cGAMP-degrading polypeptide.

In one aspect, the ENPP1 inhibitor is a reversible inhibitor.

In one aspect, the ENPP1 inhibitor is a competitive inhibitor.

In one aspect, the ENPP1 inhibitor is an allosteric inhibitor.

In one aspect, the ENPP1 inhibitor is an irreversible inhibitor.

In one aspect, the inhibitor of ENPP1 binds to a phosphodiesterase (PDE) catalytic domain to which AMP or GMP is bound.

In one aspect, the inhibitor of ENPP1 binds to the PDE catalytic domain, but weakly binds thereto when AMP is bound thereto.

In another aspect, the inhibitor of ENPP1 does not inhibit the ATP hydrolytic activity of the catalytic domain or weakly inhibits the ATP hydrolytic activity thereof.

Method for Inhibiting ENPP1

As mentioned above, the present invention includes the following configurations: 1) an ENPP1 inhibitor; 2) a method of inhibiting an ENPP1 enzyme using the ENPP1 inhibitor; 3) a method of inhibiting the hydrolase activity of ENPP1 to cGAMP; 4) a method of improving the signal output of STING path activation; and 5) a method of inhibiting tumor growth in an appropriate mouse tumor model in a single or combination therapy setting.

In some embodiments, inhibition of ENPP1 means that the activity of ENPP1 is reduced by 10% or more, for example 20% or more, 30% or more, 40% or more, 50% or more, 60% or more, 70% or more, 80% or more, 90% or more, or 95% or more, compared to a control not treated with the compound. In some embodiments, inhibition of ENPP1 means that the activity of ENPP1 is reduced by at least 2 times, for example at least 3 times, at least 5 times, at least 10 times, at least 100 times, or at least 1,000 times, compared to a control not treated with the compound.

In some embodiments, the cell-permeable ENPP1 inhibitor is an inhibitor as described herein. In some embodiments, the cell-penetrable ENPP1 inhibitor is an inhibitor for any one compound selected from the naphthyridinone derivative compound represented by Formula 1, the pharmaceutically acceptable salt thereof, the hydrate thereof, and the stereoisomer thereof.

[Formula 1]

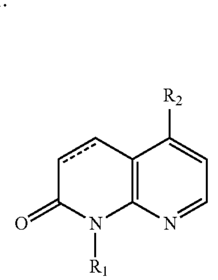

In some embodiments, the cell-permeable ENPP1 inhibitor is any one of the following compounds:

Compound No. 1: tert-butyl(3-(7-oxo-7,8-dihydro-1,8-naphthyridin-4-yl)phenyl)carbamate;

Compound No. 2: tert-butyl(3-(7-oxo-7,8-dihydro-1,8-naphthyridin-4-yl)benzyl)carbamate;

Compound No. 3: tert-butyl(4-(7-oxo-7,8-dihydro-1,8-naphthyridin-4-yl)benzyl)carbamate;

Compound No. 4: tert-butyl(2-fluoro-4-(7-oxo-7,8-dihydro-1,8-naphthyridin-4-yl)benzyl)carbamate;

Compound No. 5: tert-butyl(4-(8-methyl-7-oxo-7,8-dihydro-1,8-naphthyridin-4-yl)benzyl)carbamate;

Compound No. 6: 5-(3-(aminophenyl)-1,8-naphthyridin-2(1H)-one hydrochloride;

Compound No. 7: 5-(3-(aminomethyl)phenyl)-1,8-naphthyridin-2(1H)-one hydrochloride;

Compound No. 8: 5-(5-(amino-2-fluorophenyl)-1,8-naphthyridin-2(1H)-one hydrochloride;

Compound No. 9: 5-(3-(aminomethyl)-4-fluorophenyl)-1,8-naphthyridin-2(1H)-one hydrochloride;

Compound No. 10: 5-(4-(aminomethyl)phenyl)-1,8-naphthyridin-2(1H)-one hydrochloride;

Compound No. 11: 5-(4-(aminomethyl)-2-fluorophenyl)-1,8-naphthyridin-2(1H)-one hydrochloride;

Compound No. 12: 5-(4-(aminomethyl)-3-fluorophenyl)-1,8-naphthyridin-2(1H)-one hydrochloride;

Compound No. 13: 5-(4-(aminomethyl)-2,3-difluorophenyl)-1,8-naphthyridin-2(1H)-one hydrochloride;

Compound No. 14: 5-(4-(1-aminoethyl)phenyl)-1,8-naphthyridin-2(1H)-one hydrochloride;

Compound No. 15: (R)-5-(4-(1-aminoethyl)phenyl)-1,8-naphthyridin-2(1H)-one hydrochloride;

Compound No. 16: 5-(4-(2-aminopropan-2-yl)phenyl)-1,8-naphthyridin-2(1H)-one hydrochloride;

Compound No. 17: (R)-5-(4-(1-(methylaminoethyl)phenyl)-1,8-naphthyridin-2(1H)-one hydrochloride;

Compound No. 18: (S)-5-(4-(1-(methylaminoethyl)phenyl)-1,8-naphthyridin-2(1H)-one hydrochloride;

Compound No. 19: (R)-5-(4-(1-(cyclopropylaminoethyl)phenyl)-1,8-naphthyridin-2(1H)-one hydrochloride;

Compound No. 20: 5-(4-((ethylamino)methyl)-2-fluorophenyl)-1,8-naphthyridin-2(1H)-one hydrochloride;

Compound No. 21: 5-(2-fluoro-4-((isopropylamine)methyl)phenyl)-1,8-naphthyridin-2(1H)-one hydrochloride;

Compound No. 22: 5-(4-((cyclopropylamino)methyl)-2-fluorophenyl)-1,8-naphthyridin-2(1H)-one hydrochloride;

Compound No. 23: 5-(3-fluoro-4-((methylamino)methyl)phenyl)-1,8-naphthyridin-2(1H)-one hydrochloride;

Compound No. 24: 5-(4-((ethylamino)methyl)-3-fluorophenyl)-1,8-naphthyridin-2(1H)-one hydrochloride;

Compound No. 25: 5-(4-((cyclopropylamino)methyl)-3-fluorophenyl)-1,8-naphthyridin-2(1H)-one hydrochloride;

Compound No. 26: 5-(isoindolin-5-yl)-1,8-naphthyridin-2(1H)-one hydrochloride;

Compound No. 27: 5-(1,2,3,4-tetrahydroisoquinolin-7-yl)-1,8-naphthyridin-2(1H)-one hydrochloride;

Compound No. 28: 5-(6-fluoro-1,2,3,4-tetrahydroisoquinolin-7-yl)-1,8-naphthyridin-2(1H)-one hydrochloride;

Compound No. 29: 5-(4-(aminomethyl)phenyl)-1-methyl-1,8-naphthyridin-2(1H)-one hydrochloride;

Compound No. 30: tert-butyl(N-(3-(7-oxo-7,8-dihydro-1,8-naphthyridin-4-yl)phenyl)sulfamoyl)carbamate;

Compound No. 31: tert-butyl(N-(3-(7-oxo-7,8-dihydro-1,8-naphthyridin-4-yl)benzyl)sulfamoyl)carbamate;

Compound No. 32: tert-butyl(N-(4-(7-oxo-7,8-dihydro-1,8-naphthyridin-4-yl)benzyl)sulfamoyl)carbamate;

Compound No. 33: tert-butyl(N-(2-fluoro-4-(7-oxo-7,8-dihydro-1,8-naphthyridin-4-yl)benzyl)sulfamoyl)carbamate;

Compound No. 34: tert-butyl(N-(4-(8-methyl-7-oxo-7,8-dihydro-1,8-naphthyridin-4-yl)benzyl)sulfamoyl)carbamate;

Compound No. 35: N-(3-(7-oxo-7,8-dihydro-1,8-naphthyridin-4-yl)phenyl)sulfamide;

Compound No. 36: N-(2-fluoro-5-(7-oxo-7,8-dihydro-1,8-naphthyridin-4-yl)phenyl)sulfamide hydrochloride;

Compound No. 37: N-(3-(7-oxo-7,8-dihydro-1,8-naphthyridin-4-yl)benzyl)sulfamide;

Compound No. 38: N-(2-fluoro-5-(7-oxo-7,8-dihydro-1,8-naphthyridin-4-yl)benzyl)sulfamide hydrochloride;

Compound No. 39: N-(4-(7-oxo-7,8-dihydro-1,8-naphthyridin-4-yl)phenyl)sulfamide;

Compound No. 40: N-(4-(7-oxo-7,8-dihydro-1,8-naphthyridin-4-yl)benzyl)sulfamide;

Compound No. 41: N-(2-fluoro-4-(7-oxo-7,8-dihydro-1,8-naphthyridin-4-yl)benzyl)sulfamide;

Compound No. 42: N-(3-fluoro-4-(7-oxo-7,8-dihydro-1,8-naphthyridin-4-yl)benzyl)sulfamide hydrochloride;

Compound No. 43: N-(2,3-difluoro-4-(7-oxo-7,8-dihydro-1,8-naphthyridin-4-yl)benzyl)sulfamide hydrochloride;

Compound No. 44: N-(3,5-difluoro-4-(7-oxo-7,8-dihydro-1,8-naphthyridin-4-yl)benzyl)sulfamide hydrochloride;

Compound No. 45: N-(1-(4-(7-oxo-7,8-dihydro-1,8-naphthyridin-4-yl)phenyl)ethyl)sulfamide hydrochloride;

Compound No. 46: (R)-(N-(1-(4-(7-oxo-7,8-dihydro-1,8-naphthyridin-4-yl)phenyl)ethyl)sulfamide hydrochloride;

Compound No. 47: (S)-(N-(1-(4-(7-oxo-7,8-dihydro-1,8-naphthyridin-4-yl)phenyl)ethyl)sulfamide hydrochloride;

Compound No. 48: (R)-(N-(1-(2-fluoro-4-(7-oxo-7,8-dihydro-1,8-naphthyridin-4-yl)phenyl)ethyl)sulfamide hydrochloride;

Compound No. 49: (R)-(N-(1-(3-fluoro-4-(7-oxo-7,8-dihydro-1,8-naphthyridin-4-yl)phenyl)ethyl)sulfamide hydrochloride;

Compound No. 50: N-methyl-N-(4-(7-oxo-7,8-dihydro-1,8-naphthyridin-4-yl)benzyl)sulfamide hydrochloride;

Compound No. 51: N-ethyl-N-(4-(7-oxo-7,8-dihydro-1,8-naphthyridin-4-yl)benzyl)sulfamide hydrochloride;

Compound No. 52: N-(2-fluoro-4-(7-oxo-7,8-dihydro-1,8-naphthyridin-4-yl)benzyl)-N-methylsulfamide hydrochloride;

Compound No. 53: N-ethyl-N-(2-fluoro-4-(7-oxo-7,8-dihydro-1,8-naphthyridin-4-yl)benzyl)sulfamide hydrochloride;

Compound No. 54: N-cyclopropyl-N-(2-fluoro-4-(7-oxo-7,8-dihydro-1,8-naphthyridin-4-yl)benzyl)sulfamide hydrochloride;

Compound No. 55: N-(3-fluoro-4-(7-oxo-7,8-dihydro-1,8-naphthyridin-4-yl)benzyl)-N-methylsulfamide hydrochloride;

Compound No. 56: N-ethyl-N-(3-fluoro-4-(7-oxo-7,8-dihydro-1,8-naphthyridin-4-yl)benzyl)sulfamide hydrochloride;

Compound No. 57: N-(3-fluoro-4-(7-oxo-7,8-dihydro-1,8-naphthyridin-4-yl)benzyl)-N-isopropyl)sulfamide hydrochloride;

Compound No. 58: N-cyclopropyl-N-(3-fluoro-4-(7-oxo-7,8-dihydro-1,8-naphthyridin-4-yl)benzyl)sulfamide hydrochloride;

Compound No. 59: (R)-(N-methyl-N-(1-(4-(7-oxo-7,8-dihydro-1,8-naphthyridin-4-yl)phenyl)ethyl)sulfamide hydrochloride;

Compound No. 60: (R)-(N-cyclopropyl-N-(1-(4-(7-oxo-7,8-dihydro-1,8-naphthyridin-4-yl)phenyl)ethyl)sulfamide hydrochloride;

Compound No. 61: (S)-(N-methyl-N-(1-(4-(7-oxo-7,8-dihydro-1,8-naphthyridin-4-yl)phenyl)ethyl)sulfamide hydrochloride;

Compound No. 62: (R)-(N-(1-(2-fluoro-4-(7-oxo-7,8-dihydro-1,8-naphthyridin-4-yl)phenyl)ethyl)sulfamide hydrochloride;

Compound No. 63: (R)-(N-(1-(3-fluoro-4-(7-oxo-7,8-dihydro-1,8-naphthyridin-4-yl)phenyl)ethyl)sulfamide hydrochloride;

Compound No. 64: 5-(7-oxo-7,8-dihydro-1,8-naphthyridin-4-yl)isoindolin-2-yl)sulfamide hydrochloride;

Compound No. 65: 7-(7-oxo-7,8-dihydro-1,8-naphthyridin-4-yl)dihydroisoquinoline-2(1H)-sulfamide hydrochloride;

Compound No. 66: 6-fluoro-7-(7-oxo-7,8-dihydro-1,8-naphthyridin-4-yl)-3,4-dihydroisoquinoline-2(1H)-sulfamide hydrochloride;

Compound No. 67: N-(4-(8-methyl-7-oxo-7,8-dihydro-1,8-naphthyridin-4-yl)benzyl)sulfamide;

Compound No. 68: N-(4-(7-oxo-7,8-dihydro-1,8-naphthyridin-4-yl)benzyl)methanesulfonamide;

Compound No. 69: 4-methyl-N-(4-(7-oxo-7,8-dihydro-1,8-naphthyridin-4-yl)benzyl)benzenesulfonamide;

Compound No. 70: N-(4-(7-oxo-7,8-dihydro-1,8-naphthyridin-4-yl)benzyl)thiophene-2-sulfonamide;

Compound No. 71: N-(4-(7-oxo-7,8-dihydro-1,8-naphthyridin-4-yl)benzyl)cyclopropanesulfonamide;

Compound No. 72: diethyl(4-(7-oxo-7,8-dihydro-1,8-naphthyridin-4-yl)benzyl)phosphonate;

Compound No. 73: diethyl(4-(7-oxo-7,8-dihydro-1,8-naphthyridin-4-yl)benzyl)phosphoamidate;

Compound No. 74: ethylhydrogen(4-(7-oxo-7,8-dihydro-1,8-naphthyridin-4-yl)benzyl)phosphonate;

Compound No. 75: (4-(7-oxo-7,8-dihydro-1,8-naphthyridin-4-yl)benzyl)phosphonic acid;

Compound No. 76: 5-((3-aminophenyl)amino)-1,8-naphthyridin-2(1H)-one dihydrochloride;

Compound No. 77: 5-((3-aminomethyl)phenyl)amino)-1,8-naphthyridin-2(1H)-one dihydrochloride;

Compound No. 78: 5-((3-aminomethyl)-4-fluorophenyl)amino)-1,8-naphthyridin-2(1H)-one dihydrochloride;

Compound No. 79: 5-((5-(2-aminoethyl)-2-fluorophenyl)amino)-1,8-naphthyridin-2(1H)-one dihydrochloride;

Compound No. 80: 5-((3-(2-methylphenylethyl)phenyl)amino)-1,8-naphthyridin-2(1H)-one dihydrochloride;

Compound No. 81: 5-((4-aminophenyl)amino)-1,8-naphthyridin-2(1H)-one dihydrochloride;

Compound No. 82: 5-((4-(aminomethyl)phenyl)amino)-1,8-naphthyridin-2(1H)-one dihydrochloride;

Compound No. 83: 5-((4-((cyclopropylamino)methyl)phenyl)amino)-1,8-naphthyridin-2(1H)-one dihydrochloride;

Compound No. 84: 5-((4-((cyclopropylamino)methyl)phenyl)amino)-1,8-naphthyridin-2(1H)-one dihydrochloride;

Compound No. 85: 5-((1,2,3,4-tetrahydroisoquinolin-6-yl)amino)-1,8-naphthyridin-2(1H)-one dihydrochloride;

Compound No. 86: 5-((7-fluoro-1,2,3,4-tetrahydroisoquinolin-6-yl)amino)-1,8-naphthyridin-2(1H)-one dihydrochloride;

Compound No. 87: 5-((2,3,4,5-tetrahydro-1H-benzo[c]azepin-8-yl)amine)-1,8-naphthyridin-2(1H)-one dihydrochloride;

Compound No. 88: N-(3-((7-oxo-7,8-dihydro-1,8-naphthyridin-4-yl)amino)phenyl)sulfamide dihydrochloride;

Compound No. 89: N-(3-((7-oxo-7,8-dihydro-1,8-naphthyridin-4-yl)amino)benzyl)sulfamide dihydrochloride;

Compound No. 90: N-(2-fluoro-5((7-oxo-7,8-dihydro-1,8-naphthyridin-4-yl)amino)benzyl)sulfamide dihydrochloride;

Compound No. 91: N-(4-fluoro-3-((7-oxo-7,8-dihydro-1,8-naphthyridin-4-yl)amino)benzyl)sulfamide dihydrochloride;

Compound No. 92: N-(3-((7-oxo-7,8-dihydro-1,8-naphthyridin-4-yl)amino)phenethyl)sulfamide dihydrochloride;

Compound No. 93: N-methyl-N-(3-((7-oxo-7,8-dihydro-1,8-naphthyridin-4-yl)amino)phenethyl)sulfamide dihydrochloride;

Compound No. 94: N-ethyl-N-(3-((7-oxo-7,8-dihydro-1,8-naphthyridin-4-yl)amino)phenethyl)sulfamide dihydrochloride;

Compound No. 95: N-(4-fluoro-3-((7-oxo-7,8-dihydro-1,8-naphthyridin-4-yl)amino)phenethyl)sulfamide dihydrochloride;

Compound No. 96: N-(4-fluoro-3-((7-oxo-7,8-dihydro-1,8-naphthyridin-4-yl)amino)phenethyl)-N-methylsulfamide dihydrochloride;

Compound No. 97: N-(4-((7-oxo-7,8-dihydro-1,8-naphthyridin-4-yl)amino)phenyl)sulfamide dihydrochloride;

Compound No. 98: N-(4-((7-oxo-7,8-dihydro-1,8-naphthyridin-4-yl)amino)benzyl)sulfamide dihydrochloride;

Compound No. 99: N-cyclopropyl-N-(4-((7-oxo-7,8-dihydro-1,8-naphthyridin-4-yl)amino)benzyl)sulfamide dihydrochloride;

Compound No. 100: N-(3-chloro-4-((7-oxo-7,8-dihydro-1,8-naphthyridin-4-yl)amino)benzyl)sulfamide dihydrochloride;

Compound No. 101: 5-((7-oxo-7,8-dihydro-1,8-naphthyridin-4-yl)amino)isoindolin-2-yl)sulfamide dihydrochloride;

Compound No. 102: 7-((7-oxo-7,8-dihydro-1,8-naphthyridin-4-yl)amino)-3,4-dihydroisoquinolin-2(1H)-yl)sulfamide dihydrochloride;

Compound No. 103: (8-((7-oxo-7,8-dihydro-1,8-naphthyridin-4-yl)amino)-1,3,4,5-tetrahydro-2 (1H)-benzo[c]azepin-2-yl)sulfamide dihydrochloride;

Compound No. 104: (6-((7-oxo-7,8-dihydro-1,8-naphthyridin-4-yl)amino)-3,4-dihydroisoquinolin-2(1H)-yl)sulfamide dihydrochloride;

Compound No. 105: 6-fluoro-7-((7-oxo-7,8-dihydro-1,8-naphthyridin-4-yl)amino)-3,4-dihydroisoquinolin-2(1H)-yl)sulfamide dihydrochloride;

Compound No. 106: (7-fluoro-6-((7-oxo-7,8-dihydro-1,8-naphthyridin-4-yl)amino)-3,4-dihydroisoquinolin-2(1H)-yl)sulfamide dihydrochloride;

Compound No. 107: N-(5-((7-oxo-7,8-dihydro-1,8-naphthyridin-4-yl)amino)-2,3-dihydro-1H-inden-2-yl)sulfamide dihydrochloride;

Compound No. 108: (7-(methyl(7-oxo-7,8-dihydro-1,8-naphthyridin-4-yl)amino)-3,4-dihydroisoquinolin-2 (1H)-yl) sulfamide dihydrochloride;

Compound No. 109: tert-butyl(1-(7-oxo-7,8-dihydro-1,8-naphthyridin-4-yl)piperidin-4-yl)carbamate;

Compound No. 110: tert-butyl((1-(7-oxo-7,8-dihydro-1,8-naphthyridin-4-yl)piperidin-4-yl)methyl)carbamate;

Compound No. 111: tert-butyl(2-(1-(7-oxo-7,8-dihydro-1,8-naphthyridin-4-yl)piperidin-4-yl)ethyl) carbamate;

Compound No. 112: tert-butyl((1-(8-methyl-7-oxo-7,8-dihydro-1,8-naphthyridin-4-yl)piperidin-4-yl)methyl)carbamate;

Compound No. 113: 5-(4-aminopiperidin-1-yl)-1,8-naphthyridin-2(1H)-one hydrochloride;

Compound No. 114: 5-(4-(aminomethyl)piperidin-1-yl)-1,8-naphthyridin-2(1H)-one hydrochloride;

Compound No. 115: 5-(4-(2-aminoethyl)piperidin-1-yl)-1,8-naphthyridin-2(1H)-one hydrochloride;

Compound No. 116: 5-(1,4-diazepan-1-yl)-1,8-naphthyridin-2(1H)-one hydrochloride;

Compound No. 117: 5-(2,8-diazaspiro[4,5]decan-8-yl)-1,8-naphthyridin-2(1H)-one hydrochloride;

Compound No. 118: 5-(4-(aminomethyl)piperidin-1-yl)-1-methyl-1,8-naphthyridin-2(1H)-one hydrochloride;

Compound No. 119: tert-butyl(N-(1-(7-oxo-7,8-dihydro-1,8-naphthyridin-4-yl)piperidin-4-yl)sulfamoyl)carbamate;

Compound No. 120: tert-butyl(N-((1-(7-oxo-7,8-dihydro-1,8-naphthyridin-4-yl)piperidin-4-yl)methyl)sulfamoyl) carbamate;

Compound No. 121: tert-butyl(N-(2-(1-(7-oxo-7,8-dihydro-1,8-naphthyridin-4-yl)piperidin-4-yl)ethyl)sulfamoyl) carbamate;

Compound No. 122: tert-butyl(N-((1-(8-methyl-7-oxo-7,8-dihydro-1,8-naphthyridin-4-yl)piperidin-4-yl)methyl)sulfamoyl)carbamate;

Compound No. 123: N-(1-(7-oxo-7,8-dihydro-1,8-naphthyridin-4-yl)piperidin-4-yl)sulfamide;

Compound No. 124: N-((1-(7-oxo-7,8-dihydro-1,8-naphthyridin-4-yl)piperidin-4-yl)methyl)sulfamide;

Compound No. 125: N-(2-(1-(7-oxo-7,8-dihydro-1,8-naphthyridin-4-yl)piperidin-4-yl)ethyl)sulfamide;

Compound No. 126: 8-(7-oxo-7,8-dihydro-1,8-naphthyridin-4-yl)-2,8-diazaspiro[4,5]decane-2-sulfamide;

Compound No. 127: 8-(7-oxo-7,8-dihydro-1,8-naphthyridin-4-yl)-2,8-diazaspiro[4,5]decane-2-sulfamide;

Compound No. 128: N-((1-(8-methyl-7-oxo-7,8-dihydro-1,8-naphthyridin-4-yl)piperidin-4-yl)methyl)sulfamide;

Compound No. 129: tert-butyl(3-(7-oxo-5,6,7,8-tetrahydro-1,8-naphthyridin-4-yl)benzyl)carbamate;

Compound No. 130: tert-butyl(4-(7-oxo-5,6,7,8-tetrahydro-1,8-naphthyridin-4-yl)benzyl)carbamate;

Compound No. 131: 5-(3-(aminophenyl)-3,4-dihydro-1,8-naphthyridin-2(1H)-one hydrochloride;

Compound No. 132: 5-(3-(aminomethyl)phenyl)-3,4-dihydro-1,8-naphthyridin-2(1H)-one hydrochloride;

Compound No. 133: 5-(4-(aminomethyl)phenyl)-3,4-dihydro-1,8-naphthyridin-2(1H)-one hydrochloride;

Compound No. 134: 5-(4-(2-aminopropan-2-yl)phenyl)-3,4-dihydro-1,8-naphthyridin-2(1H)-one hydrochloride;

Compound No. 135: 5-(1,2,3,4-tetrahydroisoquinolin-7-yl)-3,4-dihydro-1,8-naphthyridin-2(1H)-one hydrochloride;

Compound No. 136: tert-butyl(N-(3-(7-oxo-5,6,7,8-tetrahydro-1,8-naphthyridin-4-yl)benzyl)sulfamoyl)carbamate;

Compound No. 137: tert-butyl(N-(4-(7-oxo-5,6,7,8-tetrahydro-1,8-naphthyridin-4-yl)benzyl)sulfamoyl)carbamate;

Compound No. 138: tert-butyl((7-(7-oxo-5,6,7,8-tetrahydro-1,8-naphthyridin-4-yl)-3,4-diisoquinolin-2 (1H)-yl) sulfonyl) carbamate;

Compound No. 139: N-(3-(7-oxo-5,6,7,8-tetrahydro-1,8-naphthyridin-4-yl)phenyl)sulfamide;

Compound No. 140: N-(3-(7-oxo-5,6,7,8-tetrahydro-1,8-naphthyridin-4-yl)benzyl)sulfamide;

Compound No. 141: N-(4-(7-oxo-5,6,7,8-tetrahydro-1,8-naphthyridin-4-yl)benzyl)sulfamide;

Compound No. 142: N-(2-fluoro-4-(7-oxo-5,6,7,8-tetrahydro-1,8-naphthyridin-4-yl)benzyl)sulfamide;

Compound No. 143: 5-(7-oxo-5,6,7,8-tetrahydro-1,8-naphthyridin-4-yl)isoindoline-2-sulfamide hydrochloride Compound No. 144: (7-(7-oxo-5,6,7,8-tetrahydro-1,8-naphthyridin-4-yl)amino)-3,4-dihydroisoquinoline-2(1H)-sulfamide hydrochloride;

Compound No. 145: (7-(7-oxo-5,6,7,8-tetrahydro-1,8-naphthyridin-4-yl)-3,4-dihydroisoguinolin-2(1H)-yl)sulfamide hydrochloride;

Compound No. 146: N-(3-(7-oxo-5,6,7,8-tetrahydro-1,8-naphthyridin-4-yl)benzyl)methanesulfonamide;

Compound No. 147: 4-methyl-N-(3-(7-oxo-5,6,7,8-tetrahydro-1,8-naphthyridin-4-yl)benzyl)benzenesulfonamide; and Compound No. 148: N-(3-(7-oxo-5,6,7,8-tetrahydro-1,8-naphthyridin-4-yl)benzyl)thiophene-2-sulfonamide.

In some embodiments, the compounds of the present invention have an ENPP1 inhibition profile that reflects activity against additional enzymes. In some embodiments, the compounds of the present invention specifically inhibit ENPP1 without unintended inhibition of one or more other enzymes.

In some embodiments, the compounds of the present invention inhibit ENPP 1, which can be determined through assay for detecting the activity of enzymes in cell-free or cellular systems after treatment with the compounds of the present invention, compared to a control group by inhibition analysis, for example, by measurement of $IC_{50}$ or $EC_{50}$. In some embodiments, the compounds of the present invention have an $IC_{50}$ (or $EC_{50}$) of 10 μM or less, such as 3 μM or less, 1 μM or less, 500 nM or less, 300 nM or less, 200 nM or less, 100 nM or less, 50 nM or less, 30 nM or less, 10 nM or less, 5 nM or less, 3 nM or less, 1 nM or less, or an even lower value.

The procedure of the assay that can be used to determine the activity of ENPP1 may include, but is not limited to, the following assay procedures including cell-free assay systems, such as avidity assays, assays using purified enzymes, cell assays for determining phenotypes of cells, such as gene expression assays and in vivo assays involving specific animals.

In some embodiments, the method of the present invention is a method of suppressing cancer cell proliferation, the method including treating the cells with an effective amount of the compound of the present invention to suppress cancer cell proliferation. In some embodiments, the method may be performed in combination with chemotherapy. Any cancer cells may be used as long as they are available.

Treatment Method

As mentioned above, the present invention includes methods for inhibiting ENPP1 activity against cGAMP to cause increased levels of cGAMP and/or modulation of downstream factors of the STING pathway. A recent report has shown that ENPP1 inhibition can modulate STING activity in vivo, and thus can be used for the treatment of various diseases, such as cancer immunotherapy or treatment of infectious diseases. As described above, the method of the present invention is a method of increasing the STING-mediated response and regulating the immune response in a subject.

In some embodiments, the STING-mediated response includes increasing production of interferon (e.g., type 1 interferon, type 3 interferon) in the subject. Interferons (IFNs) are a group of signaling proteins produced and released by host cells in response to the presence of one or more pathogens to enhance the defenses of surrounding cells against the pathogens. IFNs also have a variety of other functions of 1) activating immune cells such as NK cells and macrophages, and of 2) promoting host defense by upregulating antigen presentation through increased expression of major histocompatibility complex (MHC) antigens. IFNs are generally classified into three classes: type 1 IFNs, type 2 IFNs, and type 3 IFNs. Mammalian type 1 INFs include IFN-α (alpha), IFN-β (beta), IFN-δ (delta), IFN-ε (epsilon), IFN-κ (kappa), IFN-τ (tau), IFN-ω (omega), and IFN-ζ (zeta). All type 1 IFNs bind to a specific cell surface receptor complex known as an IFN-α/β receptor (IFNAR), which consists of IFNAR1 and IFNAR2 chains.

Interferons have been studied as cancer therapeutics due to the antitumor activity thereof, which exhibit two different effects, namely, tumor-intrinsic and/or immunomodulatory effects. IFNs regulate the expression of a number of genes that directly affect tumor cell growth, proliferation, differentiation, survival, migration and other specific functions. In some cases, in vitro treatment using type 1 IFN has a direct antiproliferative effect due to prolonging of all phases of the cell cycle by IFN. In some cases, CRKL, which is a type of CRK protein activated by type 1 IFN, interacts with the tumor suppressor, small G-protein RAP1A to inhibit RAS family GTPase, resulting in growth arrest of cancer cells. IFNs are known to regulate two major apoptotic responses. The two apoptotic responses are extrinsic (apoptotic receptor-mediated pathway) and intrinsic (mitochondrial) pathways. In response to type 1 IFN, upregulation of sensor protein activation (e.g., DR receptor) occurs, which causes apoptosis of tumor cells.

IFNs have extrinsic effects on tumors through regulation of processes such as angiogenesis, osteoclastogenesis and immunity. Both endogenous and exogenous type 1 IFNs play a major role in the activity of anticancer immunity. For example, type 1 IFNs enhance the activity of α/β T cells, γ/δ T cells, NK cells and dendritic cells, and inhibit the activity of immune-suppressive cells, for example, conversion of regulatory T cells, bone marrow-derived suppressor cells and tumor-associated macrophages. Type 1 IFN also acts directly on tumor cells to improve antigen expression and up-regulate numerous immune-interacting molecules (e.g., stress ligands recognized by major histocompatibility complex class 1 (MHCI)) and germline-encoded immunoreceptors.

In one aspect, the method includes administering a therapeutically effective amount of the ENPP1 inhibitor to a subject having cancer to treat the cancer of the subject. In one embodiment, the subject may be a subject diagnosed with or suspected of having cancer. Any suitable ENPP1 inhibitor may be used in the subject. In one embodiment, the cancer is selected from adrenal gland cancer, liver cancer, kidney cancer, bladder cancer, breast cancer, colon cancer, stomach cancer, ovarian cancer, cervical cancer, uterus cancer, esophageal cancer, colorectal cancer, prostate cancer, pancreatic cancer, lung (small and non-small cell) cancer, thyroid cancer, carcinoma, sarcoma, glioblastoma, melanoma, and head and neck cancer. In one embodiment, the cancer is lymphoma.

In one embodiment, the effective amount of the compound ranges from about 10 ng to about 100 mg, e.g., from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 μg to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount may be a single dose or a total daily dose. The total daily amount may range from 10 ng to 100 mg, or from 100 mg to about 500 mg, or from 500 mg to about 1,000 mg.

In one embodiment, the compound is administered in a single dose. In other embodiments, multiple doses are administered. When the multiple doses are administered over a period of time, the compound is administered twice a day (bid), once a day (qd), every other day (qod), every 3 days, 3 times a week (tiw), or twice a week (biw).

Combination Therapy

The ENPP1 inhibitor compound of the present invention may be administered to a subject alone or in combination with an additional active agent or additional therapy, e.g., radiation therapy. The terms "agent", "compound" and "drug" are used interchangeably herein. In one embodiment, the method of the present invention further includes administering to the subject an additional agent, e.g., a small molecule, a chemotherapeutic agent, an antibody, an antibody-drug conjugate, an aptamer, a protein, an immune checkpoint inhibitor, or radiotherapy concomitantly or sequentially in combination.

The term "co-administration" or "in combination with" includes the administration of two or more therapeutic agents simultaneously, concurrently, or sequentially, without any specific time limit. In some embodiments, agonists or agents are concurrently present in cells or subjects or simultaneously exert biological or therapeutic effects. In some embodiments, the therapeutic agents are in the form of an identical composition or unit dosage form. In some embodiments, the therapeutic agents are separate compositions or unit dosage forms. In some embodiments, the first therapeutic agent is administered prior to administration of the second therapeutic agent (e.g., 5 minutes before, 15 minutes before, 30 minutes before, 45 minutes before, 1 hour before, 2 hours before, 4 hours before, 6 hours before, 12 hours before, 24 hours before, 48 hours before, 72 hours before, 96 hours before, 1 week before, 2 weeks before, 3 weeks before, 4 weeks before, 5 weeks before, 6 weeks before, 8 weeks before, 12 weeks before), concomitantly with the administration of the second therapeutic agent, or after the administration of the second therapeutic agent (e.g., 5 minutes after, 15 minutes after, 30 minutes after, 45 minutes after, 1 hour after, 2 hours after, 4 hours after, 6 hours after, 12 hours after, 24 hours after, 48 hours after, 72 hours after, 96 hours after, 1 week after, 2 weeks after, 3 weeks after, 4 weeks after, 5 weeks after, 6 weeks after, 8 weeks after, or 12 weeks after).

The "concomitant administration" of additional therapy based on a known therapeutic agent or the composition including the disclosed compound of the present invention means a combination of the compound and the second agent or additional therapy such that both the known agent and the composition including the disclosed compound have therapeutic effects. The concomitant administration may include simultaneous or previous administration of drugs in conjunction with administration of the compound of the present invention. The routes of administration of the two agents may vary and representative routes of administration are described in detail below. Those skilled in the art will have no difficulty determining the appropriate administration time, sequence and dosage for the drug or therapy and the compound disclosed herein.

The "concomitant administration" of additional therapy based on a known therapeutic agent or the composition including the disclosed compound of the present invention means a combination of the compound and the second agent or additional therapy such that both the known agent and the composition including the disclosed compound have therapeutic effects. The concomitant administration may include simultaneous or previous administration of drugs in conjunction with administration of the compound of the present invention. The routes of administration of the two agents may vary and representative routes of administration are described in detail below. Those skilled in the art will have no difficulty determining the appropriate administration time, sequence and dosage for the drug or therapy and the compound disclosed herein.

For the treatment of cancer, the ENPP1 inhibitor compounds may be administered in combination with a chemotherapeutic agent selected from the group consisting of alkylating agents, anti-metabolites, anti-tumor antibiotics, plant alkaloids, taxanes, nucleoside analogues, anthracyclines, thymidylate-targeting drugs, apoptosis modulators, cell cycle control inhibitors, colony stimulation factor-1 receptor inhibitors, CD47 inhibitors and the other.

Combination with Immunotherapeutic Agents

For the treatment of cancer, the ENPP1 inhibitor compound may be administered in combination with an immunotherapeutic agent. The immunotherapeutic agent is an agonist suitable for the treatment of cancer by inducing, enhancing, or inhibiting an immune response. In some embodiments, the immunotherapeutic agent is an immune checkpoint inhibitor. Any immunosuppressant may be used. For example, the immune checkpoint inhibitor may be a cytotoxic T-lymphocyte-associated antigen 4 (CTLA-4) inhibitor, a programmed death 1 (PD-1) inhibitor or programmed cell death ligand 1 (PD-L1) inhibitor, but is not limited thereto. Examples of the immune checkpoint inhibitor include, but are not limited to, ipilimumab, pembrolizumab, nivolumab, atezolizumab, avelumab, durvalumab, cemiplimab and the like. In some embodiments, the immunotherapeutic agent is immune cell therapy. Any suitable cell therapy may be used and examples thereof include, without being limited to, chimeric antigen receptor T cell therapy, chimeric antigen receptor NK cell therapy, and other cell therapies.

For the treatment of cancer, the ENPP1 inhibitor compound may be administered in combination with a suitable cancer vaccine regimen, for example, a dendritic cell vaccine that promotes Th1/Th17 immunity. In some cases, the ENPP1 inhibitor compound is suitable for use as an adjuvant therapy in combination with Th-17-inducing vaccination.

Combination with Radiation Therapy

For cancer treatment methods, the ENPP1 inhibitor compound may be administered in combination with radiation therapy. In some embodiments, the ENPP1 inhibitor compound may be administered before or after radiation therapy. The combination of radiation therapy and administration of the compound of the present invention may provide a synergistic therapeutic effect. When the subject is subjected to radiation therapy (RT) at an appropriate dose and/or frequency during radiation therapy (RT), cGAMP may be produced in the subject. The ENPP1 inhibitor compound can enhance therapeutic efficacy on the subject by preventing degradation of the produced cGAMP, compared to the level of cGAMP produced by, for example, RT alone. As such, the details of the methods of the present invention include administration of the reduced dose and/or frequency and/or regime of radiation therapy as compared to the dosage and/or frequency and/or reduction of the therapeutic effect of radiation therapy alone. In some embodiments, radiation therapy is administered in combination with the compound of the present invention at a dosage and/or frequency effective to reduce the risk of radiation damage, e.g., the risk of radiation damage to the subject, expected by a therapeutically effective amount.

In one embodiment, the method includes administering to the subject an ENPP1 inhibitor prior to radiation therapy. In one embodiment, the method includes administering an ENPP1 inhibitor to a subject after exposure of the subject to radiation therapy. In another embodiment, the method includes sequentially administering to a subject in need thereof radiation therapy, followed by an ENPP1 inhibitor, followed by an immune checkpoint inhibitor.

Combination with Anti-Cancer Vaccine

For cancer treatment methods, the ENPP1 inhibitor compound may be administered in conjunction with an anti-cancer vaccine. In some embodiments, the ENPP1 inhibitor compound may be administered before or after administration of anti-cancer vaccine.

Combination with CAR-T

For cancer treatment methods, the ENPP1 inhibitor compound may be administered in conjunction with CAR-T cells. In some embodiments, the ENPP1 inhibitor compound may be administered before or after administration of CAR-T cells.

Single Therapy

Myocardial Regeneration Promotion Therapy

In one aspect, the myocardial regeneration therapy may include administering a therapeutically effective amount of an ENPP1 inhibitor to a subject having a lesion due to myocardial infarction to treat the subject.

Hypophosphatemia Treatment Regimen

In one aspect, hypophosphatemia treatment methods may include administering a therapeutically effective amount of an ENPP1 inhibitor to a subject having a lesion caused by a genetic hypophosphatemia disease to treat the subject.

Pharmaceutical Composition

Pharmaceutically acceptable excipients such as vehicles, adjuvants, carriers or diluents are easily obtainable to those skilled in the art. Pharmaceutically acceptable auxiliary substances such as pH modifiers, buffers, isotonicity modifiers, stabilizers, wetting agents and the like are easily obtainable by those skilled in the art.

In some embodiments, the compound of the present invention is formulated in an aqueous buffer. Suitable aqueous buffers include, but are not limited to, acetate, succinate, citrate and phosphate buffers at various concentrations ranging from 5 mM to 1,000 mM. In some embodiments, aqueous buffers include reagents that provide isotonic solutions. Such reagents include, but are not limited to, sodium chloride, sugars such as mannitol, dextrose, and sucrose, and the like. In some embodiments, the aqueous buffer further includes a nonionic surfactant such as polysorbate 20 or 80. Optionally, the formulation may further include a preservative. Suitable preservatives include, but are not limited to, benzyl alcohol, phenol, chlorobutanol, benzalkonium chloride, and the like. In another embodiment, the formulation is stored at about 4° C. The formulation may also be lyophilized and generally contains a cryoprotectant such as sucrose, trehalose, lactose, maltose, or mannitol. Freeze-dried preparations may be stored even at room temperature for a long period of time.

Here, the pharmaceutical composition may include or essentially consist of the compound disclosed herein, or a pharmaceutically acceptable salt thereof, an isomer thereof, or a tautomer thereof, and further includes or essentially consists of one or more activators of interest. Any beneficial activator may be used in the present method in combination with the compound of the present invention. In one embodiment, the compound of the present invention and the immune checkpoint inhibitor, as well as the additional therapeutic agent as described herein for combination therapy, may be administered orally, subcutaneously, intramuscularly, intranasally, parenterally or via other routes. In another embodiment, the compound of the present invention, the chemotherapeutic agent (especially a chemotherapeutic agent capable of inducing cGAMP production in vivo), and the additional therapeutic agent described herein for combination therapy may be administered orally, subcutaneously, intramuscularly, intranasally, parenterally or by other routes. The compound of the present invention and the second activator (if present) may be administered via identical or different routes. The therapeutic agent may be administered by any suitable means including, but not limited to, oral, rectal, nasal, topical, vaginal, parenteral, intravenous, intranasal, and intratumoral injection into the organ affected.

The compounds of the present invention may be administered in a unit dosage form and may be prepared by any method well known in the art. Such methods include combining the compound of the present invention with a pharmaceutically acceptable carrier or diluent which constitutes one of one or more auxiliary ingredients. The pharmaceutically acceptable carrier is selected based on the selected route of administration and standard pharmaceutical practice. Each carrier should be "pharmaceutically acceptable" in that it is compatible with the other ingredients of the formulation and does not harm the subject or patient. This carrier may be solid or liquid, the type of which is generally selected according to the route of administration.

Examples of suitable solid carriers include lactose, sucrose, gelatin, agar and bulk powder. Examples of suitable liquid carriers include water, pharmaceutically acceptable fats and oils, alcohols or other organic solvents such as esters, emulsions, syrups or elixirs, suspensions and solutions and/or suspensions reconstituted from non-foaming granules. Such liquid carriers may contain, for example, suitable solvents, preservatives, emulsifiers, suspending agents, diluents, sweetening agents, thickeners and melting agents.

Hereinafter, various aspects of the present invention will be described.

In one aspect, the present invention provides a compound selected from a naphthyridinone derivative compound represented by the following Formula 1, a pharmaceutically acceptable salt thereof, a hydrate thereof, a solvate thereof and a stereoisomer thereof:

[Formula 1]

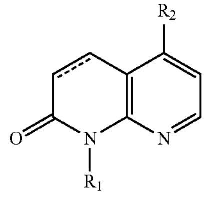

wherein $R_1$ is hydrogen, a $C_1$-$C_{13}$ alkyl group, or a $C_3$-$C_{10}$ cyclic group;

$R_2$ is —Z—$R_3$—$(R_4)_m$;

Z is present or absent, wherein when Z is present, Z is —O—, —CO—, —COO—, —$C_nH_{n+2}$—, —O($C_nH_{n+2}$)—, —$(OC_2H_4)_n$—, —$(C_2H_4O)_n$—, —($C_nH_{n+2}$)O—, —($C_nH_{n+2}$)CO—, —($C_nH_{n+2}$)O($C_mH_{m+2}$)—, —$NR_6$($C_nH_{n+2}$)—, —$(NR_6C_2H_4)_n$—, —$(C_2H_4NR_6)_n$—, or —($C_nH_{n+2}$)$NR_6$—;

n is an integer from 0 to 8;

$R_3$ is a $C_3$-$C_{10}$ cyclic group, a $C_3$-$C_{10}$ heterocyclic group, a $C_6$-$C_{10}$ aryl group, or a $C_3$-$C_{10}$ heteroaryl group;

$R_4$ is hydrogen, a hydroxyl group, a halogen group, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclic group, a $C_3$-$C_{10}$ heteroaryl group, a $C_3$-$C_{10}$ heterocyclic group, —C(O)—($C_1$-$C_{13}$ alkyl), a tert-butyloxycarbonyl group (Boc), an amino group (—$NR_5R_6$), —($C_mH_{m+2}$)$NR_5R_6$, a nitro group (—$N(O)_2$), an amide group (—(C═O)$NR_5R_6$), an ester group (—C(O)$OR_6$), a carboxylic group (—C(O)OH), a nitrile group (—CN), a sulfonamide group (—$NHS(O)_2R_6$), a urea group, a sulfamoyl group (—$NHS(O)_2NHR_6$), a sulfonamide group, a sulfamoylalkyl group (—($C_mH_{m+2}$)$NHS(O)_2NHR_6$), a sulfamoylalkyl group (—($C_mH_{m+2}$)$NR_5S(O)_2NHR_6$), a sulfide group (—$SR_6$), a sulfone group (—$S(O)_2R_6$), or a phosphoryl group (—P(O)$R_5R_6$), or is bonded to the same carbon as the carbon bonded to $R_3$ to form a 3- to 7-membered saturated ring, is bonded to the same carbon as the carbon bonded to $R_3$ to form a 3- to 7-membered saturated heterocycle containing at least one heteroatom of N, O and S, is bonded to the carbon adjacent to the carbon bonded to $R_3$ to form a 3- to 7-membered saturated ring, or is bonded to the carbon adjacent to the carbon bonded to $R_3$ to form a 3- to 7-membered saturated heterocycle containing at least one heteroatom of N, O and S; and m is an integer from 1 to 4;

wherein the $C_1$-$C_6$ alkyl group, the $C_1$-$C_{13}$ alkyl group or the $C_3$-$C_{10}$ cyclic group includes at least one substituent selected from the group consisting of hydrogen, a hydroxyl group, a halogen group, a $C_1$-$C_{13}$ alkyl group, a $C_1$-$C_6$ alkoxy group, an amino group (—$NR_5R_6$), a nitro group (—$N(O)_2$), an amide group (—(C═O)$NR_5R_6$), a carboxylic group (—C(O)OH), a nitrile group (—CN), a urea group (—$NR_5$(C═O)$NR_6$—), a sulfonamide group (—$NHS(O)_2$—), a sulfide group (—S—), a sulfonyl group (—$S(O)_2$—), a phosphoryl group (—P(O) $R_5R_6$), a $C_6$-$C_{10}$ aryl group, a $C_3$-$C_{10}$ heteroaryl group, and a $C_3$-$C_{10}$ heterocyclic group, and the $C_6$-$C_{10}$ aryl group, the $C_3$-$C_{10}$ heteroaryl group or the $C_3$-$C_{10}$ heterocyclic group includes at least one substituent selected from the group consisting of hydrogen, a hydroxyl group, a halogen group, a carbonyl group (—(C═O)$R_5R_6$), a $C_1$-$C_3$ alkyl group substituted or unsubstituted with halogen or a $C_3$-$C_{10}$ heterocyclic group, a $C_1$-$C_3$ alkoxy group substituted or unsubstituted with halogen or a $C_3$-$C_{10}$ heterocyclic group, $C_6$-$C_{10}$ phenoxy, an amino group (—$NR_5R_6$), a nitro group (—$N(O)_2$), an amide group (—(C═O) $NR_5R_6$), a carboxylic group (—C(O)OH), a nitrile group (—CN), a urea group (—$NR_5$(C—O)$NR_6$—), a sulfonamide group (—$NHS(O)_2$—), a sulfide group (—S—), a sulfonyl group (—$S(O)_2$—), a phosphoryl group (—P(O)$R_5R_6$), a $C_6$-$C_{10}$ aryl group, a $C_3$-$C_{10}$ heteroaryl group and a $C_3$-$C_{10}$ heterocyclic group; and $R_5$ and $R_6$ are each independently hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, a $C_3$-$C_{10}$ heterocyclic group, or $R_5$, together with a nitrogen or carbon atom bonded to $R_6$, forms a 3- to 7-membered saturated ring, which includes at least one of N, O, S, NH, C═N, C═O, —NHC(O)—, —NHC(O)NH—, —$NHS(O)_2$—, or $SO_2$, and is substituted with at least one of hydrogen, a $C_1$-$C_{13}$ alkyl group, a $C_6$-$C_{10}$ aryl group, a $C_3$-$C_1$a heteroaryl group, a hydroxyl group, a halide group or a cyano group, wherein the $C_3$-$C_{10}$ heteroaryl group and the $C_3$-$C_{10}$ heterocyclic group include at least one heteroatom selected from the group consisting of N, O, and S.

In the definition of a substituent in the present invention, the term "alkyl" means an aliphatic hydrocarbon radical. Alkyl may be "saturated alkyl" containing no alkenyl or alkynyl moiety, or "unsaturated alkyl" containing at least one alkenyl or alkynyl moiety. The term "alkenyl" means a group containing at least one carbon-carbon double bond, and the term "alkynyl" means a group containing at least one carbon-carbon triple bond. The alkyl may be cyclic, branched or straight-chain when used alone or in combination.

The term "aryl" means a $C_6$ aromatic monocarbocyclic group which may be further fused, singly or in combination with another radical, with a 5- or 6-membered carbocyclic group which may be aromatic, and may be saturated or unsaturated. Examples of the aryl may include, but are not limited to, phenyl, indanyl, 1-naphthyl, 2-naphthyl, tetrahydronaphthyl, and the like. Aryl may be linked with other groups at appropriate positions on the aromatic ring.

The term "alkoxy" refers to an alkyl group linked to another group through an oxygen atom (i.e., —O-alkyl). The alkoxy group may be unsubstituted or substituted with one or more suitable substituents. Examples of the alkoxy group include, but are not limited to, a ($C_1$-$C_6$)alkoxy group, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-butyl, —O-2-ethyl-1-butyl, —O-butyl, —O-isobutyl, —O-t-butyl, —O-pentyl, —O-isopentyl, —O-neopentyl and —O-hexyl.

The term "phenoxy" refers to a phenyl group linked to another group through an oxygen atom (i.e., —O-aryl). The phenoxy is unsubstituted or substituted with at least one of halogen, alkyl, aryl or heteroaryl group, but is not limited thereto.

The term "amine group" refers to an alkyl group linked to another group through a nitrogen atom (i.e., —NH— or —N-alkyl). The amine group may be unsubstituted or substituted with one or more suitable substituents. Examples of the amine group include, but are not limited to, ($C_1$-$C_6$) amino, for example, —NH-methyl, —NH-ethyl, —NH-propyl, —NH-isopropyl, —NH-2-methyl-1-propyl, —NH-2-methyl-2-propyl, —NH-2-methyl-1-butyl, —NH-3-methyl-1-butyl, —NH-2-methyl-3-butyl, —NH-2,2-dimethyl-1-propyl, —NH-2-methyl-1-pentyl, 3-NH-methyl-1-pentyl, —NH-4-methyl-1-pentyl, —NH-2-methyl-2-pentyl, —NH-3-methyl-2-pentyl, —NH-4-methyl-2-pentyl, —NH-2,2-dimethyl-1-butyl, —NH-3,3-dimethyl-butyl, —NH-2-ethyl-1-butyl, —NH-butyl, —NH-isobutyl, —NH-t-butyl, —NH-pentyl, —NH-isopentyl, —NH-neopentyl, —NH-hexyl, —N,N-dimethyl, —N-methyl-N-ethyl, —N-methyl-N-propyl, —N-methyl-isopropyl, —N-methyl-N-butyl, —N-methyl-N-isobutyl, —N-methyl-N-pentyl, —N-methyl-N-isopentyl, N-methyl-N-hexyl, N-methyl-N-isohexyl, —N,N-diethyl, —N-ethyl-N-propyl, —N-ethyl-N-isopropyl, —N-ethyl-N-butyl, —N-ethyl-N-isobutyl, —N-ethyl-N-pentyl, —N-ethyl-N-isopentyl, —N-ethyl-N-hexyl, —N-ethyl-N-isohexyl, —N,N-dipropyl, —N-propyl-N-isopropyl, —N-propyl-N-butyl, —N-propyl-N-isobutyl, —N-propyl-N-pentyl, —N-propyl-N-isopentyl, —N-propyl-N-hexyl, —N-propyl-N-isohexyl, —N,N-dibutyl, —N-butyl-N-isobutyl, —N-butyl-N-pentyl, —N-butyl-N-isopentyl, —N-butyl-N-hexyl, —N-butyl-N-isohexyl, —N,N-dipentyl, —N-pentyl-N-hexyl, —N-pentyl-N-isohexyl, and —N,N-dihexyl.

The term "halogen group" means fluorine, chlorine, bromine or iodine.

The term "heterocyclic group" means a heteroaromatic compound containing at least one heteroatom selected from the group consisting of N, O, and S, unless otherwise mentioned. Preferably, the heterocyclic group may include, without being limited to, pyrrolidine, furan, morpholine, piperazine and piperidine groups, more preferably pyrrolidine, piperidine, piperazine and morpholine groups.

The term "heteroaryl group" refers to a heteroaromatic compound containing at least one heteroatom selected from the group consisting of N, O, and S, unless otherwise mentioned. Preferably, the heteroaryl group may include, without being limited to, pyridine, pyrazine, pyrimidine, pyridazine, pyrazole, imidazole, triazole, indole, oxadiazole, thiadiazole, quinoline, isoquinoline, isoxazole, oxazole, thiazole and pyrrole groups.

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein $R_1$ is hydrogen or a $C_1$-$C_5$ alkyl group, $R_3$ is a $C_5$-$C_7$ heterocyclyl group, a $C_6$-$C_8$ aryl group, or a $C_5$-$C_{10}$ heteroaryl group.

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein $R_1$ is hydrogen or a $C_1$-$C_3$ alkyl group, and $R_3$ is substituted or unsubstituted benzene, substituted or unsubstituted hexane, substituted or unsubstituted furan, substituted or unsubstituted thiophene, substituted or unsubstituted pyridine, substituted or unsubstituted benzofuran, substituted or unsubstituted naphthalene, substituted or unsubstituted anthracene, or substituted or unsubstituted phenanthrene, substituted or unsubstituted pyridazine, substituted or unsubstituted piperidine, substituted or unsubstituted morpholine, substituted or unsubstituted pyrrolidine, substituted or unsubstituted pyrazine, substituted or unsubstituted imidazole, substituted or unsubstituted pyrazole, substituted or unsubstituted quinoline, substituted or unsubstituted pyrimidine, substituted or unsubstituted pyrrole, substituted or unsubstituted indole, substituted or unsubstituted purine, substituted or unsubstituted cyclopropane, or substituted or unsubstituted cyclobutene.

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein $R_1$ is hydrogen or a $C_1$-$C_3$ alkyl group, and $R_3$ is substituted or unsubstituted benzene, or substituted or unsubstituted piperidine.

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein $R_2$ is

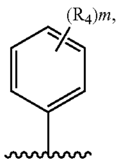
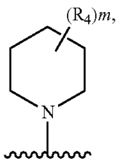
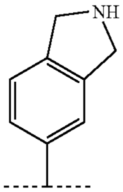
,
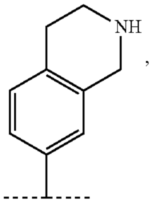
,
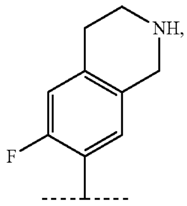
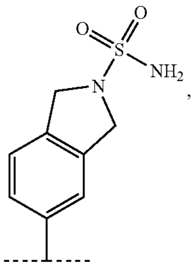
,
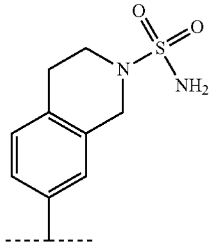
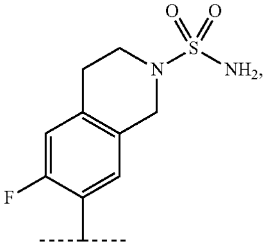
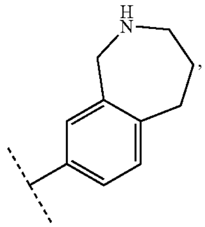
,
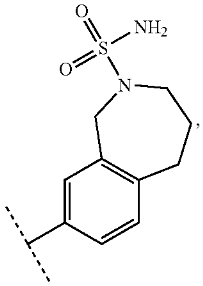
,
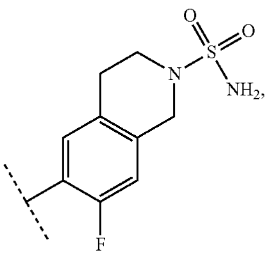
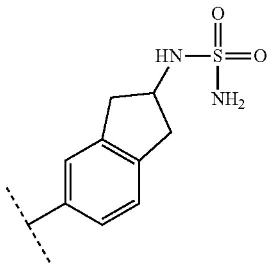
,
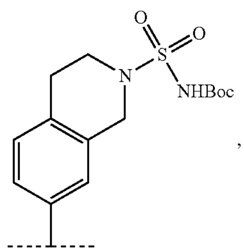
,
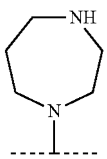
,
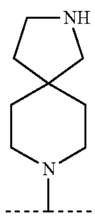
, -continued

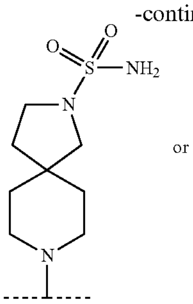

or

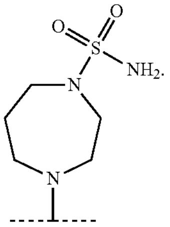

-continued

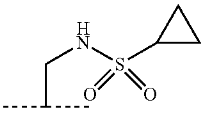

,

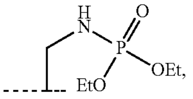

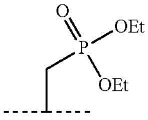

,

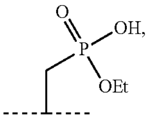

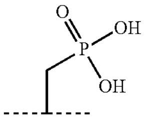

or

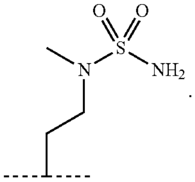

.

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein $R_4$ is halogen, a methyl group, an ethyl group, $-NH_2$, $-CH_2NH_2$, $-CHCH_3NH_2$, $-CH(CH_3)_2NH_2$, $-CHCH_3NHCH_3$, $-CH_2NHCH_2CH_3$, -tert-butyloxycarbonyl group (Boc),

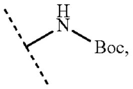

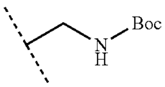

,

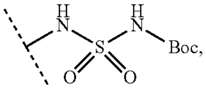

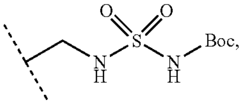

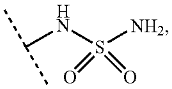

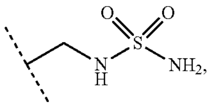

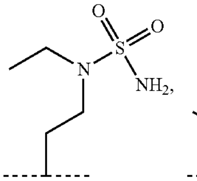

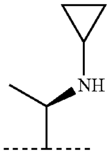

,

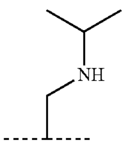

,

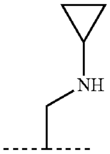

,

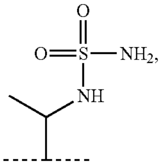

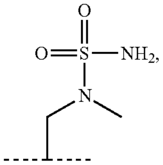

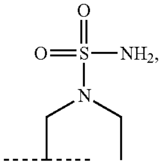

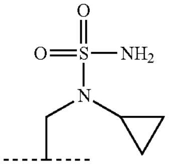

,

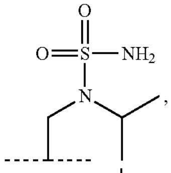

,

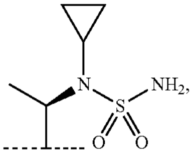

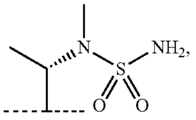

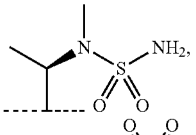

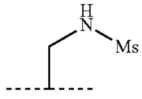

,

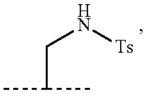

,

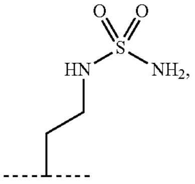

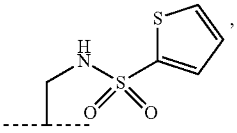

,

In one aspect, the present invention provides a compound selected from a naphthyridinone derivative compound represented by Formula 1, a pharmaceutically acceptable salt thereof, a hydrate thereof, a solvate thereof and a stereoisomer thereof, wherein the compound is selected from the group consisting of the following Compounds Nos. 1 to 148:

Selected Compounds:

Compound No. 1: tert-butyl(3-(7-oxo-7,8-dihydro-1,8-naphthyridin-4-yl)phenyl)carbamate;

Compound No. 2: tert-butyl(3-(7-oxo-7,8-dihydro-1,8-naphthyridin-4-yl)benzyl)carbamate;

Compound No. 3: tert-butyl(4-(7-oxo-7,8-dihydro-1,8-naphthyridin-4-yl)benzyl)carbamate;

Compound No. 4: tert-butyl(2-fluoro-4-(7-oxo-7,8-dihydro-1,8-naphthyridin-4-yl)benzyl)carbamate;

Compound No. 5: tert-butyl(4-(8-methyl-7-oxo-7,8-dihydro-1,8-naphthyridin-4-yl)benzyl)carbamate;

Compound No. 6: 5-(3-(aminophenyl)-1,8-naphthyridin-2(1H)-one hydrochloride;

Compound No. 7: 5-(3-(aminomethyl)phenyl)-1,8-naphthyridin-2(1H)-one hydrochloride;

Compound No. 8: 5-(5-(amino-2-fluorophenyl)-1,8-naphthyridin-2(1H)-one hydrochloride;

Compound No. 9: 5-(3-(aminomethyl)-4-fluorophenyl)-1,8-naphthyridin-2(1H)-one hydrochloride;

Compound No. 10: 5-(4-(aminomethyl)phenyl)-1,8-naphthyridin-2(1H)-one hydrochloride;

Compound No. 11: 5-(4-(aminomethyl)-2-fluorophenyl)-1,8-naphthyridin-2(1H)-one hydrochloride;

Compound No. 12: 5-(4-(aminomethyl)-3-fluorophenyl)-1,8-naphthyridin-2(1H)-one hydrochloride;

Compound No. 13: 5-(4-(aminomethyl)-2,3-difluorophenyl)-1,8-naphthyridin-2(1H)-one hydrochloride;

Compound No. 14: 5-(4-(1-aminoethyl)phenyl)-1,8-naphthyridin-2(1H)-one hydrochloride;

Compound No. 15: (R)-5-(4-(1-aminoethyl)phenyl)-1,8-naphthyridin-2(1H)-one hydrochloride;

Compound No. 16: 5-(4-(2-aminopropan-2-yl)phenyl)-1,8-naphthyridin-2(1B)-one hydrochloride;

Compound No. 17: (R)-5-(4-(1-(methylaminoethyl)phenyl)-1,8-naphthyridin-2(1H)-one hydrochloride;

Compound No. 18: (S)-5-(4-(1-(methylaminoethyl)phenyl)-1,8-naphthyridin-2(1H)-one hydrochloride;

Compound No. 19: (R)-5-(4-(1-(cyclopropylaminoethyl)phenyl)-1,8-naphthyridin-2(1H)-one hydrochloride;

Compound No. 20: 5-(4-((ethylamino)methyl)-2-fluorophenyl)-1,8-naphthyridin-2(1H)-one hydrochloride;

Compound No. 21: 5-(2-fluoro-4-((isopropylamine)methyl)phenyl)-1,8-naphthyridin-2(1H)-one hydrochloride;

Compound No. 22: 5-(4-((cyclopropylamino)methyl)-2-fluorophenyl)-1,8-naphthyridin-2(1H)-one hydrochloride;

Compound No. 23: 5-(3-fluoro-4-((methylamino)methyl)phenyl)-1,8-naphthyridin-2(1H)-one hydrochloride;

Compound No. 24: 5-(4-((ethylamino)methyl)-3-fluorophenyl)-1,8-naphthyridin-2(1H)-one hydrochloride;

Compound No. 25: 5-(4-((cyclopropylamino)methyl)-3-fluorophenyl)-1,8-naphthyridin-2(1H)-one hydrochloride;

Compound No. 26: 5-(isoindolin-5-yl)-1,8-naphthyridin-2(1H)-one hydrochloride;

Compound No. 27: 5-(1,2,3,4-tetrahydroisoquinolin-7-yl)-1,8-naphthyridin-2(1H)-one hydrochloride;

Compound No. 28: 5-(6-fluoro-1,2,3,4-tetrahydroisoquinolin-7-yl)-1,8-naphthyridin-2(1H)-one hydrochloride;

Compound No. 29: 5-(4-(aminomethyl)phenyl)-1-methyl-1,8-naphthyridin-2(1H)-one hydrochloride;

Compound No. 30: tert-butyl(N-(3-(7-oxo-7,8-dihydro-1,8-naphthyridin-4-yl)phenyl)sulfamoyl)carbamate;

Compound No. 31: tert-butyl(N-(3-(7-oxo-7,8-dihydro-1,8-naphthyridin-4-yl)benzyl)sulfamoyl)carbamate;

Compound No. 32: tert-butyl(N-(4-(7-oxo-7,8-dihydro-1,8-naphthyridin-4-yl)benzyl)sulfamoyl)carbamate;

Compound No. 33: tert-butyl(N-(2-fluoro-4-(7-oxo-7,8-dihydro-1,8-naphthyridin-4-yl)benzyl)sulfamoyl)carbamate;

Compound No. 34: tert-butyl(N-(4-(8-methyl-7-oxo-7,8-dihydro-1,8-naphthyridin-4-yl)benzyl)sulfamoyl)carbamate;

Compound No. 35: N-(3-(7-oxo-7,8-dihydro-1,8-naphthyridin-4-yl)phenyl)sulfamide;

Compound No. 36: N-(2-fluoro-5-(7-oxo-7,8-dihydro-1,8-naphthyridin-4-yl)phenyl)sulfamide hydrochloride;

Compound No. 37: N-(3-(7-oxo-7,8-dihydro-1,8-naphthyridin-4-yl)benzyl)sulfamide;

Compound No. 38: N-(2-fluoro-5-(7-oxo-7,8-dihydro-1,8-naphthyridin-4-yl)benzyl)sulfamide hydrochloride;

Compound No. 39: N-(4-(7-oxo-7,8-dihydro-1,8-naphthyridin-4-yl)phenyl)sulfamide;

Compound No. 40: N-(4-(7-oxo-7,8-dihydro-1,8-naphthyridin-4-yl)benzyl)sulfamide;

Compound No. 41: N-(2-fluoro-4-(7-oxo-7,8-dihydro-1,8-naphthyridin-4-yl)benzyl)sulfamide;

Compound No. 42: N-(3-fluoro-4-(7-oxo-7,8-dihydro-1,8-naphthyridin-4-yl)benzyl)sulfamide hydrochloride;

Compound No. 43: N-(2,3-difluoro-4-(7-oxo-7,8-dihydro-1,8-naphthyridin-4-yl)benzyl)sulfamide hydrochloride;

Compound No. 44: N-(3,5-difluoro-4-(7-oxo-7,8-dihydro-1,8-naphthyridin-4-yl)benzyl)sulfamide hydrochloride;

Compound No. 45: N-(1-(4-(7-oxo-7,8-dihydro-1,8-naphthyridin-4-yl)phenyl)ethyl)sulfamide hydrochloride;

Compound No. 46: (R)-(N-(1-(4-(7-oxo-7,8-dihydro-1,8-naphthyridin-4-yl)phenyl)ethyl)sulfamide hydrochloride;

Compound No. 47: (S)-(N-(1-(4-(7-oxo-7,8-dihydro-1,8-naphthyridin-4-yl)phenyl)ethyl)sulfamide hydrochloride;

Compound No. 48: (R)-(N-(1-(2-fluoro-4-(7-oxo-7,8-dihydro-1,8-naphthyridin-4-yl)phenyl)ethyl)sulfamide hydrochloride;

Compound No. 49: (R)-(N-(1-(3-fluoro-4-(7-oxo-7,8-dihydro-1,8-naphthyridin-4-yl)phenyl)ethyl)sulfamide hydrochloride;

Compound No. 50: N-methyl-N-(4-(7-oxo-7,8-dihydro-1,8-naphthyridin-4-yl)benzyl)sulfamide hydrochloride;

Compound No. 51: N-ethyl-N-(4-(7-oxo-7,8-dihydro-1,8-naphthyridin-4-yl)benzyl)sulfamide hydrochloride;

Compound No. 52: N-(2-fluoro-4-(7-oxo-7,8-dihydro-1,8-naphthyridin-4-yl)benzyl)-N-methylsulfamide hydrochloride;

Compound No. 53: N-ethyl-N-(2-fluoro-4-(7-oxo-7,8-dihydro-1,8-naphthyridin-4-yl)benzyl)sulfamide hydrochloride;

Compound No. 54: N-cyclopropyl-N-(2-fluoro-4-(7-oxo-7,8-dihydro-1,8-naphthyridin-4-yl)benzyl)sulfamide hydrochloride;

Compound No. 55: N-(3-fluoro-4-(7-oxo-7,8-dihydro-1,8-naphthyridin-4-yl)benzyl)-N-methylsulfamide hydrochloride;

Compound No. 56: N-ethyl-N-(3-fluoro-4-(7-oxo-7,8-dihydro-1,8-naphthyridin-4-yl)benzyl)sulfamide hydrochloride;

Compound No. 57: N-(3-fluoro-4-(7-oxo-7,8-dihydro-1,8-naphthyridin-4-yl)benzyl)-N-isopropyl)sulfamide hydrochloride;

Compound No. 58: N-cyclopropyl-N-(3-fluoro-4-(7-oxo-7,8-dihydro-1,8-naphthyridin-4-yl)benzyl)sulfamide hydrochloride;

Compound No. 59: (R)-(N-methyl-N-(1-(4-(7-oxo-7,8-dihydro-1,8-naphthyridin-4-yl)phenyl)ethyl)sulfamide hydrochloride;

Compound No. 60: (R)-(N-cyclopropyl-N-(1-(4-(7-oxo-7,8-dihydro-1,8-naphthyridin-4-yl)phenyl)ethyl)sulfamide hydrochloride;

Compound No. 61: (S)-(N-methyl-N-(1-(4-(7-oxo-7,8-dihydro-1,8-naphthyridin-4-yl)phenyl)ethyl)sulfamide hydrochloride;

Compound No. 62: (R)-(N-(1-(2-fluoro-4-(7-oxo-7,8-dihydro-1,8-naphthyridin-4-yl)phenyl)ethyl)sulfamide hydrochloride;

Compound No. 63: (R)-(N-(1-(3-fluoro-4-(7-oxo-7,8-dihydro-1,8-naphthyridin-4-yl)phenyl)ethyl)sulfamide hydrochloride;

Compound No. 64: 5-(7-oxo-7,8-dihydro-1,8-naphthyridin-4-yl)isoindolin-2-yl)sulfamide hydrochloride;

Compound No. 65: 7-(7-oxo-7,8-dihydro-1,8-naphthyridin-4-yl)dihydroisoquinoline-2(1H)-sulfamide hydrochloride;

Compound No. 66: 6-fluoro-7-(7-oxo-7,8-dihydro-1,8-naphthyridin-4-yl)-3,4-dihydroisoquinoline-2(1H)-sulfamide hydrochloride;

Compound No. 67: N-(4-(8-methyl-7-oxo-7,8-dihydro-1,8-naphthyridin-4-yl)benzyl)sulfamide;

Compound No. 68: N-(4-(7-oxo-7,8-dihydro-1,8-naphthyridin-4-yl)benzyl)methanesulfonamide;

Compound No. 69: 4-methyl-N-(4-(7-oxo-7,8-dihydro-1,8-naphthyridin-4-yl)benzyl)benzenesulfonamide;

Compound No. 70: N-(4-(7-oxo-7,8-dihydro-1,8-naphthyridin-4-yl)benzyl)thiophene-2-sulfonamide;

Compound No. 71: N-(4-(7-oxo-7,8-dihydro-1,8-naphthyridin-4-yl)benzyl)cyclopropanesulfonamide;

Compound No. 72: diethyl(4-(7-oxo-7,8-dihydro-1,8-naphthyridin-4-yl)benzyl)phosphonate;

Compound No. 73: diethyl(4-(7-oxo-7,8-dihydro-1,8-naphthyridin-4-yl)benzyl)phosphoamidate;

Compound No. 74: ethylhydrogen(4-(7-oxo-7,8-dihydro-1,8-naphthyridin-4-yl)benzyl)phosphonate;

Compound No. 75: (4-(7-oxo-7,8-dihydro-1,8-naphthyridin-4-yl)benzyl)phosphonic acid;

Compound No. 76: 5-((3-aminophenyl)amino)-1,8-naphthyridin-2(1H)-one dihydrochloride;

Compound No. 77: 5-((3-aminomethyl)phenyl)amino)-1,8-naphthyridin-2(1H)-one dihydrochloride;

Compound No. 78: 5-((3-aminomethyl)-4-fluorophenyl)amino)-1,8-naphthyridin-2(1H)-one dihydrochloride;

Compound No. 79: 5-((5-(2-aminoethyl)-2-fluorophenyl)amino)-1,8-naphthyridin-2(1H)-one dihydrochloride;

Compound No. 80: 5-((3-(2-methylphenylethyl)phenyl)amino)-1,8-naphthyridin-2(1H)-one dihydrochloride;

Compound No. 81: 5-((4-aminophenyl)amino)-1,8-naphthyridin-2(1H)-one dihydrochloride;

Compound No. 82: 5-((4-(aminomethyl)phenyl)amino)-1,8-naphthyridin-2(1H)-one dihydrochloride;

Compound No. 83: 5-((4-((cyclopropylamino)methyl)phenyl)amino)-1,8-naphthyridin-2(1H)-one dihydrochloride;

Compound No. 84: 5-((4-((cyclopropylamino)methyl)phenyl)amino)-1,8-naphthyridin-2(1H)-one dihydrochloride;

Compound No. 85: 5-((1,2,3,4-tetrahydroisoquinolin-6-yl)amino)-1,8-naphthyridin-2(1H)-one dihydrochloride;

Compound No. 86: 5-((7-fluoro-1,2,3,4-tetrahydroisoquinolin-6-yl)amino)-1,8-naphthyridin-2(1H)-one dihydrochloride;

Compound No. 87: 5-((2,3,4,5-tetrahydro-1H-benzo[c]azepin-8-yl)amine)-1,8-naphthyridin-2(1H)-one dihydrochloride;

Compound No. 88: N-(3-((7-oxo-7,8-dihydro-1,8-naphthyridin-4-yl)amino)phenyl)sulfamide dihydrochloride;

Compound No. 89: N-(3-((7-oxo-7,8-dihydro-1,8-naphthyridin-4-yl)amino)benzyl)sulfamide dihydrochloride;

Compound No. 90: N-(2-fluoro-5((7-oxo-7,8-dihydro-1,8-naphthyridin-4-yl)amino)benzyl)sulfamide dihydrochloride;

Compound No. 91: N-(4-fluoro-3-((7-oxo-7,8-dihydro-1,8-naphthyridin-4-yl)amino)benzyl)sulfamide dihydrochloride;

Compound No. 92: N-(3-((7-oxo-7,8-dihydro-1,8-naphthyridin-4-yl)amino)phenethyl)sulfamide dihydrochloride;

Compound No. 93: N-methyl-N-(3-((7-oxo-7,8-dihydro-1,8-naphthyridin-4-yl)amino)phenethyl)sulfamide dihydrochloride;

Compound No. 94: N-ethyl-N-(3-((7-oxo-7,8-dihydro-1,8-naphthyridin-4-yl)amino)phenethyl)sulfamide dihydrochloride;

Compound No. 95: N-(4-fluoro-3-((7-oxo-7,8-dihydro-1,8-naphthyridin-4-yl)amino)phenethyl)sulfamide dihydrochloride;

Compound No. 96: N-(4-fluoro-3-((7-oxo-7,8-dihydro-1,8-naphthyridin-4-yl)amino)phenethyl)-N-methylsulfamide dihydrochloride;

Compound No. 97: N-(4-((7-oxo-7,8-dihydro-1,8-naphthyridin-4-yl)amino)phenyl)sulfamide dihydrochloride;

Compound No. 98: N-(4-((7-oxo-7,8-dihydro-1,8-naphthyridin-4-yl)amino)benzyl)sulfamide dihydrochloride;

Compound No. 99: N-cyclopropyl-N-(4-((7-oxo-7,8-dihydro-1,8-naphthyridin-4-yl)amino)benzyl)sulfamide dihydrochloride;

Compound No. 100: N-(3-chloro-4-((7-oxo-7,8-dihydro-1,8-naphthyridin-4-yl)amino)benzyl)sulfamide dihydrochloride;

Compound No. 101: 5-((7-oxo-7,8-dihydro-1,8-naphthyridin-4-yl)amino)isoindolin-2-yl)sulfamide dihydrochloride;

Compound No. 102: 7-((7-oxo-7,8-dihydro-1,8-naphthyridin-4-yl)amino)-3,4-dihydroisoquinolin-2(1H)-yl)sulfamide dihydrochloride;

Compound No. 103: (8-((7-oxo-7,8-dihydro-1,8-naphthyridin-4-yl)amino)-1,3,4,5-tetrahydro-2 (1H)-benzo[c]azepin-2-yl)sulfamide dihydrochloride;

Compound No. 104: (6-((7-oxo-7,8-dihydro-1,8-naphthyridin-4-yl)amino)-3,4-dihydroisoquinolin-2(1H)-yl)sulfamide dihydrochloride;

Compound No. 105: 6-fluoro-7-((7-oxo-7,8-dihydro-1,8-naphthyridin-4-yl)amino)-3,4-dihydroisoquinolin-2(1H)-yl)sulfamide dihydrochloride;

Compound No. 106: (7-fluoro-6-((7-oxo-7,8-dihydro-1,8-naphthyridin-4-yl)amino)-3,4-dihydroisoquinolin-2(1H)-yl)sulfamide dihydrochloride;

Compound No. 107: N-(5-((7-oxo-7,8-dihydro-1,8-naphthyridin-4-yl)amino)-2,3-dihydro-1H-inden-2-yl)sulfamide dihydrochloride;

Compound No. 108: (7-(methyl (7-oxo-7,8-dihydro-1,8-naphthyridin-4-yl)amino)-3,4-dihydroisoquinolin-2(1H)-yl) sulfamide dihydrochloride;

Compound No. 109: tert-butyl(1-(7-oxo-7,8-dihydro-1,8-naphthyridin-4-yl)piperidin-4-yl)carbamate;

Compound No. 110: tert-butyl((1-(7-oxo-7,8-dihydro-1,8-naphthyridin-4-yl)piperidin-4-yl)methyl)carbamate;

Compound No. 111: tert-butyl(2-(1-(7-oxo-7,8-dihydro-1,8-naphthyridin-4-yl)piperidin-4-yl)ethyl)carbamate;

Compound No. 112: tert-butyl((1-(8-methyl-7-oxo-7,8-dihydro-1,8-naphthyridin-4-yl)piperidin-4-yl)methyl)carbamate;

Compound No. 113: 5-(4-aminopiperidin-1-yl)-1,8-naphthyridin-2(1H)-one hydrochloride;

Compound No. 114: 5-(4-(aminomethyl)piperidin-1-yl)-1,8-naphthyridin-2(1H)-one hydrochloride;

Compound No. 115: 5-(4-(2-aminoethyl)piperidin-1-yl)-1,8-naphthyridin-2(1H)-one hydrochloride;

Compound No. 116: 5-(1,4-diazepan-1-yl)-1,8-naphthyridin-2(1H)-one hydrochloride;

Compound No. 117: 5-(2,8-diazaspiro[4,5]decan-8-yl)-1,8-naphthyridin-2(1H)-one hydrochloride;

Compound No. 118: 5-(4-(aminomethyl)piperidin-1-yl)-1-methyl-1,8-naphthyridin-2(1H)-one hydrochloride;

Compound No. 119: tert-butyl(N-(1-(7-oxo-7,8-dihydro-1,8-naphthyridin-4-yl)piperidin-4-yl)sulfamoyl)carbamate;

Compound No. 120: tert-butyl(N-((1-(7-oxo-7,8-dihydro-1,8-naphthyridin-4-yl)piperidin-4-yl)methyl)sulfamoyl)carbamate;

Compound No. 121: tert-butyl(N-(2-(1-(7-oxo-7,8-dihydro-1,8-naphthyridin-4-yl)piperidin-4-yl)ethyl) sulfamoyl)carbamate;

Compound No. 122: tert-butyl(N-((1-(8-methyl-7-oxo-7,8-dihydro-1,8-naphthyridin-4-yl)piperidin-4-yl)methyl)sulfamoyl)carbamate;

Compound No. 123: N-(1-(7-oxo-7,8-dihydro-1,8-naphthyridin-4-yl)piperidin-4-yl)sulfamide;

Compound No. 124: N-((1-(7-oxo-7,8-dihydro-1,8-naphthyridin-4-yl)piperidin-4-yl)methyl)sulfamide;

Compound No. 125: N-(2-(1-(7-oxo-7,8-dihydro-1,8-naphthyridin-4-yl)piperidin-4-yl)ethyl)sulfamide;

Compound No. 126: 8-(7-oxo-7,8-dihydro-1,8-naphthyridin-4-yl)-2,8-diazaspiro[4,5]decane-2-sulfamide;

Compound No. 127: 8-(7-oxo-7,8-dihydro-1,8-naphthyridin-4-yl)-2,8-diazaspiro[4,5]decane-2-sulfamide;

Compound No. 128: N-((1-(8-methyl-7-oxo-7,8-dihydro-1,8-naphthyridin-4-yl)piperidin-4-yl)methyl)sulfamide;

Compound No. 129: tert-butyl(3-(7-oxo-5,6,7,8-tetrahydro-1,8-naphthyridin-4-yl)benzyl)carbamate;

Compound No. 130: tert-butyl(4-(7-oxo-5,6,7,8-tetrahydro-1,8-naphthyridin-4-yl)benzyl)carbamate;

Compound No. 131: 5-(3-(aminophenyl)-3,4-dihydro-1,8-naphthyridin-2(1H)-one hydrochloride;

Compound No. 132: 5-(3-(aminomethyl)phenyl)-3,4-dihydro-1,8-naphthyridin-2(1H)-one hydrochloride;

Compound No. 133: 5-(4-(aminomethyl)phenyl)-3,4-dihydro-1,8-naphthyridin-2(1H)-one hydrochloride;

Compound No. 134: 5-(4-(2-aminopropan-2-yl)phenyl)-3,4-dihydro-1,8-naphthyridin-2(1H)-one hydrochloride;

Compound No. 135: 5-(1,2,3,4-tetrahydroisoquinolin-7-yl)-3,4-dihydro-1,8-naphthyridin-2(1H)-one hydrochloride;

Compound No. 136: tert-butyl(N-(3-(7-oxo-5,6,7,8-tetrahydro-1,8-naphthyridin-4-yl)benzyl)sulfamoyl)carbamate;

Compound No. 137: tert-butyl(N-(4-(7-oxo-5,6,7,8-tetrahydro-1,8-naphthyridin-4-yl)benzyl)sulfamoyl)carbamate;

Compound No. 138: tert-butyl((7-(7-oxo-5,6,7,8-tetrahydro-1,8-naphthyridin-4-yl)-3,4-diisoquinolin-2 (1H)-yl) sulfonyl) carbamate;

Compound No. 139: N-(3-(7-oxo-5,6,7,8-tetrahydro-1,8-naphthyridin-4-yl)phenyl)sulfamide;

Compound No. 140: N-(3-(7-oxo-5,6,7,8-tetrahydro-1,8-naphthyridin-4-yl)benzyl)sulfamide;

Compound No. 141: N-(4-(7-oxo-5,6,7,8-tetrahydro-1,8-naphthyridin-4-yl)benzyl)sulfamide;

Compound No. 142: N-(2-fluoro-4-(7-oxo-5,6,7,8-tetrahydro-1,8-naphthyridin-4-yl)benzyl)sulfamide;

Compound No. 143: 5-(7-oxo-5,6,7,8-tetrahydro-1,8-naphthyridin-4-yl)isoindoline-2-sulfamide hydrochloride Compound No. 144: (7-(7-oxo-5,6,7,8-tetrahydro-1,8-naphthyridin-4-yl)amino)-3,4-dihydroisoquinoline-2(1H)-sulfamide hydrochloride;

Compound No. 145: (7-(7-oxo-5,6,7,8-tetrahydro-1,8-naphthyridin-4-yl)-3,4-dihydroisoguinolin-2(1H)-yl)sulfamide hydrochloride;

Compound No. 146: N-(3-(7-oxo-5,6,7,8-tetrahydro-1,8-naphthyridin-4-yl)benzyl)methanesulfonamide;

Compound No. 147: 4-methyl-N-(3-(7-oxo-5,6,7,8-tetrahydro-1,8-naphthyridin-4-yl)benzyl)benzenesulfonamide; and Compound No. 148: N-(3-(7-oxo-5,6,7,8-tetrahydro-1,8-naphthyridin-4-yl)benzyl)thiophene-2-sulfonamide.

The compound of Formula 1 according to the present invention may be used in the form of a pharmaceutically acceptable salt derived from an inorganic or organic acid and the pharmaceutically acceptable salt preferably includes at least one selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

The compound of Formula 1 according to the present invention or a pharmaceutically acceptable salt thereof may include a hydrate and a solvate. The hydrate may be formed by bonding the compound of Formula 1 to a water molecule.

In another aspect, the present invention provides a pharmaceutical composition for preventing, alleviating or treating cancer containing the compound according to one aspect of the present invention as an active ingredient.

In another aspect, the present invention provides an ENPP 1 inhibitor containing the compound according to one aspect of the present invention as an active ingredient.

In another aspect, the present invention provides a STING pathway activator containing the compound according to one aspect of the present invention as an active ingredient.

In another aspect, the present invention provides a pharmaceutical composition for preventing, alleviating or treating cancer wherein the cancer is associated with inhibition of ENPP 1.

In another aspect, the present invention provides a pharmaceutical composition for preventing, alleviating or treating cancer, containing the compound selected from the compound of Formula 1 according to the present invention, the pharmaceutically acceptable salt thereof, the hydrate thereof or the stereoisomer thereof as an active ingredient.

The pharmaceutical composition according to the present invention has excellent ability to inhibit the activity of ENPP 1.

Therefore, the pharmaceutical composition of the present invention may be used for the treatment, prevention and alleviation of cancer diseases caused by abnormal cell growth. The cancer diseases that can be prevented, treated or alleviated by administration of the pharmaceutical composition of the present invention include gastric cancer, lung cancer, liver cancer, colorectal cancer, small intestine cancer, pancreatic cancer, brain cancer, bone cancer, melanoma, breast cancer, sclerosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, myelodysplastic syndrome), lymphoma (including Hodgkin's disease and non-Hodgkin's lymphoma), psoriasis, and fibroadenoma.

In another aspect, the present invention provides an ENPP 1 inhibitor containing any one of the compounds described above as an active ingredient.

In another aspect, the present invention provides a STING pathway activator containing any one of the compounds described above as an active ingredient.

The pharmaceutical composition may be applied to experimental animals such as mice, rabbits, rats, guinea pigs or hamsters, preferably primates including humans, more preferably humans, without being limited thereto.

As used herein, the term "treatment" includes alleviating or ameliorating symptoms, reducing the extent of a disease, delaying or alleviating disease progression, ameliorating, alleviating, or stabilizing a disease condition, partial or complete recovery, prolonging survival, and other beneficial treatment results.

In addition, as used herein, treatment of cancer means treatment of all cancer cells, and the cancer includes angiogenesis of endothelial cells and mitosis thereof (solid tumors, tumor metastasis, and benign tumors). For example, the cancer includes, but is not limited to, breast cancer, ovarian cancer, cervical cancer, prostate cancer, testicular cancer, genitourinary cancer, esophageal cancer, laryngeal cancer, glioblastoma, stomach cancer, skin cancer, keratoacanthomas, lung cancer, squamous cell carcinoma, large cell carcinoma, small cell carcinoma, lung adenocarcinoma, bone cancer, colon cancer, adenoma, pancreatic cancer, adenocarcinoma, carcinogenic cancer, follicular carcinoma, undifferentiated cancer, papillary cancer, normal hematoma, melanoma, sarcoma, bladder cancer, liver cancer, bile duct cancer, kidney cancer, myeloid diseases, lymphoid diseases, Hodgkin's disease, hair cell cancer, oral cavity cancer, pharyngeal (oral) cancer, lip cancer, tongue cancer, small intestine cancer, colorectal cancer, colon cancer, rectal cancer, brain cancer, central nervous system cancer, leukemia, hemangioma, trachoma, and purulent sarcoma.

The content of the active ingredient, namely, the compound represented by Formula 1, the pharmaceutically acceptable salt thereof, the hydrate thereof, or the solvate thereof is appropriately adjusted through selection by those skilled in the art depending on the use mode and use method of the pharmaceutical composition of the present invention.

For example, the pharmaceutical composition contains the compound represented by Formula 1, the pharmaceutically acceptable salt thereof, the hydrate thereof, or the solvate thereof in an amount of 0.1 to 10% by weight, more preferably 0.5 to 5% by weight, based on the total weight of the pharmaceutical composition.

The compound represented by Formula 1, the pharmaceutically acceptable salt thereof, the hydrate thereof, or the solvate thereof may be present alone or in combination with a pharmacologically acceptable carrier, excipient, diluent, or an accessory ingredient in the pharmaceutical composition.

For example, the pharmaceutically acceptable carrier, excipient, and diluent include, but are not limited to, one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, dextrin, calcium carbonate, propylene glycol, liquid paraffin, and physiological saline, and a common carrier, excipient, or diluent may be used. In addition, the pharmaceutical composition may further include a conventional filler, extender, binder, disintegrating agent, anticoagulant, lubricant, wetting agent, pH adjusting agent, nutrient, vitamin, electrolyte, alginic acid or a salt thereof, pectic acid or a salt thereof, protective colloid, glycerin, fragrance, emulsifier, preservative, or the like.

When administered in combination with another anticancer drug for treating cancer or tumors, the compound represented by Formula 1 or the pharmaceutically acceptable salt thereof can exert a synergistic therapeutic effect with the anticancer drug.

Specifically, the pharmaceutical composition may further include at least one other anti-cancer agent or therapeutic agent known to be effective for treating or preventing cancer, in addition to the active ingredient, and thus may be used as a simultaneously or separately applied combination therapy. Other anti-cancer agents or therapeutic agents that may be applied to combination therapy may include, for example, at least one compound selected from the group consisting of Gleevec® (imatinib), Sutent® (sunitinib), Herceptin® (trastuzumab), Velcade® (bortezomib), dexamethasone, Nexavar® (sorafenib), aromatase inhibitors, and kinase inhibitors, but are not limited thereto.

The pharmaceutical composition may be administered orally or parenterally, and for example, may be administered through various routes including oral, transdermal, subcutaneous, intravenous, or intramuscular routes. In addition, the formulation of the composition may vary depending on the method of use, and may be formulated using methods well known in the art to provide rapid, sustained, or delayed release of the active ingredient after administration to mammals. In general, solid preparations for oral administration include tablets, troches, soft or hard capsules, pills, powders, granules, and the like. These preparations can be prepared, for example, by mixing starch, calcium carbonate, sucrose, lactose, gelatin, or the like. In addition, lubricants such as magnesium stearate and talc may also be used, in addition to simple excipients. Liquid preparations for oral administration include suspensions, liquids and solutions, emulsions, syrups, and the like. In addition to water and liquid paraffin, which are common simple diluents, various excipients such as wetting agents, sweeteners, fragrances, and preservatives may be included. Formulations for parenteral administration include creams, lotions, ointments, plasters, liquids and solutions, aerosols, fluid extracts, elixirs, infusions, sachets, patches, injections, and the like. Injection formulations are preferably in the form of an isotonic aqueous solution or suspension.

The pharmaceutical composition may further include an adjuvant such as a sterilizer, a preservative, a stabilizer, a hydrating agent or an emulsifying accelerator, a salt and/or a buffer for controlling osmotic pressure, and other therapeutically useful substances. Alternatively, the pharmaceutical composition may be formulated in accordance with an ordinary mixing, granulation, or coating method or using a suitable method known in the art.

In addition, the dosage of the pharmaceutical composition may be determined in consideration of the administration method, the age, gender, disease severity, and condition of the patient, the rate of absorption of the active ingredient in the body, and the inactivation rate of the active ingredient and drugs used in combination therewith, and the pharmaceutical composition may be administered once or multiple times in a portionwise manner. The active ingredient of the pharmaceutical composition is preferably orally or parenterally administered to a mammal including a human in an amount of 0.001 to 100 mg/kg body weight, preferably 0.01 to 35 mg/kg body weight, on a daily basis, and may be administered once or divided into multiple administrations throughout the day.

In another aspect, the present invention provides a method of treating cancer including administering a therapeutically effective amount of the compound represented by Formula 1, the pharmaceutically acceptable salt thereof, or the hydrate thereof.

Preferably, the treatment method may further include identifying a patient in need of prevention or treatment of cancer before the administration.

As used herein, the term "therapeutically effective amount" means an amount of an active ingredient which is effective for the prevention or treatment of cancer in a mammal, and the therapeutically effective amount may be controlled by a variety of factors such as the type of disease, the severity of the disease, the type and content of the active ingredient and other ingredients contained in the composition, the type of formulation, the age, weight, general state of health, gender, and diet of the patient, the time of administration, the route of administration, clearance rate of the composition in blood, the duration of treatment, and drugs used simultaneously therewith. Preferably, as described above, the compound may be administered in an amount of 0.001 to 100 mg/kg body weight, preferably 0.01 to 35 mg/kg body weight, on a daily basis, once or multiple times in a portionwise manner a day, by oral or parenteral routes.

In another aspect, the present invention provides a method of preparing a compound selected from the naphthyridinone derivative compound represented by Formula 1, the pharmaceutically acceptable salt thereof, the hydrate thereof and the stereoisomer thereof.

Meanwhile, the present invention provides a method for preparing the naphthyridinone derivative compound represented by Formula 1. The preparation method according to the present invention will be described in detail as follows.

In one embodiment, the compound represented by Formula 1 according to the present invention may be prepared by at least one of the following Preparation Methods 1 to 4.

Preparation Method 1

The naphthyridinone derivative compound of Formula 1 according to one aspect of the present invention may be prepared in accordance with the preparation method based on the following Reaction Scheme 1.

[Reaction Scheme 1]
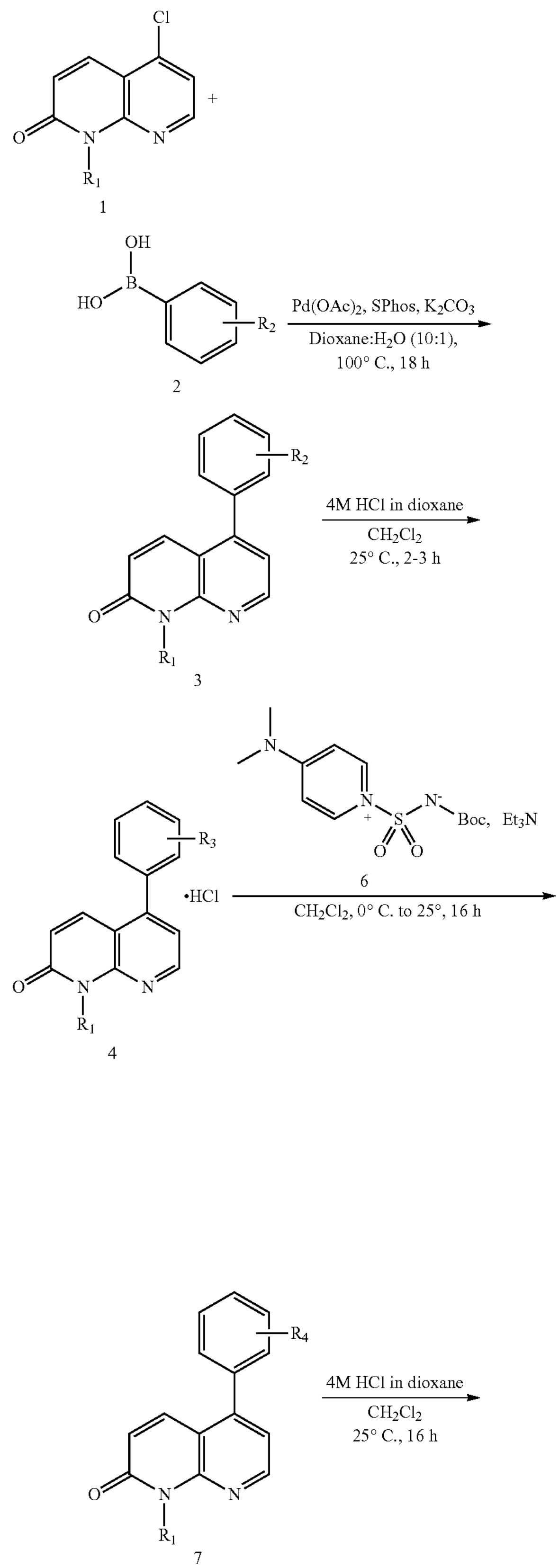
1
2
3
6
4
7
-continued
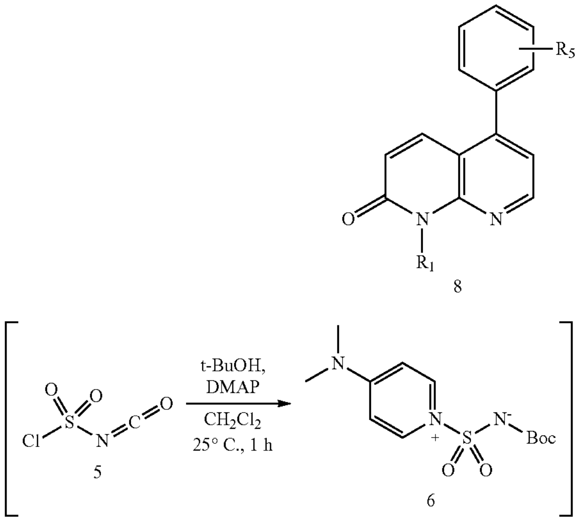
8
5
6
Preparation Method 2
The naphthyridinone derivative compound of Formula 1 according to one aspect of the present invention may be prepared in accordance with the preparation method based on the following Reaction Scheme 2.
[Reaction Scheme 2]
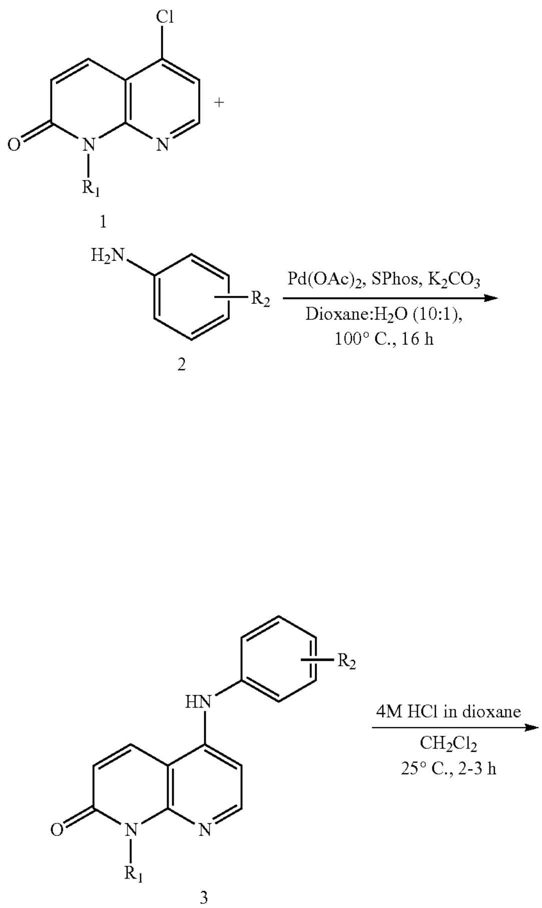
1
2
3

-continued
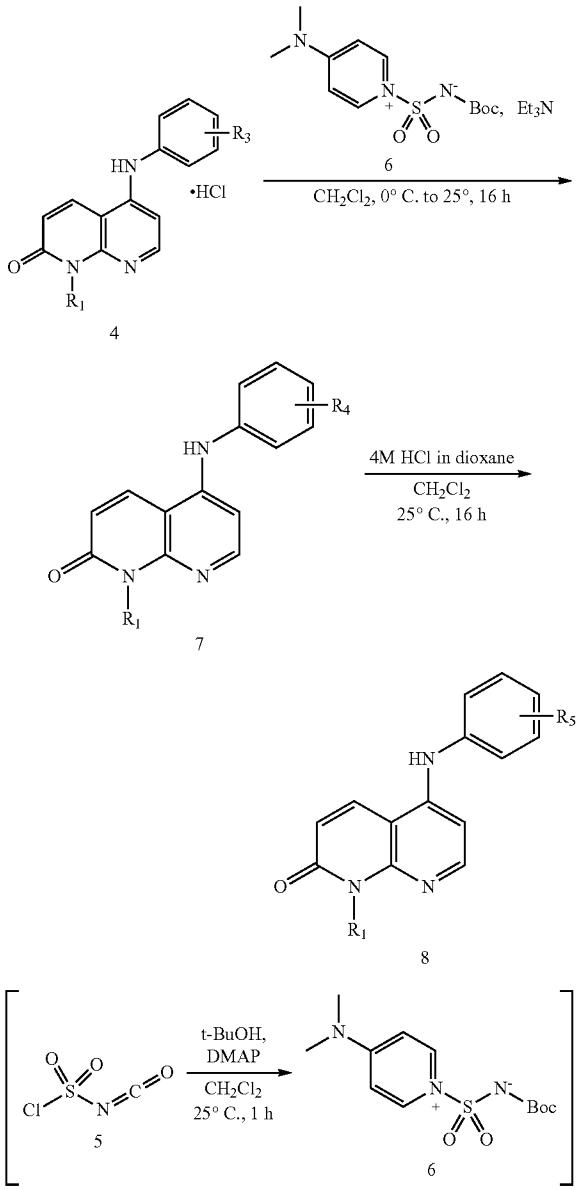
4
7
8
5
6
Preparation Method 3
The naphthyridinone derivative compound of Formula 1 according to one aspect of the present invention may be prepared in accordance with the preparation method based on the following Reaction Scheme 3.
[Reaction Scheme 3]
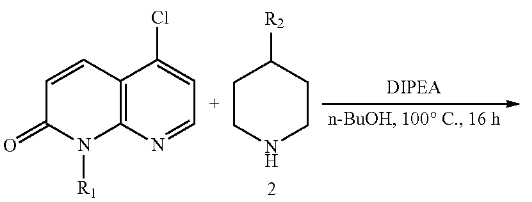
1
2
-continued
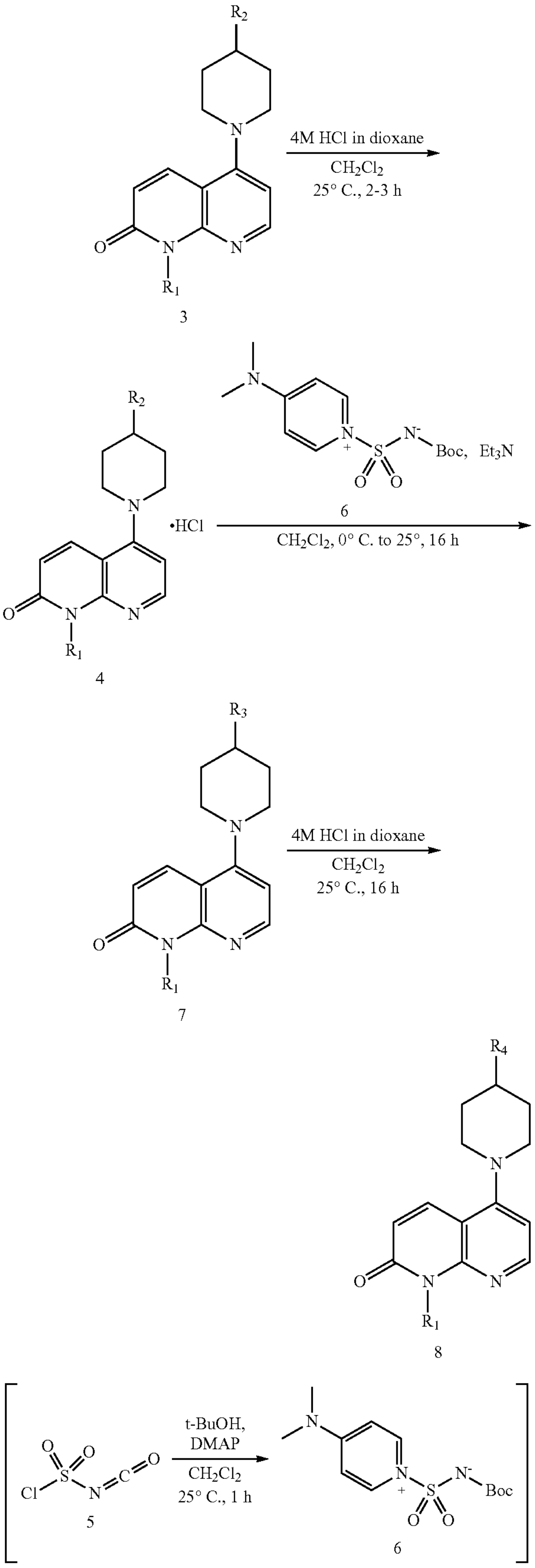
3
4
7
8
5
6

Preparation Method 4

The naphthyridinone derivative compound of Formula 1 according to one aspect of the present invention may be prepared in accordance with the preparation method based on the following Reaction Scheme 4.

[Reaction Scheme 4]

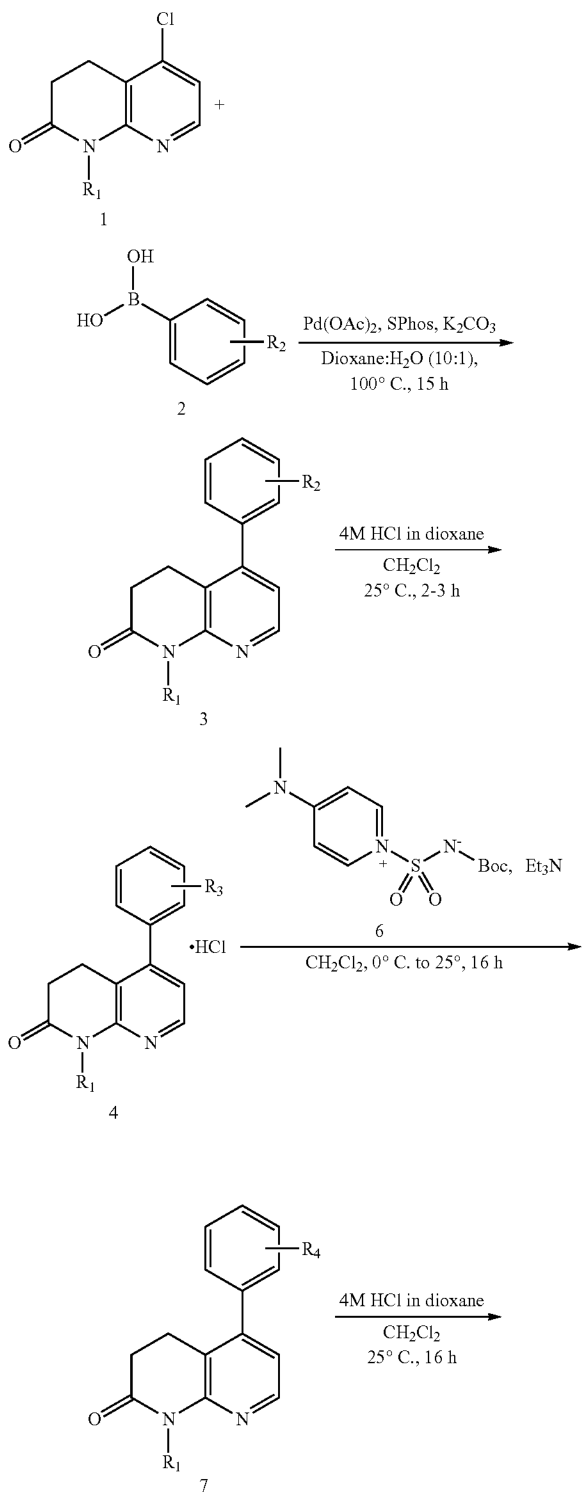

-continued

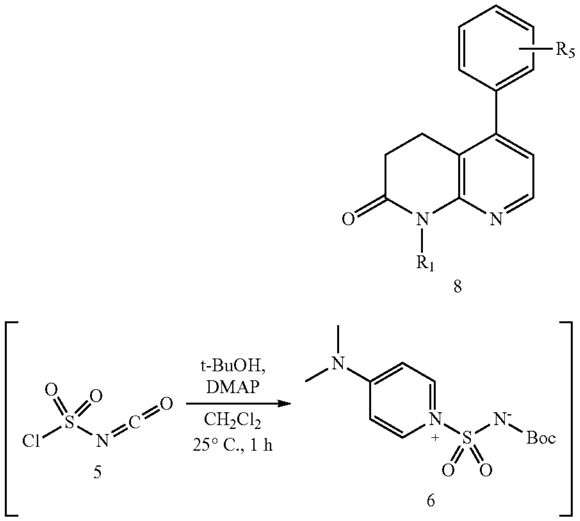

MODE FOR INVENTION

Hereinafter, the present invention will be described in more detail with reference to Synthesis Examples, Preparation Examples, Examples, Experimental examples and Formulation Examples. However, the following Synthesis Examples, Preparation Examples, Examples, Experimental examples and Formulation Examples are provided only for illustration and should not be construed as limiting the scope of the present invention.

Preparation Example 1

Preparation Example 1 includes a process of preparing Product 3, Product 4, Product 7 or Product 8.

Preparation Example 1

[Reaction Scheme 1]

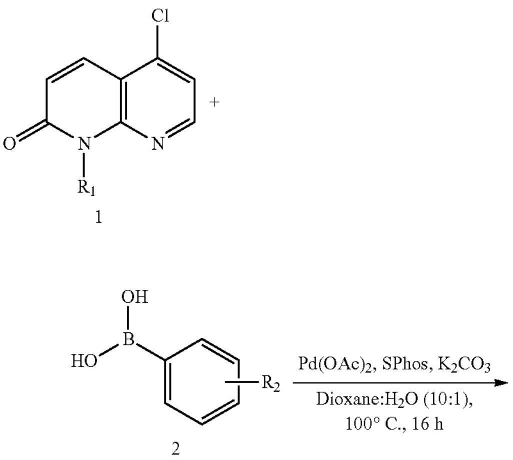

-continued

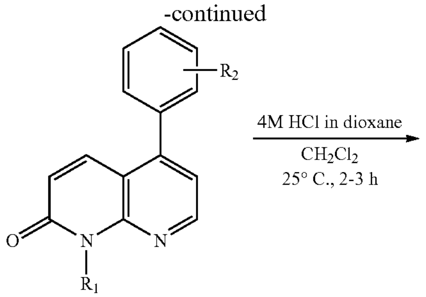

3

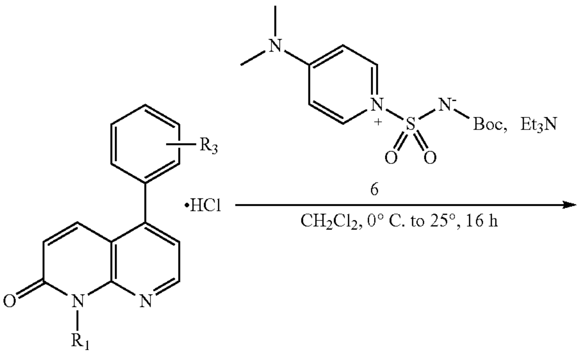

4

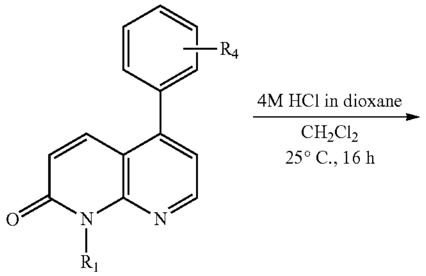

7

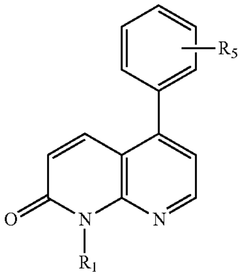

8

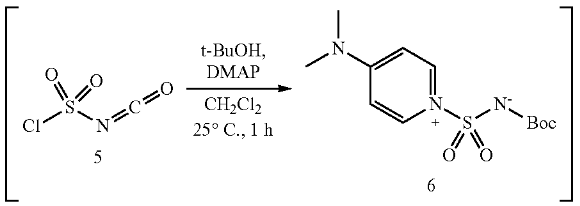

5

6

Step 1: 1 (1.0 equiv.), palladium(II) acetate (0.050 equiv.), 2-dicyclohexylphosphino-2',6'-dimethoxybiphenyl (0.10 equiv.), 2 (1.3 equiv.) and potassium carbonate (3.0 equiv.) were dissolved in 1,4-dioxane (0.090 M) and water (0.90 M) in a round bottom flask and refluxed under nitrogen for 16 hours. After the reaction was completed, the mixture was filtered through celite, poured into water, and extracted with dichloromethane. The organic layer was dried over anhydrous magnesium sulfate and concentrated under reduced pressure. The resulting residue was purified by column chromatography (1:20 MeOH:$CH_2Cl_2$) to obtain 3 (40-60% yield).

The Examples of the present invention prepared according to step 1 as described above are as follows.

[Example 1]: tert-butyl(3-(7-oxo-7,8-dihydro-1,8-naphthyridin-4-yl)phenyl)carbamate

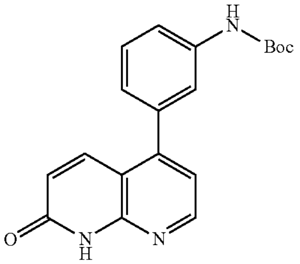 [SMILES: CC(C)(C)OC(=O)Nc1cccc(-c2ccnc3[nH]c(=O)ccc23)c1]

$^1$H NMR (400 MHz, MeOD-$d_4$) δ 8.57 (d, J=4.9 Hz, 1H), 7.99 (d, J=9.8 Hz, 1H), 7.59 (s, 1H), 7.54 (d, J=8.3 Hz, 1H), 7.45 (t, J=7.9 Hz, 1H), 7.25 (d, J=4.9 Hz, 1H), 7.11 (d, J=7.6 Hz, 1H), 6.65 (d, J=9.7 Hz, 1H), 1.52 (s, 9H).

[Example 2]: tert-butyl(3-(7-oxo-7,8-dihydro-1,8-naphthyridin-4-yl)benzyl)carbamate

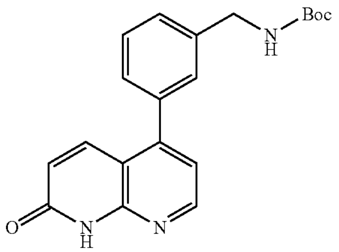 [SMILES: CC(C)(C)OC(=O)NCc1cccc(-c2ccnc3[nH]c(=O)ccc23)c1]

$^1$H NMR (400 MHz, MeOD-d4) δ 8.58 (d, J=4.9 Hz, 1H), 7.96 (d, J=9.7 Hz, 1H), 7.53 (t, J=7.6 Hz, 1H), 7.45 (d, J=7.7 Hz, 1H), 7.38 (d, J=9.8 Hz, 2H), 7.24 (d, J=5.0 Hz, 1H), 6.63 (d, J=9.8 Hz, 1H), 4.33 (s, 2H), 1.45 (s, 9H).

[Example 3]: tert-butyl(4-(7-oxo-7,8-dihydro-1,8-naphthyridin-4-yl)benzyl)carbamate

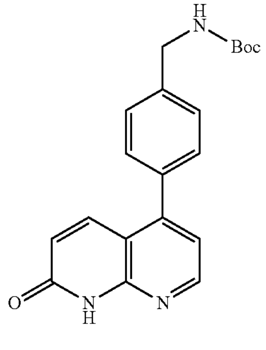 [SMILES: CC(C)(C)OC(=O)NCc1ccc(-c2ccnc3[nH]c(=O)ccc23)cc1]

$^1$H NMR (400 MHz, MeOD-d4) δ 8.57 (d, J=4.9 Hz, 1H), 7.96 (d, J=9.7 Hz, 1H), 7.50-7.44 (m, 4H), 7.24 (d, J=4.9 Hz, 1H), 6.64 (d, J=9.8 Hz, 1H), 4.34 (s, 2H), 1.47 (s, 9H).

[Example 4]: tert-butyl(2-fluoro-4-(7-oxo-7,8-dihydro-1,8-naphthyridin-4-yl)benzyl)carbamate

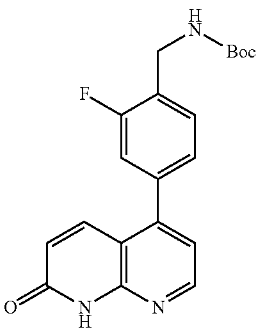 [SMILES: CC(C)(C)OC(=O)NCc1ccc(-c2ccnc3[nH]c(=O)ccc23)cc1F]

$^1$H NMR (400 MHz, DMSO-$d_6$) δ 8.55 (d, J=4.9 Hz, 1H), 7.76 (d, J=9.8 Hz, 1H), 7.53-7.44 (m, 2H), 7.40-7.29 (m, 2H), 7.21 (d, J=5.0 Hz, 1H), 6.56 (d, J=9.8 Hz, 1H), 4.26 (d, J=6.1 Hz, 2H), 1.41 (s, 9H).

[Example 5]: tert-butyl(4-(8-methyl-7-oxo-7,8-dihydro-1,8-naphthyridin-4-yl)benzyl)carbamate

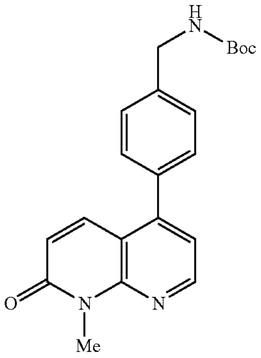 [SMILES: Cn1c(=O)ccc2c(-c3ccc(CNC(=O)OC(C)(C)C)cc3)ccnc21]

$^1$H NMR (400 MHz, DMSO-$d_6$) δ 8.67 (d, J=4.9 Hz, 1H), 7.76 (d, J=9.8 Hz, 1H), 7.49 (t, J=6.3 Hz, 1H), 7.47-7.39 (m, 4H), 7.27 (d, J=4.9 Hz, 1H), 6.68 (d, J=9.8 Hz, 1H), 4.23 (d, J=6.2 Hz, 2H), 3.73 (s, 3H), 1.41 (s, 9H).

Step 2: 3 (1.0 equiv.) was dissolved in dichloromethane (0.040 M) in a round bottom flask. Then, a hydrochloride solution (4.0 M in 1,4-dioxane, 0.2 M) was added thereto, followed by stirring at room temperature for 4 hours. After the reaction was completed, the reaction mixture was concentrated under reduced pressure residue, was washed with diethyl ether, filtered and dried to obtain 4 (60-80% yield).

[Example 6]: 5-(3-(aminophenyl)-1,8-naphthyridin-2(1H)-one hydrochloride

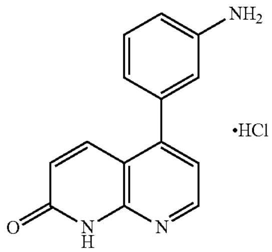 [SMILES: Nc1cccc(-c2ccnc3[nH]c(=O)ccc23)c1 ; Cl]

$^1$H NMR (400 MHz, MeOD-d4) δ 8.63 (d, J=4.9 Hz, 1H), 7.89 (d, J=9.8 Hz, 1H), 7.76 (t, J=7.9 Hz, 1H), 7.64 (d, J=7.6 Hz, 1H), 7.56 (d, J=8.3 Hz, 1H), 7.49 (d, J=2.1 Hz, 1H), 7.27 (d, J=4.9 Hz, 1H), 6.67 (d, J=9.8 Hz, 1H).

[Example 7]: 5-(3-(aminomethyl)phenyl)-1,8-naphthyridin-2(1H)-one hydrochloride

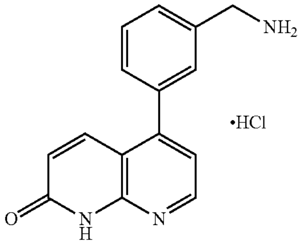 [SMILES: NCc1cccc(-c2ccnc3[nH]c(=O)ccc23)c1 ; Cl]

$^1$H NMR (400 MHz, MeOD-d4) δ 8.66 (d, J=5.1 Hz, 1H), 8.01 (d, J=9.7 Hz, 1H), 7.72-7.65 (m, 2H), 7.64-7.58 (m, 2H), 7.35 (d, J=5.2 Hz, 1H), 6.74 (d, J=9.5 Hz, 1H).

[Example 8]: 5-(5-(amino-2-fluorophenyl)-1,8-naphthyridin-2(1H)-one hydrochloride

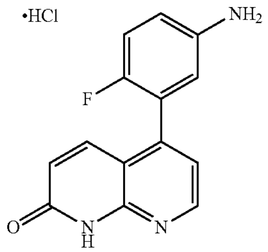 [SMILES: Nc1ccc(F)c(-c2ccnc3[nH]c(=O)ccc23)c1 ; Cl]

$^1$H NMR (400 MHz, DMSO-$d_6$) δ 12.37 (s, 1H), 8.62 (d, J=4.9 Hz, 1H), 7.54 (dd, J=9.8, 2.6 Hz, 1H), 7.48 (d, J=9.2 Hz, 1H), 7.30 (d, J=3.7 Hz, 1H), 7.23 (d, J=4.9 Hz, 1H), 6.59 (d, J=9.8 Hz, 1H), 5.33 (s, 4H).

[Example 9]: 5-(3-(aminomethyl)-4-fluorophenyl)-1,8-naphthyridin-2(1H)-one hydrochloride

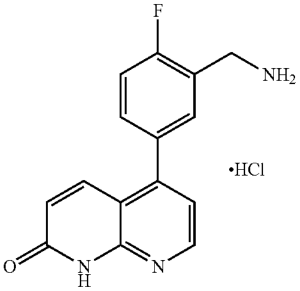 [SMILES: NCc1cc(-c2ccnc3[nH]c(=O)ccc23)ccc1F ; Cl]

$^1$H NMR (400 MHz, DMSO-$d_6$) δ 12.32 (s, 1H), 8.59 (d, J=4.9 Hz, 4H), 7.87 (d, J=9.8 Hz, 1H), 7.78 (dd, J=7.0, 1.9 Hz, 1H), 7.64-7.55 (m, 1H), 7.56-7.46 (m, 1H), 7.23 (d, J=4.9 Hz, 1H), 6.58 (d, J=9.8 Hz, 1H), 4.16 (d, J=5.6 Hz, 2H).

[Example 10]: 5-(4-(aminomethyl)phenyl)-1,8-naphthyridin-2(1H)-one hydrochloride

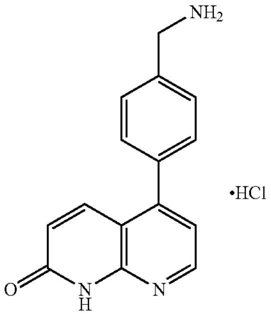 [SMILES: NCc1ccc(-c2ccnc3[nH]c(=O)ccc23)cc1 ; Cl]

$^1$H NMR (400 MHz, MeOD-d4) δ 8.63 (d, J=5.0 Hz, 1H), 7.93 (d, J=9.7 Hz, 1H), 7.67 (d, J=8.0 Hz, 2H), 7.63-7.59 (m, 2H), 7.29 (d, J=5.0 Hz, 1H), 6.70 (d, J=9.7 Hz, 1H), 4.25 (s, 2H).

[Example 11]: 5-(4-(aminomethyl)-2-fluorophenyl)-1,8-naphthyridin-2(1H)-one hydrochloride

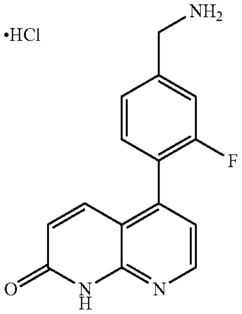 [SMILES: Cl ; NCc1ccc(-c2ccnc3[nH]c(=O)ccc23)c(F)c1]

$^1$H NMR (400 MHz, DMSO-$d_6$) δ 12.37 (s, 1H), 8.61 (d, J=4.9 Hz, 3H), 7.65 (d, J=10.4 Hz, 1H), 7.61-7.51 (m, 2H), 7.45 (dd, J=9.7, 2.7 Hz, 1H), 7.22 (d, J=4.9 Hz, 1H), 6.61 (d, J=9.8 Hz, 1H), 4.16 (q, J=5.6 Hz, 2H)

[Example 12]: 5-(4-(aminomethyl)-3-fluorophenyl)-1,8-naphthyridin-2(1H)-one hydrochloride

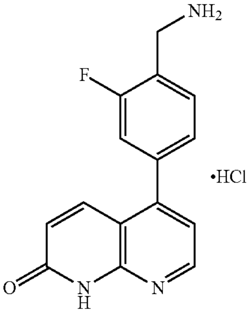 [SMILES: NCc1ccc(-c2ccnc3[nH]c(=O)ccc23)cc1F ; Cl]

$^1$H NMR (400 MHz, MeOD-d4) δ 8.65 (d, J=5.1 Hz, 1H), 7.94 (d, J=9.7 Hz, 1H), 7.72 (t, J=7.7 Hz, 1H), 7.50-7.41 (m, 2H), 7.32 (d, J=5.0 Hz, 1H), 6.74 (d, J=9.7 Hz, 1H), 4.32 (s, 2H).

[Example 13]: 5-(4-(aminomethyl)-2,3-difluorophenyl)-1,8-naphthyridin-2(1H)-one hydrochloride

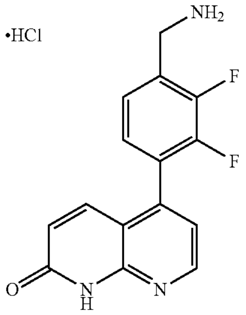 [SMILES: Cl ; NCc1ccc(-c2ccnc3[nH]c(=O)ccc23)c(F)c1F]

$^1$H NMR (400 MHz, DMSO-$d_6$) δ 12.41 (s, 1H), 8.64 (d, J=4.9 Hz, 4H), 7.67-7.57 (m, 1H), 7.50 (d, J=1.9 Hz, 1H), 7.43 (dd, J=8.1, 4.6 Hz, 1H), 7.26 (d, J=4.9 Hz, 1H), 6.63 (d, J=9.8 Hz, 1H), 4.22 (d, J=5.6 Hz, 2H).

[Example 14]: 5-(4-(1-aminoethyl)phenyl)-1,8-naphthyridin-2(1H)-one hydrochloride

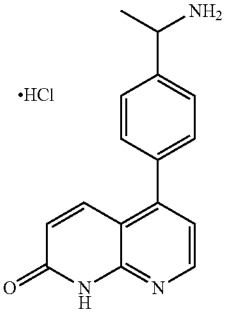 [SMILES: CC(N)c1ccc(-c2ccnc3[nH]c(=O)ccc23)cc1 ; Cl]

$^1$H NMR (400 MHz, DMSO-$d_6$) δ 12.27 (s, 1H), 8.55 (d, J=5.0 Hz, 1H), 7.78 (d, J=9.8 Hz, 1H), 7.56 (d, J=8.2 Hz, 2H), 7.46 (d, J=8.2 Hz, 2H), 7.20 (d, J=5.0 Hz, 2H), 6.56 (d, J=9.8 Hz, 1H), 4.53 (d, J=6.7 Hz, 1H), 1.46 (d, J=6.9 Hz, 3H).

[Example 15]: (R)-5-(4-(1-aminoethyl)phenyl)-1,8-naphthyridin-2(1H)-one hydrochloride

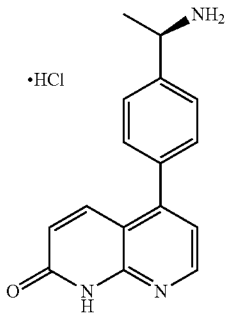 [SMILES: C[C@@H](N)c1ccc(-c2ccnc3[nH]c(=O)ccc23)cc1 ; Cl]

LC-MS (ESI) calcd for $C_{16}H_{15}N_3O$ $[M+H]^+$ 265.12, found m/z 266.17.

[Example 16]: 5-(4-(2-aminopropan-2-yl)phenyl)-1,8-naphthyridin-2(1H)-one hydrochloride

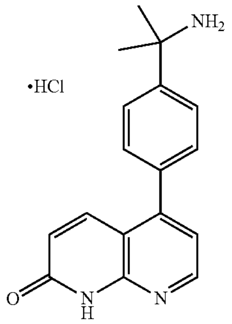 [SMILES: CC(C)(N)c1ccc(-c2ccnc3[nH]c(=O)ccc23)cc1 ; Cl]

$^1$H NMR (400 MHz, DMSO-$d_6$) δ 12.27 (s, 1H), 8.69 (s, 3H), 8.57 (d, J=5.0 Hz, 1H), 7.75 (d, J=8.3 Hz, 2H), 7.70 (d, J=9.8 Hz, 1H), 7.59 (d, J=8.3 Hz, 2H), 7.21 (d, J=5.0 Hz, 1H), 6.59 (d, J=9.8 Hz, 1H), 1.70 (s, 6H)

[Example 17]: (R)-5-(4-(1-(methylaminoethyl)phenyl)-1,8-naphthyridin-2(1H)-one hydrochloride

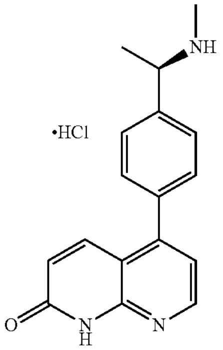 [SMILES: CN[C@H](C)c1ccc(-c2ccnc3[nH]c(=O)ccc23)cc1 ; Cl]

LC-MS (ESI) calcd for $C_{17}H_{17}N_3O$ $[M+H]^+$ 279.14, found m/z 280.19.

[Example 18]: (S)-5-(4-(1-(methylaminoethyl)phenyl)-1,8-naphthyridin-2(1H)-one hydrochloride

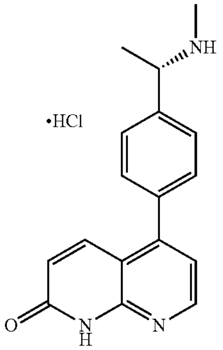 [SMILES: CN[C@@H](C)c1ccc(-c2ccnc3[nH]c(=O)ccc23)cc1 ; Cl]

LC-MS (ESI) calcd for $C_{17}H_{17}N_3O$ $[M+H]^+$ 279.14, found m/z 280.29.

[Example 19]: (R)-5-(4-(1-(cyclopropylaminoethyl)phenyl)-1,8-naphthyridin-2(1H)-one hydrochloride

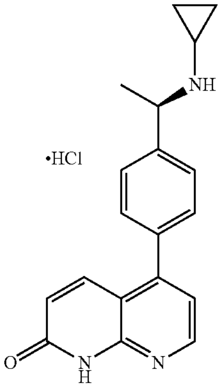 [SMILES: C[C@@H](NC1CC1)c1ccc(-c2ccnc3[nH]c(=O)ccc23)cc1 ; Cl]

LC-MS (ESI) calcd for $C_{19}H_{19}N_3O$ $[M+H]^+$ 305.15, found m/z 306.25.

[Example 20]: 5-(4-((ethylamino)methyl)-2-fluorophenyl)-1,8-naphthyridin-2(1H)-one hydrochloride

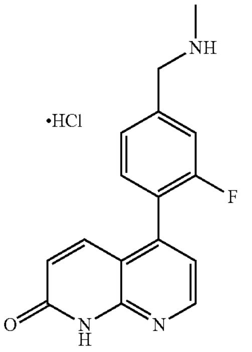 [SMILES: CNCc1ccc(-c2ccnc3[nH]c(=O)ccc23)c(F)c1 ; Cl]

$^1$H NMR (400 MHz, DMSO-$d_6$) δ 12.37 (s, 1H), 9.21 (s, 2H), 8.62 (d, J=4.9 Hz, 1H), 7.68 (d, J=10.5 Hz, 1H), 7.59 (d, J=7.2 Hz, 2H), 7.48 (dd, J=9.8, 2.7 Hz, 1H), 7.23 (d, J=4.9 Hz, 1H), 6.61 (dd, J=9.8, 1.9 Hz, 1H), 4.26 (t, J=5.5 Hz, 2H), 3.01 (dd, J=12.2, 7.2 Hz, 2H), 1.26 (t, J=7.2 Hz, 3H)

[Example 21]: 5-(2-fluoro-4-((isopropylamine)methyl)phenyl)-1,8-naphthyridin-2(1H)-one hydrochloride

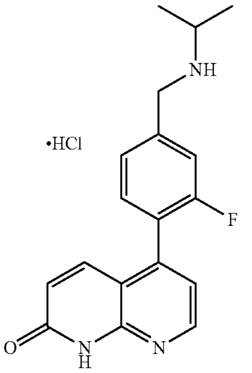 [SMILES: CC(C)NCc1ccc(-c2ccnc3[nH]c(=O)ccc23)c(F)c1 ; Cl]

LC-MS (ESI) calcd for $C_{17}H_{18}FN_3O$ $[M+H]^+$ 311.14, found m/z 312.03.

[Example 22]: 5-(4-((cyclopropylamino)methyl)-2-fluorophenyl)-1,8-naphthyridin-2(1H)-one hydrochloride

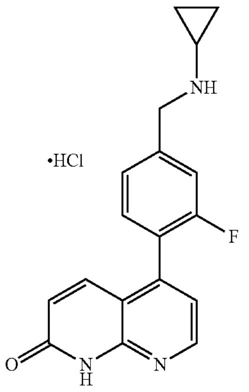 [SMILES: O=c1ccc2c(-c3ccc(CNC4CC4)cc3F)ccnc2[nH]1 ; Cl]

$^1$H NMR (400 MHz, DMSO-d6) δ 12.37 (s, 1H), 9.52 (s, 2H), 8.62 (d, J=4.9 Hz, 1H), 7.70 (d, J=10.3 Hz, 1H), 7.59 (d, J=4.4 Hz, 2H), 7.46 (dd, J=9.7, 2.6 Hz, 1H), 7.23 (d, J=4.9 Hz, 1H), 6.61 (d, J=9.7 Hz, 1H), 4.36 (s, 2H), 0.93 (s, 2H), 0.79 (t, J=6.6 Hz, 2H)

[Example 23]: 5-(3-fluoro-4-((methylamino)methyl)phenyl)-1,8-naphthyridin-2(1H)-one hydrochloride

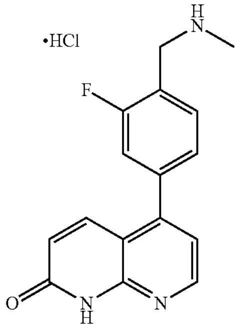 [SMILES: CNCc1ccc(-c2ccnc3[nH]c(=O)ccc23)cc1F ; Cl]

$^1$H NMR (400 MHz, DMSO-d6) δ 12.34 (s, 1H), 9.30 (s, 3H), 8.59 (d, J=4.9 Hz, 1H), 7.86-7.80 (m, 1H), 7.78-7.69 (d, 1H), 7.55 (d, J=10.6 Hz, 1H), 7.48-7.43 (dd, 1H), 7.24 (d, J=4.9 Hz, 1H), 4.28 (t, J=5.7 Hz, 2H), 2.50 (s, 3H)

[Example 24]: 5-(4-((ethylamino)methyl)-3-fluorophenyl)-1,8-naphthyridin-2(1H)-one hydrochloride

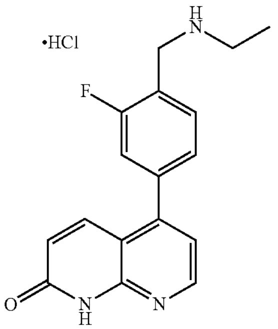 [SMILES: CCNCc1ccc(-c2ccnc3[nH]c(=O)ccc23)cc1F ; Cl]

$^{1}$H NMR (400 MHz, DMSO-d6) δ 12.34 (s, 1H), 9.13 (s, 2H), 8.60 (d, J=4.9 Hz, 1H), 7.83 (t, J=7.8 Hz, 1H), 7.72 (d, J=9.8 Hz, 1H), 7.55 (d, J=11.9 Hz, 1H), 7.48-7.43 (dd, 1H), 7.23 (d, J=4.9 Hz, 1H), 6.61 (dd, J=9.8, 1.7 Hz, 1H), 4.28 (s, 2H), 3.06 (q, J=7.0 Hz, 2H), 1.34-1.19 (t, 3H).

[Example 25]: 5-(4-((cyclopropylamino)methyl)-3-fluorophenyl)-1,8-naphthyridin-2(1H)-one hydrochloride

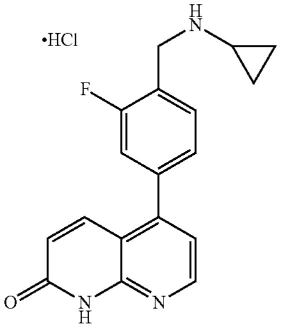 [SMILES: O=c1ccc2c(-c3ccc(CNC4CC4)c(F)c3)ccnc2[nH]1 ; Cl]

$^{1}$H NMR (400 MHz, DMSO-d6) δ 12.34 (s, 1H), 9.48 (s, 2H), 8.59 (d, J=4.9 Hz, 1H), 7.84 (t, J=7.8 Hz, 1H), 7.71 (d, J=9.8 Hz, 1H), 7.54 (d, J=10.5 Hz, 1H), 7.49-7.40 (m, 1H), 7.23 (d, J=4.9 Hz, 1H), 6.61 (dd, J=9.8, 1.9 Hz, 1H), 4.37 (s, 2H), 2.77 (s, 1H), 0.88 (d, J=15.4 Hz, 2H), 0.79 (q, J=6.7 Hz, 2H).

[Example 26]: 5-(isoindolin-5-yl)-1,8-naphthyridin-2(1H)-one hydrochloride

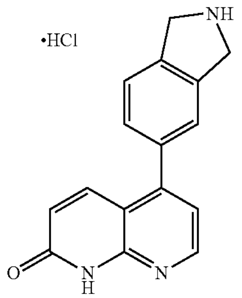 [SMILES: O=c1ccc2c(-c3ccc4c(c3)CNC4)ccnc2[nH]1 ; Cl]

$^{1}$H NMR (400 MHz, DMSO-d6) δ 12.31 (s, 1H), 9.96 (s, 2H), 8.58 (d, J=4.9 Hz, 1H), 7.74 (d, J=9.8 Hz, 1H), 7.61 (d, J=7.9 Hz, 1H), 7.56 (s, 1H), 7.50 (d, J=7.8 Hz, 1H), 7.20 (d, J=4.9 Hz, 1H), 6.57 (dd, J=9.8, 1.6 Hz, 1H), 4.60 (s, 4H)

[Example 27]: 5-(1,2,3,4-tetrahydroisoquinolin-7-yl)-1,8-naphthyridin-2(1H)-one hydrochloride

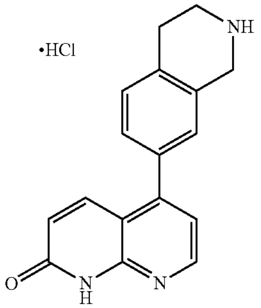 [SMILES: O=c1ccc2c(-c3ccc4c(c3)CNCC4)ccnc2[nH]1 ; Cl]

$^{1}$H NMR (400 MHz, DMSO-d6) δ 12.30 (s, 1H), 9.60 (s, 2H), 8.57 (d, J=4.9 Hz, 1H), 7.76 (d, J=9.8 Hz, 1H), 7.41 (d, J=6.1 Hz, 3H), 7.18 (d, J=4.9 Hz, 1H), 6.57 (d, J=9.8 Hz, 1H), 4.34 (brs, 2H), 3.41 (brs, 2H), 3.11 (t, J=6.1 Hz, 2H)

[Example 28]: 5-(6-fluoro-1,2,3,4-tetrahydroisoquinolin-7-yl)-1,8-naphthyridin-2(1H)-one hydrochloride

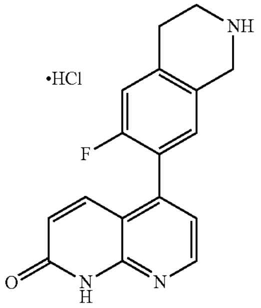 [SMILES: O=c1ccc2c(-c3cc4c(cc3F)CCNC4)ccnc2[nH]1 ; Cl]

LC-MS (ESI) calcd for $C_{17}H_{14}FN_3O$ [M+H]$^{+}$ 295.11, found m/z 296.11.

[Example 29]: 5-(4-(aminomethyl)phenyl)-1-methyl-1,8-naphthyridin-2(1H)-one hydrochloride

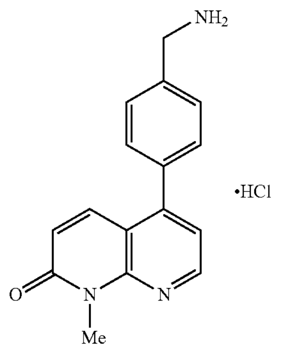 [SMILES: Cn1c(=O)ccc2c(-c3ccc(CN)cc3)ccnc21 ; Cl]

$^1$H NMR (400 MHz, DMSO-d6) δ 8.72 (d, J=4.9 Hz, 1H), 7.75-7.65 (m, 3H), 7.59 (d, J=7.9 Hz, 2H), 7.29 (d, J=4.9 Hz, 1H), 6.75 (d, J=9.8 Hz, 1H), 4.17 (d, J=5.6 Hz, 2H), 3.76 (s, 3H).

[Preparation of Sulfamide 6]: A solution of tert-butanol (1.0 equiv.) in anhydrous dichloromethane (1.4 M) was added to a round bottom flask and 5 (1.0 equiv.) was slowly added dropwise thereto. Then, N,N-dimethylpyridin-4-amine (2.0 equiv.) was added thereto. The solution was stirred at room temperature for 1 hour. After the reaction was complete, the reaction product was washed several times with water. The organic layer was dried over anhydrous sodium sulfate and concentrated in vacuo. The obtained colorless powder 6 (80% yield) was used as a reactant without further purification.

Step 3: A solution of triethylamine (2.5 equiv.) in dichloromethane (0.1 M) was added to a round bottom flask. Then, 4 (1.0 equiv.) and 6 (1.1 equiv.) were added thereto, followed by stirring at room temperature for one day. After the reaction was completed, the reaction product was concentrated under reduced pressure and dried, and the obtained residue was extracted using dichloromethane and water. The resulting residue was purified through column chromatography (1:20 MeOH:$CH_2Cl_2$) to obtain 7 (30-60% yield).

[Example 30]: tert-butyl(N-(3-(7-oxo-7,8-dihydro-1,8-naphthyridin-4-yl)phenyl)sulfamoyl)carbamate

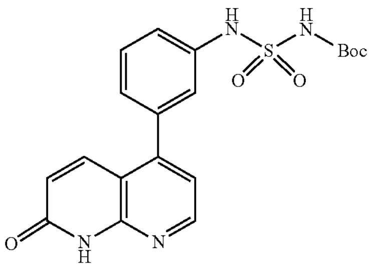 [SMILES: CC(C)(C)OC(=O)NS(=O)(=O)Nc1cccc(-c2ccnc3[nH]c(=O)ccc23)c1]

$^1$H NMR (400 MHz, MeOD-d4) δ 8.57 (d, J=4.9 Hz, 1H), 8.00 (d, J=9.8 Hz, 1H), 7.48 (t, J=7.7 Hz, 1H), 7.36 (d, J=8.5 Hz, 2H), 7.26 (d, J=4.9 Hz, 1H), 7.19 (d, J=7.6 Hz, 1H), 6.65 (d, J=9.8 Hz, 1H), 1.35 (s, 9H).

[Example 31]: tert-butyl(N-(3-(7-oxo-7,8-dihydro-1,8-naphthyridin-4-yl)benzyl)sulfamoyl)carbamate

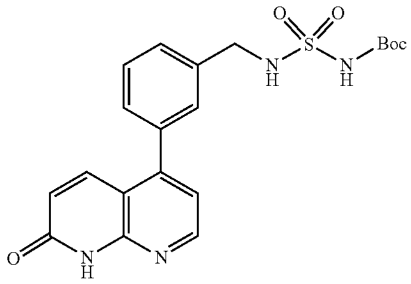 [SMILES: CC(C)(C)OC(=O)NS(=O)(=O)NCc1cccc(-c2ccnc3[nH]c(=O)ccc23)c1]

$^1$H NMR (400 MHz, MeOD-d4) δ 8.58 (d, J=4.9 Hz, 1H), 8.01 (d, J=9.8 Hz, 1H), 7.54 (d, J=4.7 Hz, 2H), 7.51 (s, 1H), 7.44-7.38 (m, 1H), 7.27 (d, J=4.9 Hz, 1H), 6.65 (d, J=9.8 Hz, 1H), 4.30 (s, 2H), 1.39 (s, 9H)

[Example 32]: tert-butyl(N-(4-(7-oxo-7,8-dihydro-1,8-naphthyridin-4-yl)benzyl)sulfamoyl)carbamate

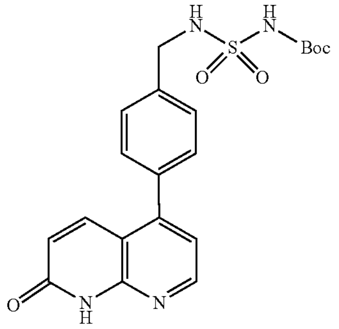 [SMILES: CC(C)(C)OC(=O)NS(=O)(=O)NCc1ccc(-c2ccnc3[nH]c(=O)ccc23)cc1]

$^1$H NMR (400 MHz, DMSO-d6) δ 12.23 (s, 1H), 8.54 (d, J=4.9 Hz, 1H), 7.76 (d, J=9.8 Hz, 1H), 7.51 (d, J=8.0 Hz, 2H), 7.45 (d, J=7.8 Hz, 2H), 7.18 (d, J=4.9 Hz, 1H), 6.54 (d, J=9.8 Hz, 1H), 4.09 (d, J=6.1 Hz, 3H), 1.37 (s, 9H).

[Example 33]: tert-butyl(N-(2-fluoro-4-(7-oxo-7,8-dihydro-1,8-naphthyridin-4-yl)benzyl)sulfamoyl)carbamate

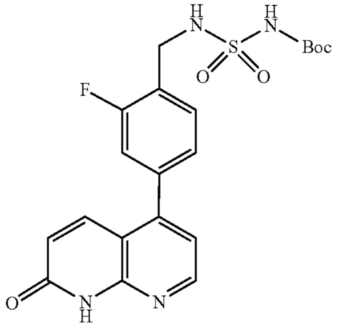 [SMILES: CC(C)(C)OC(=O)NS(=O)(=O)NCc1ccc(-c2ccnc3[nH]c(=O)ccc23)cc1F]

$^{1}$H NMR (400 MHz, MeOD-d4) δ 8.59 (d, J=5.0 Hz, 1H), 7.96 (d, J=9.8 Hz, 1H), 7.69 (t, J=7.7 Hz, 1H), 7.31-7.23 (m, 3H), 6.66 (d, J=9.8 Hz, 1H), 4.34 (s, 2H), 1.44 (s, 9H).

[Example 34]: tert-butyl(N-(4-(8-methyl-7-oxo-7,8-dihydro-1,8-naphthyridin-4-yl)benzyl)sulfamoyl) carbamate

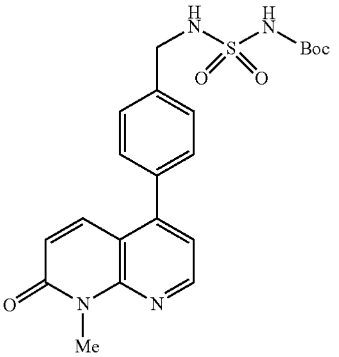 [SMILES: Cn1c(=O)ccc2c(-c3ccc(CNS(=O)(=O)NC(=O)OC(C)(C)C)cc3)ccnc21]

$^{1}$H NMR (400 MHz, DMSO-d6) δ 8.68 (d, J=4.9 Hz, 1H), 7.76 (d, J=9.8 Hz, 1H), 7.52 (d, J=8.0 Hz, 2H), 7.45 (d, J=8.2 Hz, 2H), 7.25 (d, J=4.9 Hz, 1H), 6.68 (d, J=9.8 Hz, 1H), 4.19 (d, J=6.1 Hz, 2H), 3.73 (s, 3H), 1.38 (s, 9H).

Step 4: 7 (1.0 equiv.) was dissolved in dichloromethane (0.04 M) in a round bottom flask. Then, a hydrochloride solution (4.0 M in 1,4-dioxane, 0.2M) was added thereto, followed by stirring at room temperature for 16 hours. After the reaction was completed, the reaction product was concentrated under reduced pressure and the resulting residue was washed with diethyl ether, filtered and dried to obtain 8 (40-80% yield).

[Example 35]: N-(3-(7-oxo-7,8-dihydro-1,8-naphthyridin-4-yl)phenyl)sulfamide hydrochloride

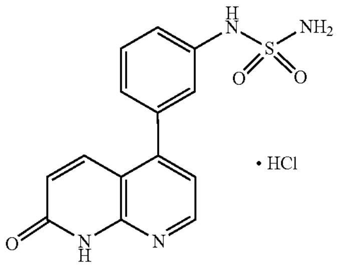 [SMILES: NS(=O)(=O)Nc1cccc(-c2ccnc3[nH]c(=O)ccc23)c1 ; "· HCl"]

$^{1}$H NMR (400 MHz, MeOD-d4) δ 8.60 (d, J=5.0 Hz, 1H), 8.04 (d, J=9.8 Hz, 1H), 7.52-7.47 (m, 1H), 7.39-7.34 (m, 2H), 7.31 (d, J=5.1 Hz, 1H), 7.18 (d, J=7.7 Hz, 1H), 6.69 (d, J=9.8 Hz, 1H).

[Example 36]: N-(2-fluoro-5-(7-oxo-7,8-dihydro-1,8-naphthyridin-4-yl)phenyl)sulfamide hydrochloride

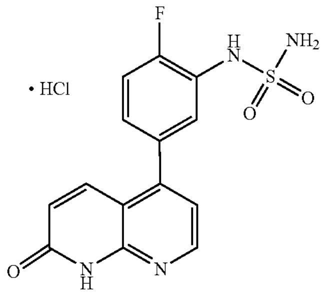 [SMILES: NS(=O)(=O)Nc1cc(-c2ccnc3[nH]c(=O)ccc23)ccc1F ; "· HCl"]

$^{1}$H NMR (400 MHz, DMSO-d6) δ 12.29 (s, 1H), 9.47 (s, 2H), 8.57 (d, J=4.9 Hz, 1H), 7.80 (d, J=9.8 Hz, 1H), 7.58 (dd, J=7.8, 2.1 Hz, 1H), 7.42 (dd, J=10.5, 8.5 Hz, 3H), 7.28-7.21 (m, 6H), 6.56 (d, J=9.8 Hz, 2H).

[Example 37]: N-(3-(7-oxo-7,8-dihydro-1,8-naphthyridin-4-yl)benzyl)sulfamide

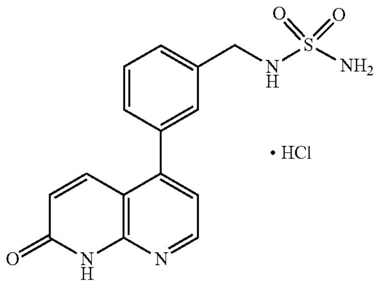 [SMILES: NS(=O)(=O)NCc1cccc(-c2ccnc3[nH]c(=O)ccc23)c1 ; "· HCl"]

$^{1}$H NMR (400 MHz, MeOD-d4) δ 8.64 (d, J=5.2 Hz, 1H), 8.07 (d, J=9.7 Hz, 1H), 7.57 (q, J=3.9, 2.9 Hz, 3H), 7.47-7.40 (m, 1H), 7.37 (d, J=5.1 Hz, 1H), 6.75 (d, J=9.7 Hz, 1H), 4.32 (s, 2H).

[Example 38]: N-(2-fluoro-5-(7-oxo-7,8-dihydro-1,8-naphthyridin-4-yl)benzyl)sulfamide hydrochloride

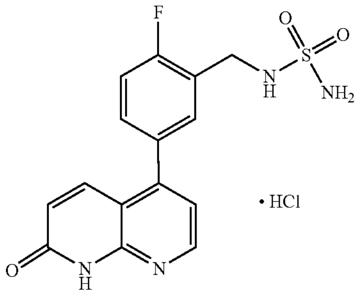 [SMILES: NS(=O)(=O)NCc1cc(-c2ccnc3[nH]c(=O)ccc23)ccc1F ; "· HCl"]

$^{1}$H NMR (400 MHz, DMSO-d6) δ 12.29 (s, 1H), 8.57 (d, J=4.9 Hz, 1H), 7.81 (d, J=9.8 Hz, 1H), 7.66-7.56 (m, 1H), 7.49-7.43 (m, 1H), 7.43-7.32 (m, 1H), 7.20 (d, J=4.9 Hz, 2H), 6.55 (d, J=9.8 Hz, 1H), 4.22 (s, 2H).

[Example 39]: N-(4-(7-oxo-7,8-dihydro-1,8-naphthyridin-4-yl)phenyl)sulfamide

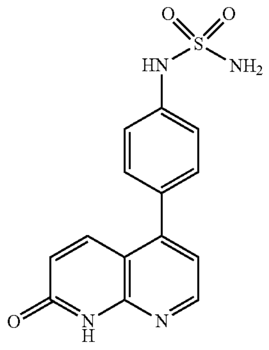

$^1$H NMR (400 MHz, Acetone-d6) δ 8.45 (d, J=5.0 Hz, 1H), 8.01 (d, J=9.8 Hz, 1H), 7.26-7.22 (m, 2H), 7.14 (d, J=5.0 Hz, 1H), 6.86-6.81 (m, 2H), 6.55 (d, J=9.8 Hz, 1H).

[Example 40]: N-(4-(7-oxo-7,8-dihydro-1,8-naphthyridin-4-yl)benzyl)sulfamide

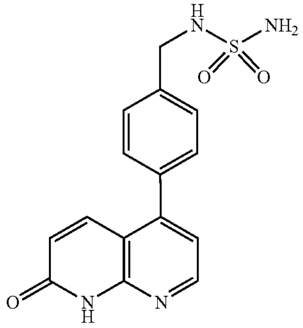 [SMILES: NS(=O)(=O)NCc1ccc(-c2ccnc3[nH]c(=O)ccc23)cc1]

$^1$H NMR (400 MHz, MeOD-d4) δ 8.61 (d, J=5.1 Hz, 1H), 8.03 (d, J=9.8 Hz, 1H), 7.62 (d, J=7.8 Hz, 2H), 7.50 (d, J=8.4 Hz, 2H), 7.33 (d, J=5.1 Hz, 1H), 6.72 (d, J=9.7 Hz, 1H), 4.32 (s, 2H).

[Example 41]: N-(2-fluoro-4-(7-oxo-7,8-dihydro-1,8-naphthyridin-4-yl)benzyl)sulfamide

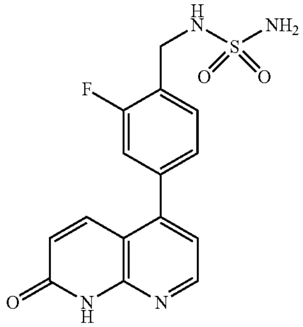 [SMILES: NS(=O)(=O)NCc1ccc(-c2ccnc3[nH]c(=O)ccc23)cc1F]

$^1$H NMR (400 MHz, MeOD-d4) δ 8.62 (d, J=4.8 Hz, 1H), 8.01 (d, J=10.3 Hz, 1H), 7.73 (t, J=7.7 Hz, 1H), 7.35-7.28 (m, 3H), 6.73 (d, J=10.3 Hz, 1H), 4.38 (s, 2H).

[Example 42]: N-(3-fluoro-4-(7-oxo-7,8-dihydro-1,8-naphthyridin-4-yl)benzyl)sulfamide hydrochloride

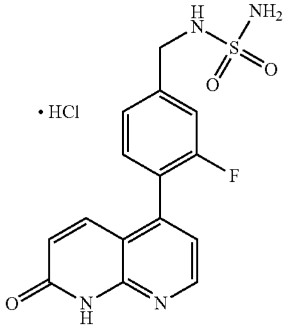 [SMILES: NS(=O)(=O)NCc1ccc(-c2ccnc3[nH]c(=O)ccc23)c(F)c1 ; "· HCl"]

$^1$H NMR (400 MHz, DMSO-d6) δ 12.32 (s, 1H), 8.59 (d, J=4.9 Hz, 1H), 7.45 (ddd, J=23.0, 16.6, 8.7 Hz, 5H), 7.30 (s, 1H), 7.22 (d, J=4.7 Hz, 1H), 6.74 (s, 2H), 6.58 (d, J=9.6 Hz, 1H), 4.21 (s, 2H).

[Example 43]: N-(2,3-difluoro-4-(7-oxo-7,8-dihydro-1,8-naphthyridin-4-yl)benzyl)sulfamide hydrochloride

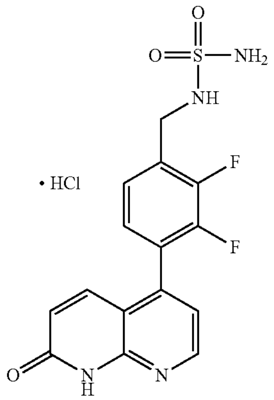 [SMILES: NS(=O)(=O)NCc1ccc(-c2ccnc3[nH]c(=O)ccc23)c(F)c1F ; "· HCl"]

$^1$H NMR (400 MHz, DMSO-d6) δ 12.36 (s, 1H), 8.62 (d, J=4.9 Hz, 1H), 7.57 (dd, J=9.8, 2.7 Hz, 1H), 7.49 (t, J=7.2 Hz, 1H), 7.31 (t, J=6.7 Hz, 2H), 7.26 (d, J=4.9 Hz, 1H), 6.76 (s, 1H), 6.59 (d, J=9.8 Hz, 1H), 4.26 (s, 2H).

[Example 44]: N-(3,5-difluoro-4-(7-oxo-7,8-dihydro-1,8-naphthyridin-4-yl)benzyl)sulfamide hydrochloride

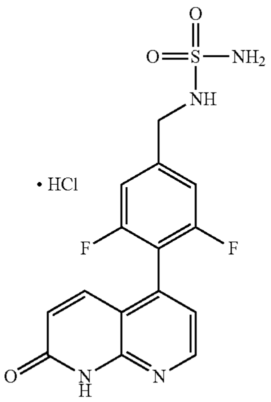 [SMILES: NS(=O)(=O)NCc1cc(F)c(-c2ccnc3[nH]c(=O)ccc23)c(F)c1 ; "· HCl"]

$^1$H NMR (400 MHz, DMSO-d6) δ 12.39 (s, 1H), 8.63 (d, J=4.9 Hz, 1H), 7.45 (d, J=9.8 Hz, 1H), 7.35 (d, J=8.6 Hz, 2H), 7.29 (d, J=4.9 Hz, 1H), 7.10 (d, J=50.9 Hz, 1H), 6.77 (s, 1H), 6.60 (d, J=9.8 Hz, 1H), 4.22 (d, J=6.2 Hz, 2H).

[Example 45]: N-(1-(4-(7-oxo-7,8-dihydro-1,8-naphthyridin-4-yl)phenyl)ethyl)sulfamide hydrochloride

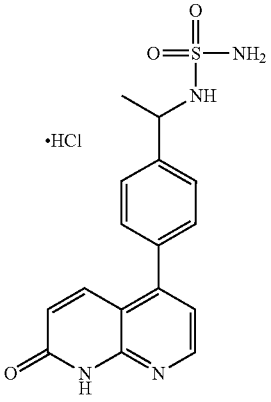 [SMILES: CC(NS(N)(=O)=O)c1ccc(-c2ccnc3[nH]c(=O)ccc23)cc1 ; Cl]

$^1$H NMR (400 MHz, DMSO-d6) δ 12.30 (s, 3H), 8.57 (t, J=5.4 Hz, 11H), 7.71 (dd, J=9.0, 3.2 Hz, 10H), 7.59 (d, J=8.2 Hz, 7H), 7.21 (d, J=4.9 Hz, 4H), 6.60 (d, J=9.8 Hz, 3H), 4.57-4.42 (m, 3H), 1.58 (d, J=6.8 Hz, 9H).

[Example 46]: (R)-(N-(1-(4-(7-oxo-7,8-dihydro-1,8-naphthyridin-4-yl)phenyl)ethyl)sulfamide hydrochloride

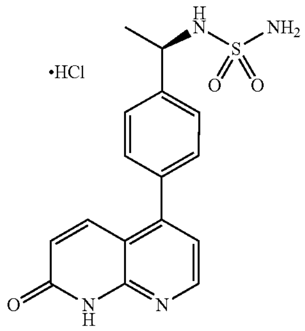 [SMILES: C[C@@H](NS(N)(=O)=O)c1ccc(-c2ccnc3[nH]c(=O)ccc23)cc1 ; Cl]

$^1$H NMR (400 MHz, DMSO-d6) δ 12.26 (brs, 1H), 8.55 (d, J=4.9 Hz, 1H), 7.78 (d, J=9.8 Hz, 1H), 7.56 (d, J=8.2 Hz, 2H), 7.46 (d, J=8.2 Hz, 2H), 7.19 (t, J=10.8 Hz, 2H), 6.56 (d, J=9.8 Hz, 2H), 4.53 (d, J=5.9 Hz, 1H), 1.46 (d, J=6.9 Hz, 3H).

[Example 47]: (S)-(N-(1-(4-(7-oxo-7,8-dihydro-1,8-naphthyridin-4-yl)phenyl)ethyl)sulfamide hydrochloride

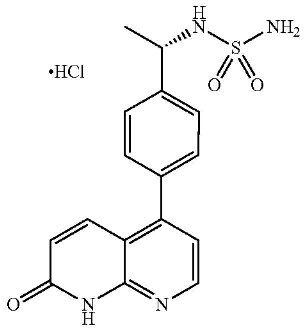 [SMILES: C[C@H](NS(N)(=O)=O)c1ccc(-c2ccnc3[nH]c(=O)ccc23)cc1 ; Cl]

$^1$H NMR (400 MHz, DMSO-d6) δ 12.26 (brs, 1H), 8.55 (d, J=5.0 Hz, 1H), 7.78 (d, J=9.8 Hz, 1H), 7.56 (d, J=8.2 Hz, 2H), 7.46 (d, J=8.2 Hz, 2H), 7.21 (d, J=5.0 Hz, 1H), 6.56 (d, J=9.8 Hz, 1H), 6.06 (brs, 4H), 4.53 (q, J=6.8 Hz, 1H), 1.46 (d, J=6.9 Hz, 3H).

[Example 48]: (R)-(N-(1-(2-fluoro-4-(7-oxo-7,8-dihydro-1,8-naphthyridin-4-yl)phenyl)ethyl)sulfamide hydrochloride

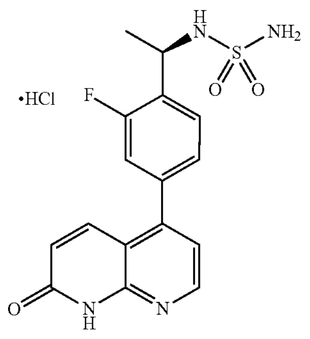 [SMILES: C[C@@H](NS(N)(=O)=O)c1ccc(-c2ccnc3[nH]c(=O)ccc23)cc1F ; Cl]

LC-MS (ESI) calcd for $C_{16}H_{15}FN_4O_3S$ $[M+H]^+$ 362.08, found m/z 363.53.

[Example 49]: (R)-(N-(1-(3-fluoro-4-(7-oxo-7,8-dihydro-1,8-naphthyridin-4-yl)phenyl)ethyl)sulfamide hydrochloride

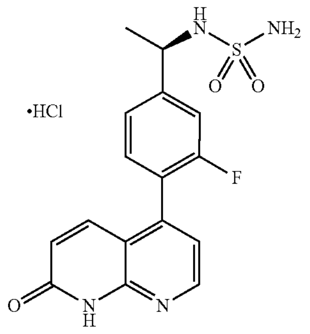 [SMILES: C[C@@H](NS(N)(=O)=O)c1ccc(-c2ccnc3[nH]c(=O)ccc23)c(F)c1 ; Cl]

LC-MS (ESI) calcd for $C_{16}H_{15}FN_4O_3S$ $[M+H]^+$ 362.08, found m/z 363.53.

[Example 50]: N-methyl-N-(4-(7-oxo-7,8-dihydro-1,8-naphthyridin-4-yl)benzyl)sulfamide hydrochloride

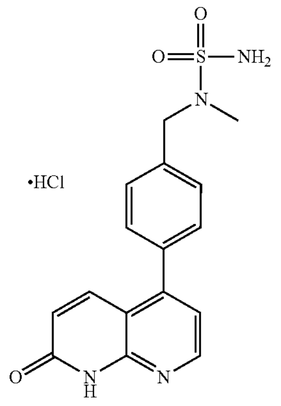 [SMILES: CN(Cc1ccc(-c2ccnc3[nH]c(=O)ccc23)cc1)S(N)(=O)=O ; Cl]

$^1H$ NMR (400 MHz, DMSO-d6) δ 12.27 (s, 1H), 8.56 (d, J=4.9 Hz, 1H), 7.78 (d, J=9.8 Hz, 1H), 7.53 (q, J=8.4 Hz, 4H), 7.22 (d, J=4.9 Hz, 1H), 6.96 (s, 2H), 6.57 (d, J=9.8 Hz, 1H), 4.19 (s, 2H), 2.60 (s, 3H).

[Example 51]: N-ethyl-N-(4-(7-oxo-7,8-dihydro-1,8-naphthyridin-4-yl)benzyl)sulfamide hydrochloride

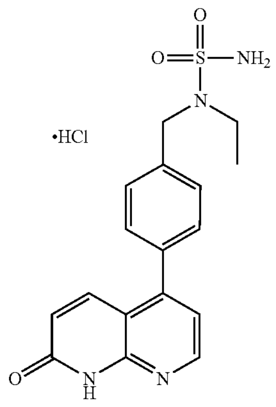 [SMILES: CCN(Cc1ccc(-c2ccnc3[nH]c(=O)ccc23)cc1)S(N)(=O)=O ; Cl]

$^1H$ NMR (400 MHz, DMSO-d6) δ 12.27 (s, 1H), 8.55 (d, J=4.9 Hz, 1H), 7.77 (d, J=9.8 Hz, 1H), 7.57 (d, J=8.2 Hz, 2H), 7.49 (d, J=8.2 Hz, 2H), 7.22 (d, J=5.0 Hz, 1H), 6.91 (s, 2H), 6.57 (d, J=9.8 Hz, 1H), 4.33 (s, 2H), 3.25-3.10 (m, 2H), 1.07 (t, J=7.1 Hz, 3H).

[Example 52]: N-(2-fluoro-4-(7-oxo-7,8-dihydro-1,8-naphthyridin-4-yl)benzyl)-N-methylsulfamide hydrochloride

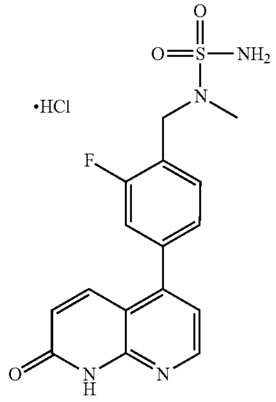 [SMILES: CN(Cc1ccc(-c2ccnc3[nH]c(=O)ccc23)cc1F)S(N)(=O)=O ; Cl]

$^1H$ NMR (400 MHz, DMSO-d6) δ 12.30 (s, 1H), 8.57 (d, J=4.9 Hz, 1H), 7.79 (d, J=9.8 Hz, 1H), 7.62 (t, J=7.8 Hz, 1H), 7.40 (dd, J=23.8, 9.8 Hz, 2H), 7.24 (d, J=4.9 Hz, 1H), 6.99 (s, 2H), 6.58 (d, J=10.0 Hz, 1H), 4.24 (s, 2H), 2.65 (s, 3H).

[Example 53]: N-ethyl-N-(2-fluoro-4-(7-oxo-7,8-dihydro-1,8-naphthyridin-4-yl)benzyl)sulfamide hydrochloride

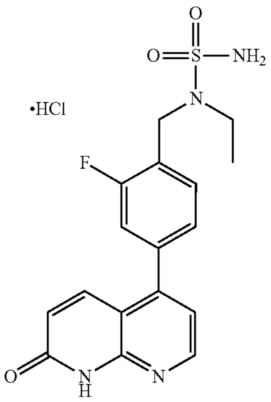 [SMILES: CCN(Cc1ccc(-c2ccnc3[nH]c(=O)ccc23)cc1F)S(N)(=O)=O ; Cl]

$^1$H NMR (400 MHz, DMSO-d6) δ 12.29 (s, 1H), 8.57 (d, 1H), 7.77 (d, 1H), 7.66 (d, 1H), 7.38 (dd, J=17.7, 9.3 Hz, 2H), 7.31 (s, 1H), 7.18 (s, 1H) 7.05 (s, 1H), 6.95 (S, 1H) 6.58 (d, J=10.1 Hz, 1H), 4.37 (s, 2H), 1.25 (m, 2H), 1.09 (t, J=7.0 Hz, 3H)

[Example 54]: N-cyclopropyl-N-(2-fluoro-4-(7-oxo-7,8-dihydro-1,8-naphthyridin-4-yl)benzyl)sulfamide hydrochloride

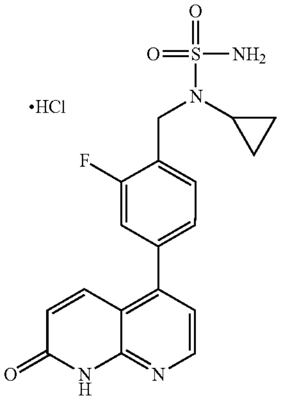 [SMILES: NS(=O)(=O)N(Cc1ccc(-c2ccnc3[nH]c(=O)ccc23)cc1F)C1CC1 ; Cl]

LC-MS (ESI) calcd for $C_{18}H_{17}FN_4O_3S$ $[M+H]^+$ 389.26, found m/z 389.3.

[Example 55]: N-(3-fluoro-4-(7-oxo-7,8-dihydro-1,8-naphthyridin-4-yl)benzyl)-N-methylsulfamide hydrochloride

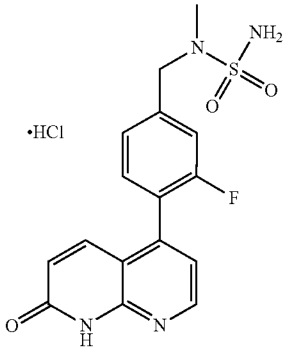 [SMILES: CN(Cc1ccc(-c2ccnc3[nH]c(=O)ccc23)c(F)c1)S(N)(=O)=O ; Cl]

$^1$H NMR (400 MHz, DMSO-d6) δ 12.33 (s, 1H), 8.60 (d, J=4.9 Hz, 1H), 7.55 (dd, J=9.8, 2.7 Hz, 1H), 7.50 (t, J=7.9 Hz, 1H), 7.40 (t, J=7.7 Hz, 2H), 7.32 (d, J=6.2 Hz, 2H), 7.24 (d, J=4.8 Hz, 1H), 7.00 (s, 2H), 6.57 (d, J=9.2 Hz, 1H), 4.22 (s, 2H), 2.64 (s, 3H).

[Example 56]: N-ethyl-N-(3-fluoro-4-(7-oxo-7,8-dihydro-1,8-naphthyridin-4-yl)benzyl)sulfamide hydrochloride

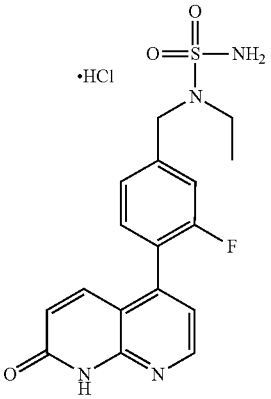 [SMILES: CCN(Cc1ccc(-c2ccnc3[nH]c(=O)ccc23)c(F)c1)S(N)(=O)=O ; Cl]

$^1$H NMR (400 MHz, DMSO-d6) δ 12.32 (s, 1H), 8.59 (d, J=4.9 Hz, 1H), 7.53 (dd, J=9.7, 2.8 Hz, 1H), 7.45 (dt, J=15.6, 7.2 Hz, 3H), 7.24 (d, J=4.9 Hz, 1H), 6.58 (d, J=9.8 Hz, 1H), 4.36 (s, 2H), 3.16 (q, J=7.2 Hz, 2H), 1.09 (t, J=7.1 Hz, 3H).

[Example 57]: N-(3-fluoro-4-(7-oxo-7,8-dihydro-1,8-naphthyridin-4-yl)benzyl)-N-isopropyl)sulfamide hydrochloride

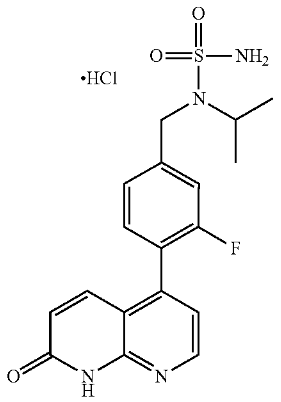 [SMILES: CC(C)N(Cc1ccc(-c2ccnc3[nH]c(=O)ccc23)c(F)c1)S(N)(=O)=O ; Cl]

LC-MS (ESI) calcd for $C_{18}H_{19}FN_4O_3S$ $[M+H]^+$ 391.25, found m/z 391.2.

[Example 58]: N-cyclopropyl-N-(3-fluoro-4-(7-oxo-7,8-dihydro-1,8-naphthyridin-4-yl)benzyl)sulfamide hydrochloride

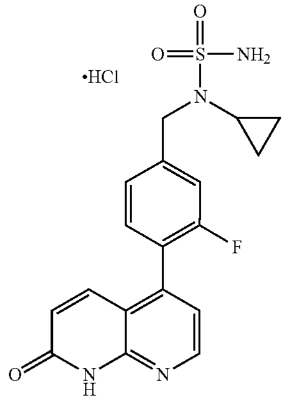 [SMILES: NS(=O)(=O)N(Cc1ccc(-c2ccnc3[nH]c(=O)ccc23)c(F)c1)C1CC1 ; Cl]

$^1$H NMR (400 MHz, DMSO-d6) δ 12.32 (s, 1H), 8.59 (d, J=4.9 Hz, 1H), 7.52 (dd, J=9.7, 2.8 Hz, 1H), 7.45 (t, J=7.7 Hz, 2H), 7.37 (s, 1H), 7.34 (d, J=5.7 Hz, 2H), 7.23 (d, J=4.9 Hz, 1H), 7.21 (s, 1H), 7.08 (s, 1H), 6.58 (d, J=9.8 Hz, 1H), 4.39 (s, 2H), 0.64 (d, J=5.1 Hz, 4H)

[Example 59]: (R)-(N-methyl-N-(1-(4-(7-oxo-7,8-dihydro-1,8-naphthyridin-4-yl)phenyl)ethyl)sulfamide hydrochloride

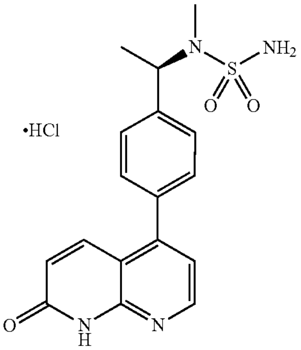 [SMILES: C[C@H](c1ccc(-c2ccnc3[nH]c(=O)ccc23)cc1)N(C)S(N)(=O)=O ; Cl]

$^1$H NMR (400 MHz, DMSO-d6) δ 12.28 (s, 1H), 8.56 (d, J=4.9 Hz, 1H), 7.78 (d, J=9.8 Hz, 1H), 7.59 (d, J=8.2 Hz, 2H), 7.51 (d, J=8.2 Hz, 2H), 7.22 (d, J=4.9 Hz, 1H), 6.89 (s, 1H), 6.57 (d, J=9.8 Hz, 1H), 5.11 (q, J=7.1 Hz, 1H), 2.52 (s, 3H), 1.56 (d, J=7.0 Hz, 3H).

[Example 60]: (R)-(N-cyclopropyl-N-(1-(4-(7-oxo-7,8-dihydro-1,8-naphthyridin-4-yl)phenyl)ethyl) sulfamide hydrochloride

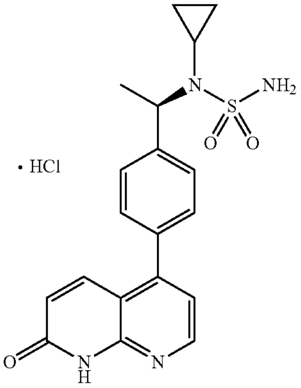

$^1$H NMR (400 MHz, MeOD-d4) δ 8.71 (d, J=5.4 Hz, 1H), 8.16 (d, J=9.6 Hz, 1H), 7.72 (d, J=8.1 Hz, 2H), 7.56 (d, J=8.3 Hz, 2H), 7.51 (d, J=5.4 Hz, 1H), 6.90 (d, J=9.6 Hz, 1H), 5.26 (q, J=7.1 Hz, 1H), 2.46-2.37 (m, 1H), 1.85 (d, J=7.1 Hz, 3H), 0.94-0.82 (m, 1H), 0.76-0.70 (m, 1H), 0.60-0.48 (m, 1H), 0.33-0.28 (m, 1H).

[Example 61]: (S)-(N-methyl-N-(1-(4-(7-oxo-7,8-dihydro-1,8-naphthyridin-4-yl)phenyl)ethyl)sulfamide hydrochloride

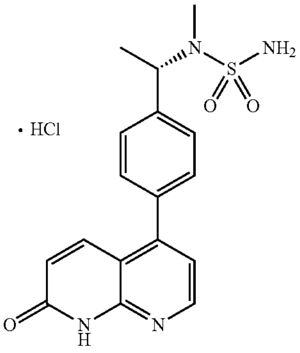

$^1$H NMR (400 MHz, MeOD-d4) δ 8.69 (d, J=5.3 Hz, 1H), 8.14 (d, J=9.6 Hz, 1H), 7.71 (d, J=8.1 Hz, 2H), 7.58 (d, J=8.2 Hz, 2H), 7.46 (d, J=5.3 Hz, 1H), 6.85 (d, J=9.6 Hz, 1H), 5.31 (q, J=7.3 Hz, 1H), 2.67 (s, 3H), 1.69 (d, J=7.0 Hz, 3H).

[Example 62]: (R)-(N-(1-(2-fluoro-4-(7-oxo-7,8-dihydro-1,8-naphthyridin-4-yl)phenyl)ethyl)sulfamide hydrochloride

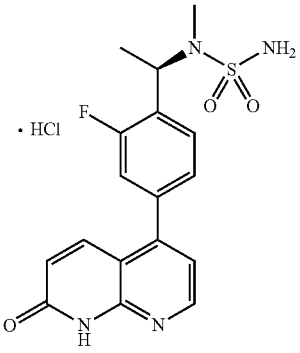

LC-MS (ESI) calcd for $C_{17}H_{17}FN_4O_3S$ $[M+H]^+$ 376.10, found m/z 377.25.

[Example 63]: (R)-(N-(1-(3-fluoro-4-(7-oxo-7,8-dihydro-1,8-naphthyridin-4-yl)phenyl)ethyl)sulfamide hydrochloride

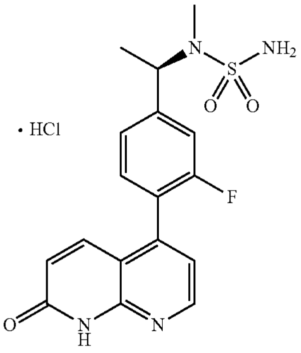

LC-MS (ESI) calcd for $C_{17}H_{17}FN_4O_3S$ $[M+H]^+$ 376.10, found m/z 377.28.

[Example 64]: 5-(7-oxo-7,8-dihydro-1,8-naphthyridin-4-yl)isoindolin-2-yl)sulfamide hydrochloride

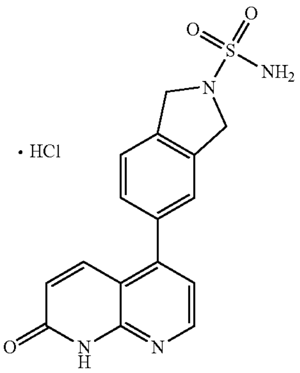

$^1$H NMR (400 MHz, DMSO-d6) δ 12.28 (s, 1H), 8.56 (d, J=4.9 Hz, 1H), 7.77 (d, J=9.8 Hz, 1H), 7.53 (d, J=7.9 Hz, 1H), 7.48 (s, 1H), 7.42 (d, J=7.7 Hz, 1H), 7.20 (d, J=5.0 Hz, 1H), 6.99 (s, 2H), 6.56 (dd, J=9.8, 1.9 Hz, 1H), 4.60 (s, 4H).

[Example 65]: 7-(7-oxo-7,8-dihydro-1,8-naphthyridin-4-yl)dihydroisoquinoline-2(1H)-sulfamide hydrochloride

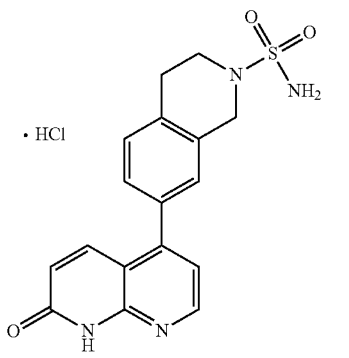

$^1$H NMR (400 MHz, DMSO-d6) δ 12.26 (s, 1H), 8.55 (d, J=4.9 Hz, 1H), 7.81 (d, J=9.8 Hz, 1H), 7.37 (d, J=7.8 Hz, 1H), 7.34-7.27 (m, 2H), 7.20 (d, J=5.0 Hz, 1H), 6.97 (s, 2H), 6.56 (d, J=9.8 Hz, 1H), 4.30 (s, 2H), 3.33 (t, J=5.9 Hz, 2H), 3.01 (t, J=5.6 Hz, 2H).

[Example 66]: 6-fluoro-7-(7-oxo-7,8-dihydro-1,8-naphthyridin-4-yl)-3,4-dihydroisoquinoline-2(1H)-sulfamide hydrochloride

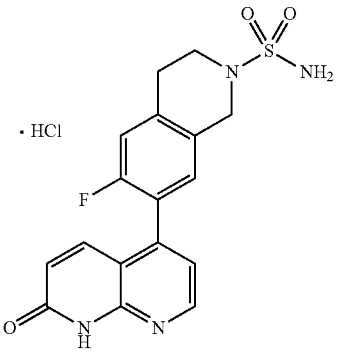

$^1$H NMR (400 MHz, DMSO-d6) δ 10.24 (brs, 1H), 8.64 (s, 1H), 8.16 (d, J=6.5 Hz, 1H), 7.47-7.23 (m, 3H), 7.10 (d, J=51.1 Hz, 1H), 6.82 (s, 1H), 6.57 (brs, 2H), 6.37 (d, J=6.2 Hz, 1H), 4.00 (s, 2H), 3.12 (d, J=7.2 Hz, 2H), 2.82 (t, J=7.4 Hz, 2H).

[Example 67]: N-(4-(8-methyl-7-oxo-7,8-dihydro-1,8-naphthyridin-4-yl)benzyl)sulfamide

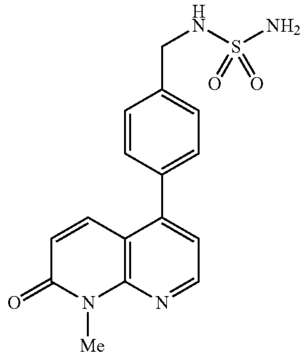 [SMILES: Cn1c(=O)ccc2c(-c3ccc(CNS(N)(=O)=O)cc3)ccnc21]

$^1$H NMR (400 MHz, DMSO-d6) δ 8.68 (d, J=4.9 Hz, 1H), 7.76 (d, J=9.8 Hz, 1H), 7.55 (d, J=8.0 Hz, 2H), 7.46 (d, J=7.9 Hz, 2H), 7.27 (d, J=4.9 Hz, 1H), 6.70 (d, J=9.8 Hz, 1H), 4.18 (s, 2H), 3.73 (s, 3H).

[Reaction Scheme 1-1]

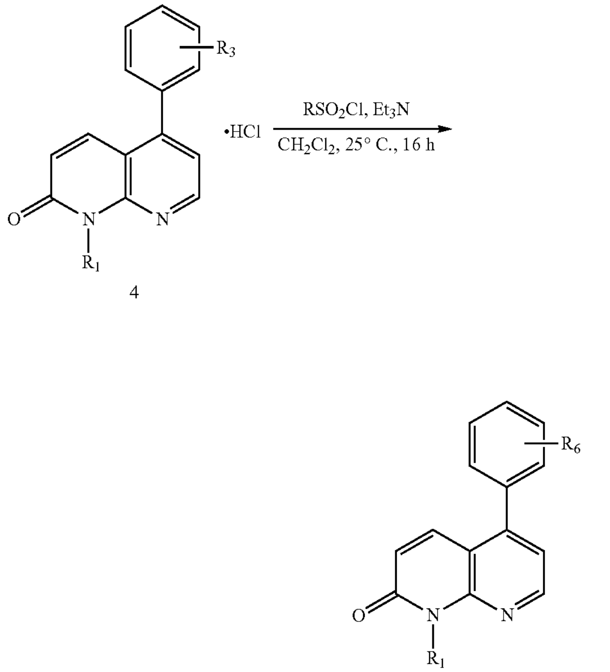

4

9

Step 4: 4 (1.0 equiv.) and $RSO_2Cl$ (1.1 equiv.) were dissolved in dichloromethane (0.08 M) in a round bottom flask. Then, triethylamine (4.5 equiv.) was added thereto, followed by stirring at room temperature for 16 hours. After the reaction was completed, water was poured into the mixture, followed by extraction with dichloromethane. The organic layer was dried over anhydrous magnesium sulfate and concentrated under reduced pressure. The resulting residue was purified by column chromatography (1:20 $MeOH:CH_2Cl_2$) to obtain 9 (30-50% yield).

[Example 68]: N-(4-(7-oxo-7,8-dihydro-1,8-naphthyridin-4-yl)benzyl)methanesulfonamide

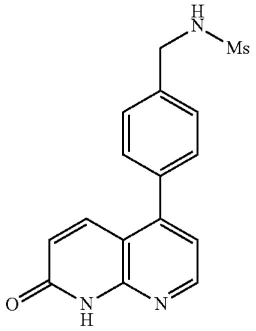 [SMILES: CS(=O)(=O)NCc1ccc(-c2ccnc3[nH]c(=O)ccc23)cc1]

$^1$H NMR (400 MHz, MeOD-d4) δ 8.58 (d, J=5.0 Hz, 1H), 7.95 (d, J=9.8 Hz, 1H), 7.60 (d, J=8.0 Hz, 2H), 7.50 (d, J=8.1 Hz, 2H), 7.25 (d, J=5.0 Hz, 1H), 6.64 (d, J=9.8 Hz, 1H), 4.37 (s, 2H), 2.94 (s, 3H).

[Example 69]: 4-methyl-N-(4-(7-oxo-7,8-dihydro-1,8-naphthyridin-4-yl)benzyl)benzenesulfonamide

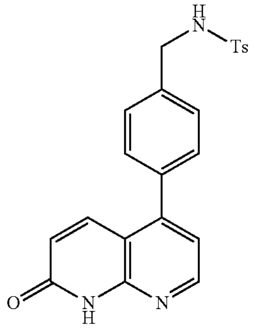 [SMILES: Cc1ccc(S(=O)(=O)NCc2ccc(-c3ccnc4[nH]c(=O)ccc34)cc2)cc1]

$^1$H NMR (400 MHz, MeOD-d4) δ 8.56 (d, J=4.9 Hz, 1H), 7.90 (d, J=9.7 Hz, 1H), 7.74 (d, J=8.2 Hz, 2H), 7.43 (d, J=8.0 Hz, 2H), 7.40-7.34 (m, 4H), 7.20 (d, J=5.0 Hz, 1H), 6.64 (d, J=9.8 Hz, 1H), 4.17 (s, 2H), 2.41 (s, 3H).

[Example 70]: N-(4-(7-oxo-7,8-dihydro-1,8-naphthyridin-4-yl)benzyl)thiophene-2-sulfonamide

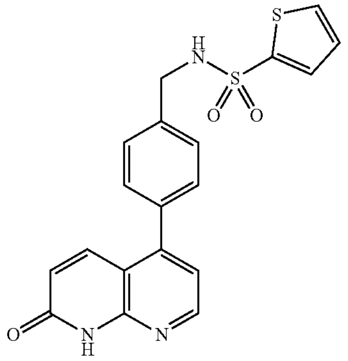 [SMILES: O=c1ccc2c(-c3ccc(CNS(=O)(=O)c4cccs4)cc3)ccnc2[nH]1]

$^1$H NMR (400 MHz, DMSO-d6) δ 8.54 (d, J=5.0 Hz, 1H), 7.91 (d, J=5.0 Hz, 1H), 7.70 (d, J=9.8 Hz, 1H), 7.57 (dd, J=3.8, 1.3 Hz, 1H), 7.48-7.38 (m, 4H), 7.16 (dd, J=8.1, 4.8 Hz, 2H), 6.58 (d, J=9.8 Hz, 1H), 4.18 (s, 2H).

[Example 71]: N-(4-(7-oxo-7,8-dihydro-1,8-naphthyridin-4-yl)benzyl)cyclopropanesulfonamide

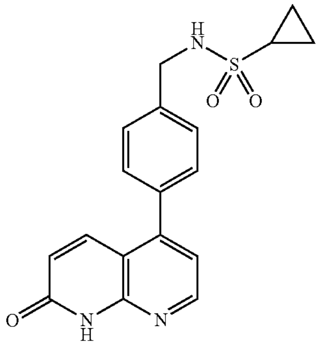 [SMILES: O=c1ccc2c(-c3ccc(CNS(=O)(=O)C4CC4)cc3)ccnc2[nH]1]

$^1$H NMR (400 MHz, MeOD-d4) δ 8.57 (d, J=5.0 Hz, 1H), 7.95 (d, J=9.8 Hz, 1H), 7.61 (d, J=8.0 Hz, 2H), 7.49 (d, J=8.1 Hz, 2H), 7.25 (d, J=5.0 Hz, 1H), 6.64 (d, J=9.8 Hz, 1H), 4.40 (s, 2H), 2.57-2.48 (m, 1H), 1.10-1.04 (m, 2H), 1.01-0.96 (m, 2H).

[Reaction Scheme 1-2]

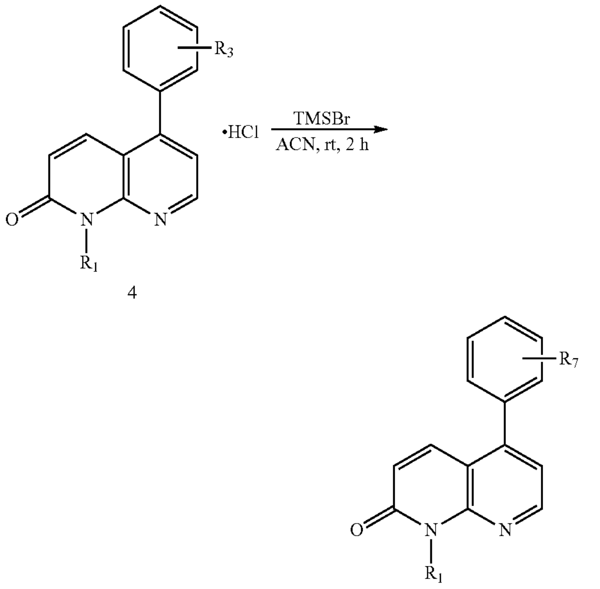

4

10

4 (1.0 equiv.) was dissolved in acetonitrile (0.08 M) in a round bottom flask, and then bromotrimethylsilane (5.0 equiv.) was added thereto at 0° C., followed by stirring at room temperature for 2 hours. The reaction was terminated with methanol, the reaction product was filtered under reduced pressure, and the resulting residue was purified by preparative HPLC to obtain 10 (14-20% yield).

[Example 72]: diethyl(4-(7-oxo-7,8-dihydro-1,8-naphthyridin-4-yl)benzyl)phosphonate

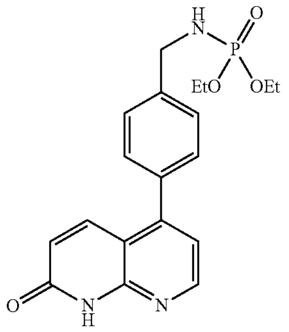 [SMILES: CCOP(=O)(NCc1ccc(-c2ccnc3[nH]c(=O)ccc23)cc1)OCC]

$^1$H NMR (400 MHz, DMSO-d6) δ 12.26 (s, 1H), 8.55 (d, J=4.9 Hz, 1H), 7.75 (d, J=9.8 Hz, 1H), 7.53 (d, J=8.2 Hz, 2H), 7.47 (d, J=8.2 Hz, 2H), 7.19 (d, J=4.9 Hz, 1H), 6.56 (d, J=9.8 Hz, 1H), 5.66-5.46 (m, 1H), 4.07 (dd, J=12.1, 7.3 Hz, 2H), 3.97-3.88 (m, 3H), 1.20 (t, J=7.1 Hz, 6H).

[Example 73]: diethyl(4-(7-oxo-7,8-dihydro-1,8-naphthyridin-4-yl)benzyl)phosphoamidate

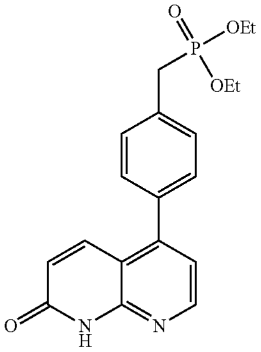 [SMILES: CCOP(=O)(Cc1ccc(-c2ccnc3[nH]c(=O)ccc23)cc1)OCC]

$^1$H NMR (400 MHz, DMSO-d6) δ 12.26 (s, 1H), 8.55 (d, J=4.9 Hz, 1H), 7.75 (d, J=9.8 Hz, 1H), 7.47 (s, 4H), 7.21 (d, J=4.9 Hz, 1H), 6.57 (dd, J=9.8, 2.0 Hz, 1H), 4.00 (dd, J=8.1, 7.1 Hz, 4H), 3.39 (s, 1H), 3.33-3.31 (m, 1H), 1.21 (t, J=7.0 Hz, 6H).

[Example 74]: ethylhydrogen(4-(7-oxo-7,8-dihydro-1,8-naphthyridin-4-yl)benzyl)phosphonate

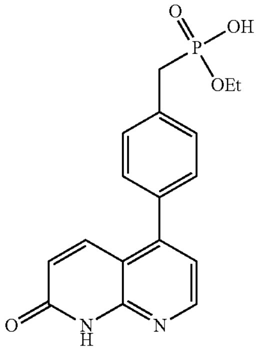 [SMILES: O=c1ccc2c(-c3ccc(CP(=O)(O)O)cc3)ccnc2[nH]1]

$^1$H NMR (400 MHz, DMSO-d6) δ 12.25 (s, 1H), 8.55 (d, J=4.9 Hz, 1H), 7.76 (d, J=9.8 Hz, 1H), 7.55-7.39 (m, 4H), 7.20 (d, J=4.9 Hz, 1H), 6.57 (d, J=9.8 Hz, 1H), 4.04-3.81 (m, 2H), 3.19 (d, J=21.6 Hz, 2H), 1.20 (t, J=7.1 Hz, 4H).

[Example 75]: (4-(7-oxo-7,8-dihydro-1,8-naphthyridin-4-yl)benzyl)phosphonic acid

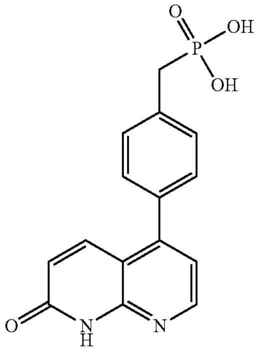

$^1$H NMR (400 MHz, DMSO-d6) δ 12.26 (s, 1H), 8.55 (d, J=4.9 Hz, 1H), 7.78 (d, J=9.8 Hz, 1H), 7.45 (d, J=6.1 Hz, 4H), 7.19 (d, J=4.9 Hz, 1H), 6.57 (d, J=9.8 Hz, 1H), 3.51 (s, 1H), 3.08 (d, J=21.6 Hz, 2H).

Preparation Example 2

Preparation Example 2 includes a process of preparing product 3, product 4, product 7, or product 8.

Preparation Example 2

[Reaction Scheme 2]

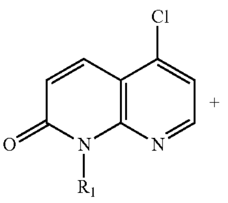

1

-continued

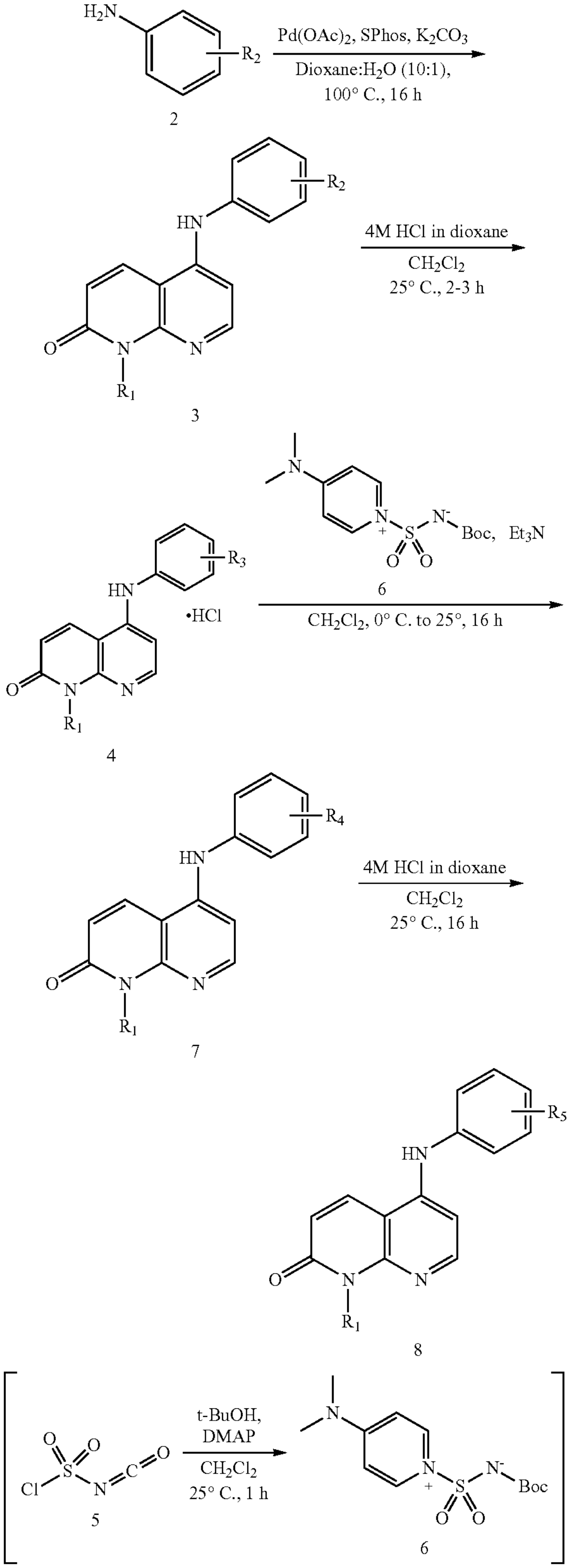

2, 3, 6, 4, 7, 8, 5, 6

Step 1: 1 (1.0 equiv.), palladium (II) acetate (0.050 equiv.), 2-dicyclohexylphosphino-2',6'-dimethoxybiphenyl (0.10 equiv.), 2 (1.3 equiv.) and potassium carbonate (3.0 equiv.) were dissolved in 1,4-dioxane (0.090 M) and water (0.90 M) in a round bottom flask and refluxed under nitrogen for 16 hours. After the reaction was completed, the reaction product was filtered through celite, and the mixture was poured into water, followed by extraction with dichloromethane. The organic layer was dried over anhydrous magnesium sulfate and concentrated under reduced pressure. The resulting residue was purified by column chromatography (1:20 MeOH:$CH_2Cl_2$) to obtain 3 (40-60% yield).

Step 2: 3 (1.0 equiv.) was dissolved in dichloromethane (0.040 M) in a round bottom flask. Then, a hydrochloride solution (4.0 M in 1,4-dioxane, 0.2 M) was added thereto, followed by stirring at room temperature for 4 hours. After the reaction was completed, the reaction product was concentrated under reduced pressure and the residue was washed with diethyl ether, filtered and dried to obtain 4 (60-80% yield).

Examples of the present invention prepared according to step 2 as described above are as follows.

[Example 76]: 5-((3-aminophenyl)amino)-1,8-naphthyridin-2(1H)-one dihydrochloride

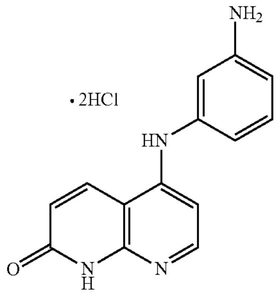 [SMILES: Nc1cccc(Nc2ccnc3[nH]c(=O)ccc23)c1]

$^1$H NMR (400 MHz, DMSO-d6) δ 10.99 (s, 1H), 8.94 (d, J=8.7 Hz, 1H), 8.25 (d, J=7.1 Hz, 1H), 7.56 (t, J=7.9 Hz, 1H), 7.34 (d, J=8.3 Hz, 3H), 7.25 (d, J=7.4 Hz, 1H), 7.17-7.07 (m, 1H), 6.94 (d, J=7.9 Hz, 1H), 6.78 (d, J=7.1 Hz, 1H).

[Example 77]: 5-((3-aminomethyl)phenyl)amino)-1,8-naphthyridin-2(1H)-one dihydrochloride

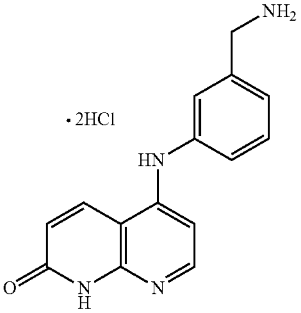 [SMILES: NCc1cccc(Nc2ccnc3[nH]c(=O)ccc23)c1]

$^1$H NMR (400 MHz, DMSO-d6) δ 10.32 (s, 1H), 8.72 (s, 1H), 8.45 (s, 3H), 8.18 (d, J=6.7 Hz, 1H), 7.64-7.46 (m, 2H), 7.45-7.30 (m, 2H), 6.81 (d, J=6.7 Hz, 2H), 4.08 (d, J=5.7 Hz, 2H).

[Example 78]: 5-((3-aminomethyl)-4-fluorophenyl) amino)-1,8-naphthyridin-2(1H)-one dihydrochloride

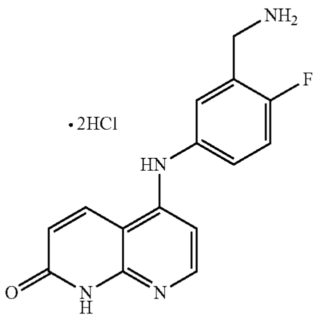 [SMILES: NCc1cc(Nc2ccnc3[nH]c(=O)ccc23)ccc1F]

$^1$H NMR (400 MHz, DMSO-d6) δ 10.00 (s, 1H), 8.63 (s, 1H), 8.13 (d, J=6.5 Hz, 1H), 7.46 (d, J=8.3 Hz, 2H), 7.33 (d, J=8.3 Hz, 2H), 7.13 (s, 1H), 6.68 (s, 2H), 6.63 (d, J=6.5 Hz, 1H), 4.11 (d, J=3.9 Hz, 2H).

[Example 79]: 5-((5-(2-aminoethyl)-2-fluorophenyl) amino)-1,8-naphthyridin-2(1H)-one dihydrochloride

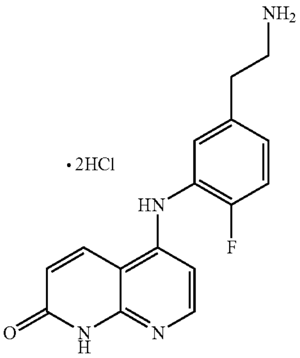 [SMILES: NCCc1ccc(F)c(Nc2ccnc3[nH]c(=O)ccc23)c1]

LC-MS (ESI) calcd for $C_{16}H_{15}FN_4O$ $[M+H]^+$ 298.12, found m/z 299.24.

[Example 80]: 5-((3-(2-methylphenylethyl)phenyl) amino)-1,8-naphthyridin-2(1H)-one dihydrochloride

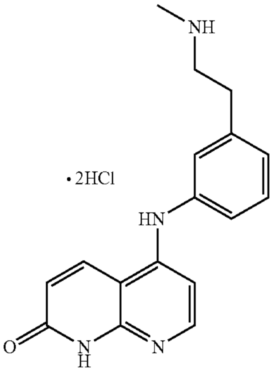 [SMILES: CNCCc1cccc(Nc2ccnc3[nH]c(=O)ccc23)c1]

$^1$H NMR (400 MHz, DMSO-d6) δ 10.66 (s, 1H), 9.05 (s, 2H), 8.85 (s, 1H), 8.19 (d, J=6.8 Hz, 1H), 7.50 (t, J=7.7 Hz, 1H), 7.32 (d, J=12.0 Hz, 2H), 7.27 (d, J=7.5 Hz, 1H), 6.89 (s, 1H), 6.75 (d, J=7.0 Hz, 1H), 3.16 (d, J=3.9 Hz, 2H), 3.06-2.97 (m, 2H), 2.57 (t, J=5.4 Hz, 3H).

[Example 81]: 5-((4-aminophenyl)amino)-1,8-naphthyridin-2(1H)-one dihydrochloride

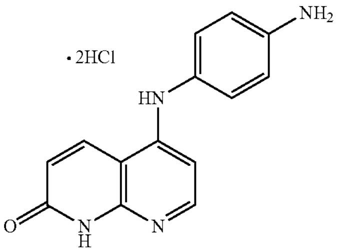 [SMILES: Nc1ccc(Nc2ccnc3[nH]c(=O)ccc23)cc1]

$^1$H NMR (400 MHz, DMSO-d6) δ 10.60 (s, 1H), 8.79 (s, 1H), 8.19 (d, J=6.9 Hz, 1H), 7.39 (d, J=8.5 Hz, 2H), 7.28 (d, J=7.9 Hz, 2H), 6.90 (s, 1H), 6.65 (d, J=7.0 Hz, 1H), 4.04 (s, 4H)

[Example 82]: 5-((4-(aminomethyl)phenyl)amino)-1,8-naphthyridin-2(1H)-one dihydrochloride

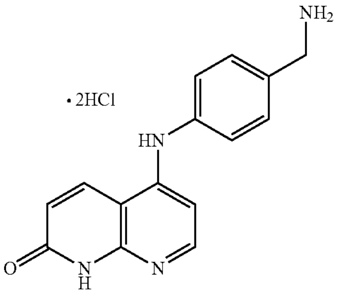 [SMILES: NCc1ccc(Nc2ccnc3[nH]c(=O)ccc23)cc1]

$^1$H NMR (400 MHz, DMSO-d6) δ 10.67 (s, 1H), 8.85 (s, 1H), 8.49 (s, 3H), 8.23 (d, J=6.9 Hz, 1H), 7.64 (d, J=8.4 Hz, 2H), 7.46 (d, J=8.3 Hz, 2H), 6.88 (s, 1H), 6.66 (d, J=6.9 Hz, 1H), 4.07 (d, J=5.7 Hz, 2H).

[Example 83]: 5-((4-((cyclopropylamino)methyl) phenyl)amino)-1,8-naphthyridin-2(1H)-one dihydrochloride

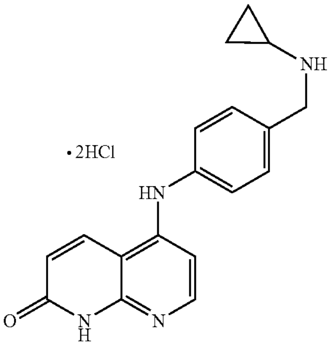 [SMILES: O=c1ccc2c(Nc3ccc(CNC4CC4)cc3)ccnc2[nH]1]

$^1$H NMR (400 MHz, DMSO-d6) δ 9.50 (s, 2H), 8.73 (s, 1H), 8.21 (d, J=6.6 Hz, 1H), 7.68 (d, J=8.3 Hz, 2H), 7.45 (d, J=8.3 Hz, 2H), 6.81 (s, 1H), 6.70 (d, J=6.7 Hz, 1H), 4.25 (s, 2H), 2.68 (s, 1H), 0.92 (t, J=7.8 Hz, 2H), 0.76 (t, J=7.8 Hz, 2H).

[Example 84]: 5-((4-((cyclopropylamino)methyl) phenyl)amino)-1,8-naphthyridin-2(1H)-one dihydrochloride

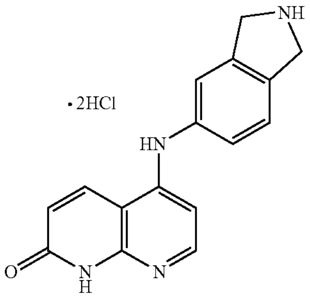 [SMILES: O=c1ccc2c(Nc3ccc4c(c3)CNC4)ccnc2[nH]1]

$^1$H NMR (400 MHz, DMSO-d6) δ 10.58 (s, 1H), 10.04 (s, 2H), 8.81 (s, 1H), 8.20 (d, J=6.7 Hz, 1H), 7.54 (d, J=8.1 Hz, 1H), 7.45 (s, 1H), 7.39 (d, J=8.3 Hz, 1H), 6.86 (s, 1H), 6.69 (d, J=6.9 Hz, 1H), 4.54 (s, 4H).

[Example 85]: 5-((1,2,3,4-tetrahydroisoquinolin-6-yl)amino)-1,8-naphthyridin-2(1H)-one dihydrochloride

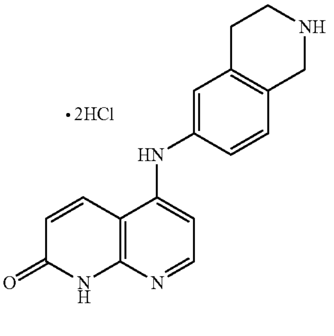 [SMILES: O=c1ccc2c(Nc3ccc4c(c3)CCNC4)ccnc2[nH]1]

$^1$H NMR (400 MHz, DMSO-d6) δ 10.56 (s, 1H), 9.58 (s, 2H), 8.80 (s, 1H), 8.20 (d, J=6.9 Hz, 1H), 7.37 (d, J=8.2 Hz, 1H), 7.29 (d, J=8.8 Hz, 2H), 6.86 (s, 1H), 6.67 (d, J=6.9 Hz, 1H), 4.30 (s, 2H), 3.39-3.35 (m, 2H), 3.06 (t, J=6.1 Hz, 2H).

[Example 86]: 5-((7-fluoro-1,2,3,4-tetrahydroisoquinolin-6-yl)amino)-1,8-naphthyridin-2(1H)-one dihydrochloride

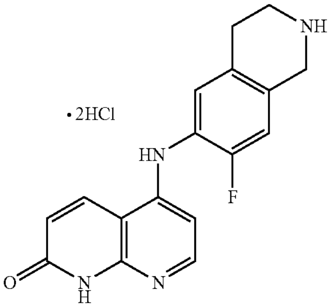 [SMILES: O=c1ccc2c(Nc3cc4c(cc3F)CNCC4)ccnc2[nH]1]

$^1$H NMR (400 MHz, DMSO-d6) δ 10.09 (s, 1H), 9.53 (s, 2H), 8.70 (s, 1H), 8.20 (d, J=6.2 Hz, 1H), 7.48-7.24 (m, 2H), 6.79 (s, 1H), 6.29 (d, J=4.3 Hz, 1H), 4.31 (s, 2H), 3.57 (m, 2H), 3.02 (t, J=6.2 Hz, 2H).

[Example 87]: 5-((2,3,4,5-tetrahydro-1H-benzo[c] azepin-8-yl)amino)-1,8-naphthyridin-2(1H)-one dihydrochloride

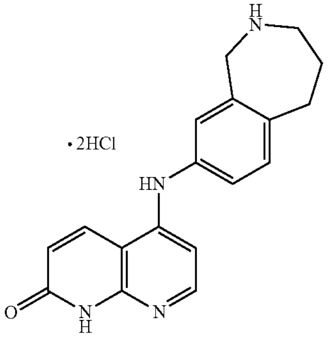 [SMILES: O=c1ccc2c(Nc3ccc4c(c3)CNCCC4)ccnc2[nH]1]

$^1$H NMR (400 MHz, DMSO-d6) δ 10.44 (s, 1H), 9.28 (s, 2H), 8.78 (s, 1H), 8.17 (d, J=6.7 Hz, 1H), 7.45 (s, 1H), 7.39 (d, J=8.1 Hz, 1H), 7.31 (d, J=8.0 Hz, 1H), 6.83 (s, 1H), 6.73 (d, J=6.8 Hz, 1H), 4.34 (s, 2H), 3.37 (s, 2H), 3.03 (d, J=10.1 Hz, 2H), 1.90 (s, 2H).

Step 3: A solution of triethylamine (2.5 equiv.) in dichloromethane (0.1 M) was added to a round bottom flask. Then, 4 (1.0 equiv.) and 6 (1.1 equiv.) were added thereto, followed by stirring at room temperature for one day. After the reaction was completed, the reaction product was concentrated under reduced pressure and dried, and the obtained residue was extracted using dichloromethane and water. The resulting residue was purified through column chromatography (1:20 MeOH:$CH_2Cl_2$) to obtain 7 (30-60% yield).

Step 4: 7 (1.0 equiv.) was dissolved in dichloromethane (0.04 M) in a round bottom flask. Then, a hydrochloride solution (4.0 M in 1,4-dioxane, 0.2M) was added thereto, followed by stirring at room temperature for 16 hours. After the reaction was completed, the reaction product was concentrated under reduced pressure and the resulting residue was washed with diethyl ether, filtered and dried to obtain 8 (40-80% yield).

Examples of the present invention prepared according to step 4 as described above are as follows.

[Example 88]: N-(3-((7-oxo-7,8-dihydro-1,8-naphthyridin-4-yl)amino)phenyl)sulfamide dihydrochloride

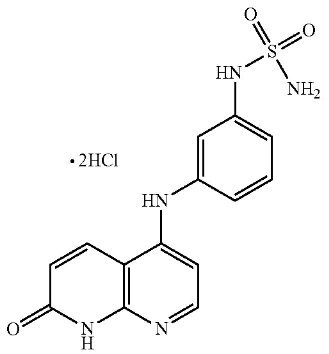 [SMILES: NS(=O)(=O)Nc1cccc(Nc2ccnc3[nH]c(=O)ccc23)c1]

$^1H$ NMR (400 MHz, DMSO-d6) δ 10.58 (s, 1H), 9.82 (s, 1H), 8.77 (s, 1H), 8.20 (d, J=6.9 Hz, 1H), 7.42 (t, J=8.0 Hz, 1H), 7.22 (s, 1H), 7.20 (s, 1H), 7.13 (d, J=8.1 Hz, 1H), 7.01 (d, J=7.8 Hz, 1H), 6.90 (s, 1H), 6.69 (d, J=7.0 Hz, 1H).

[Example 89]: N-(3-((7-oxo-7,8-dihydro-1,8-naphthyridin-4-yl)amino)benzyl)sulfamide dihydrochloride

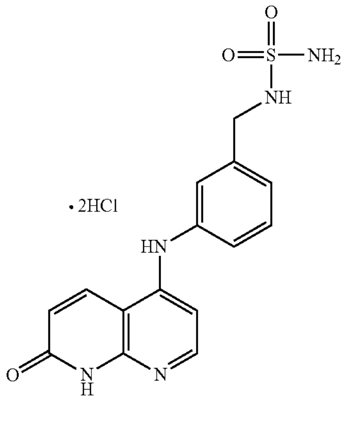 [SMILES: NS(=O)(=O)NCc1cccc(Nc2ccnc3[nH]c(=O)ccc23)c1]

$^1H$ NMR (400 MHz, DMSO-d6) δ 10.46 (s, 1H), 8.76 (s, 1H), 8.17 (d, J=6.8 Hz, 1H), 7.48 (t, J=7.7 Hz, 1H), 7.40 (s, 1H), 7.33 (d, J=7.5 Hz, 1H), 7.29 (d, J=7.5 Hz, 1H), 7.19 (s, 1H), 6.86 (s, 1H), 6.70 (d, J=6.9 Hz, 2H), 4.14 (s, 2H).

[Example 90]: N-(2-fluoro-5((7-oxo-7,8-dihydro-1,8-naphthyridin-4-yl)amino)benzyl)sulfamide dihydrochloride

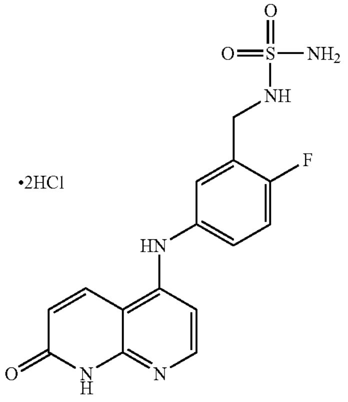 [SMILES: NS(=O)(=O)NCc1cc(Nc2ccnc3[nH]c(=O)ccc23)ccc1F]

$^1H$ NMR (400 MHz, DMSO-d6) δ 9.32 (s, 1H), 8.40 (s, 1H), 8.06 (d, 2H), 8.06 (d, 1H), 7.45 (d, 1H), 7.26 (m, 2H), 7.15 (dd, 1H), 6.72 (s, 2H), 6.60 (d, 1H), 4.15 (d, 2H).

[Example 91]: N-(4-fluoro-3-((7-oxo-7,8-dihydro-1,8-naphthyridin-4-yl)amino)benzyl)sulfamide dihydrochloride

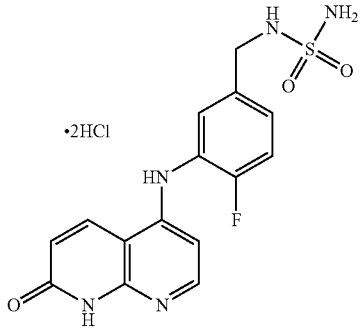 [SMILES: NS(=O)(=O)NCc1ccc(F)c(Nc2ccnc3[nH]c(=O)ccc23)c1]

$^1H$ NMR (400 MHz, DMSO-d6) δ 10.41 (s, 1H), 8.70 (s, 1H), 8.16 (d, J=6.9 Hz, 1H), 7.52 (d, J=6.9 Hz, 1H), 7.34 (d, J=7.5 Hz, 2H), 7.21 (s, 1H), 6.86 (s, 1H), 6.73 (s, 1H), 6.63 (d, J=6.9 Hz, 1H), 4.17 (s, 2H).

[Example 92]: N-(3-((7-oxo-7,8-dihydro-1,8-naphthyridin-4-yl)amino)phenethyl)sulfamide dihydrochloride

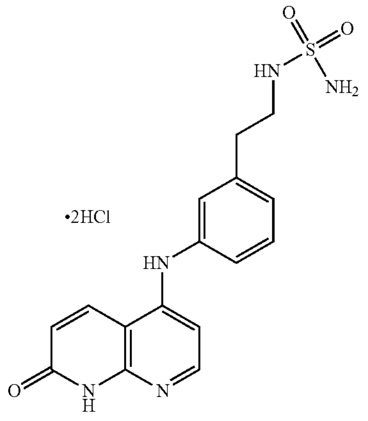 [SMILES: NS(=O)(=O)NCCc1cccc(Nc2ccnc3[nH]c(=O)ccc23)c1]

$^1$H NMR (400 MHz, DMSO-d6) δ 10.71 (s, 1H), 8.85 (s, 1H), 8.17 (d, J=6.8 Hz, 1H), 7.47 (t, J=7.6 Hz, 1H), 7.28 (d, J=14.4 Hz, 3H), 6.93 (s, 1H), 6.73 (d, J=7.0 Hz, 1H), 6.58 (s, 2H), 3.19-3.10 (m, 2H), 2.85 (t, J=7.2 Hz, 2H).

[Example 93]: N-methyl-N-(3-((7-oxo-7,8-dihydro-1,8-naphthyridin-4-yl)amino)phenethyl)sulfamide dihydrochloride

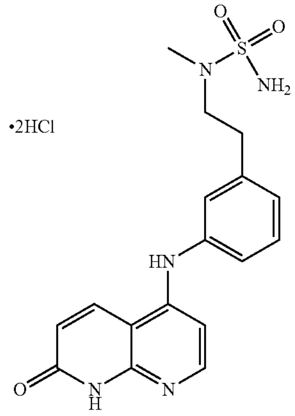 [SMILES: CN(CCc1cccc(Nc2ccnc3[nH]c(=O)ccc23)c1)S(N)(=O)=O]

$^1$H NMR (400 MHz, DMSO-d6) δ 10.58 (s, 1H), 8.78 (d, J=6.7 Hz, 1H), 8.15 (d, J=7.0 Hz, 1H), 7.47 (t, J=7.7 Hz, 1H), 7.34-7.20 (m, 3H), 6.89 (s, 1H), 6.74 (s, 1H), 6.70 (d, J=7.0 Hz, 1H), 3.19 (dd, J=12.6, 4.7 Hz, 2H), 2.90 (t, J=7.4 Hz, 2H), 2.68 (s, 3H)

[Example 94]: N-ethyl-N-(3-((7-oxo-7,8-dihydro-1,8-naphthyridin-4-yl)amino)phenethyl)sulfamide dihydrochloride

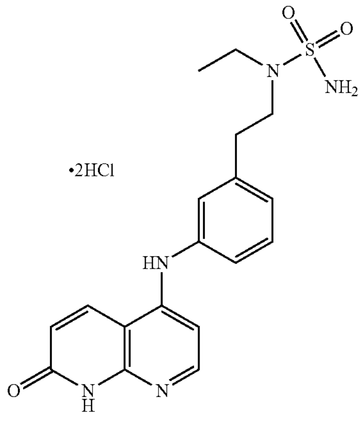 [SMILES: CCN(CCc1cccc(Nc2ccnc3[nH]c(=O)ccc23)c1)S(N)(=O)=O]

$^1$H NMR (400 MHz, DMSO-d6) δ 10.46 (s, 1H), 8.74 (s, 1H), 8.23-8.14 (m, 1H), 7.46 (t, J=7.7 Hz, 1H), 7.29 (s, 1H), 7.25 (d, J=7.6 Hz, 2H), 7.01-6.85 (m, 1H), 6.73 (s, 1H), 6.69 (d, J=6.9 Hz, 1H), 3.33-3.21 (m, 2H), 3.11 (q, J=7.1 Hz, 2H), 2.89 (dd, J=10.1, 5.1 Hz, 2H), 1.06 (t, J=7.1 Hz, 3H).

[Example 95]: N-(4-fluoro-3-((7-oxo-7,8-dihydro-1,8-naphthyridin-4-yl)amino)phenethyl)sulfamide dihydrochloride

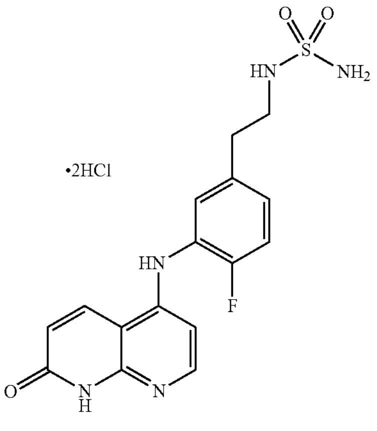 [SMILES: NS(=O)(=O)NCCc1ccc(F)c(Nc2ccnc3[nH]c(=O)ccc23)c1]

$^1$H NMR (400 MHz, MeOD-d4) δ 8.69 (d, J=9.3 Hz, 1H), 8.18 (d, J=7.2 Hz, 1H), 7.44 (d, J=7.5 Hz, 1H), 7.42-7.38 (m, 1H), 7.36-7.29 (m, 1H), 7.04 (d, J=9.4 Hz, 1H), 6.68 (dd, J=7.1, 1.6 Hz, 1H), 3.32-3.28 (m, 2H), 2.93 (t, J=6.8 Hz, 2H).

[Example 96]: N-(4-fluoro-3-((7-oxo-7,8-dihydro-1,8-naphthyridin-4-yl)amino)phenethyl)-N-methylsulfamide dihydrochloride

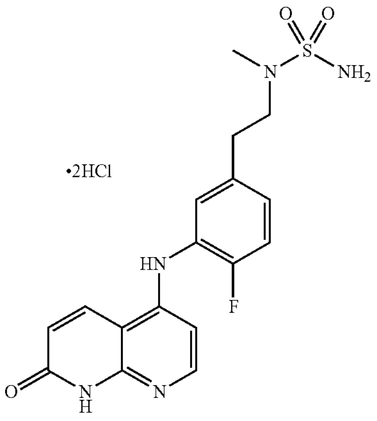 [SMILES: CN(CCc1ccc(F)c(Nc2ccnc3[nH]c(=O)ccc23)c1)S(N)(=O)=O]

LC-MS (ESI) calcd for $C_{17}H_{18}FN_5O_3S$ $[M+H]^+$ 399.11, found m/z 392.35.

[Example 97]: N-(4-((7-oxo-7,8-dihydro-1,8-naphthyridin-4-yl)amino)phenyl)sulfamide dihydrochloride

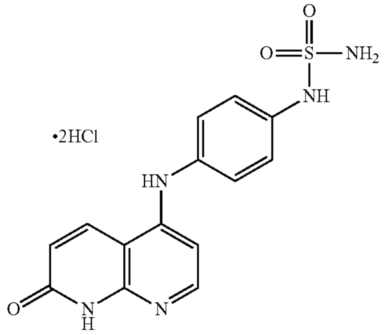 [SMILES: NS(=O)(=O)Nc1ccc(Nc2ccnc3[nH]c(=O)ccc23)cc1]

$^1H$ NMR (400 MHz, DMSO-d6) δ 9.55 (s, 1H), 9.03 (s, 1H), 8.38 (s, 1H), 8.01 (s, 1H), 7.34 (s, 1H), 7.22 (d, 3H), 7.11 (d, 2H), 6.48 (d, 1H).

[Example 98]: N-(4-((7-oxo-7,8-dihydro-1,8-naphthyridin-4-yl)amino)benzyl)sulfamide dihydrochloride

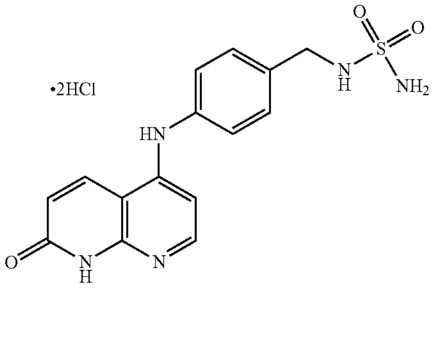 [SMILES: NS(=O)(=O)NCc1ccc(Nc2ccnc3[nH]c(=O)ccc23)cc1]

$^1H$ NMR (400 MHz, DMSO-d6) δ 10.00 (s, 1H), 8.63 (s, 1H), 8.13 (d, J=6.5 Hz, 1H), 7.46 (d, J=8.3 Hz, 2H), 7.33 (d, J=8.3 Hz, 2H), 7.13 (s, 1H), 6.68 (s, 2H), 6.63 (d, J=6.5 Hz, 1H), 4.11 (d, J=3.9 Hz, 2H).

[Example 99]: N-cyclopropyl-N-(4-((7-oxo-7,8-dihydro-1,8-naphthyridin-4-yl)amino)benzyl)sulfamide dihydrochloride

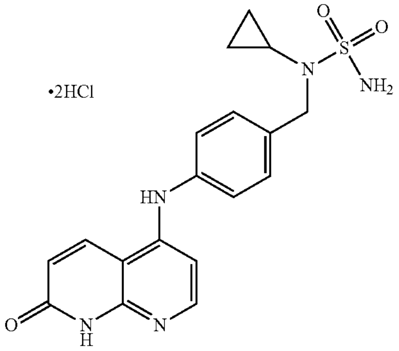 [SMILES: NS(=O)(=O)N(Cc1ccc(Nc2ccnc3[nH]c(=O)ccc23)cc1)C1CC1]

$^1H$ NMR (400 MHz, DMSO-d6) δ 10.50 (s, 1H), 8.76 (d, J=9.1 Hz, 1H), 8.18 (d, J=6.6 Hz, 1H), 7.48 (d, J=8.3 Hz, 2H), 7.36 (d, J=8.3 Hz, 2H), 7.15 (d, J=51.0 Hz, 1H), 7.01 (s, 2H), 6.88 (d, J=8.7 Hz, 1H), 6.66 (d, J=6.9 Hz, 1H), 4.32 (s, 2H), 2.41-2.21 (m, 1H), 0.58 (dd, J=6.6, 5.1 Hz, 4H).

[Example 100]: N-(3-chloro-4-((7-oxo-7,8-dihydro-1,8-naphthyridin-4-yl)amino)benzyl)sulfamide dihydrochloride

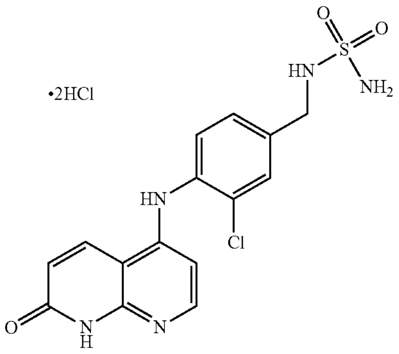 [SMILES: NS(=O)(=O)NCc1ccc(Nc2ccnc3[nH]c(=O)ccc23)c(Cl)c1]

$^1H$ NMR (400 MHz, DMSO-d6) δ 10.30 (s, 1H), 8.80 (d, J=9.1 Hz, 1H), 8.17 (d, J=6.5 Hz, 1H), 7.69 (s, 1H), 7.49 (s, 2H), 7.44 (s, 1H), 7.31-7.27 (m, 1H), 7.18 (s, 1H), 6.86 (d, J=9.3 Hz, 1H), 6.74 (s, 1H), 6.10 (d, J=6.7 Hz, 1H), 4.17 (s, 2H).

[Example 101]: 5-((7-oxo-7,8-dihydro-1,8-naphthyridin-4-yl)amino)isoindolin-2-yl)sulfamide dihydrochloride

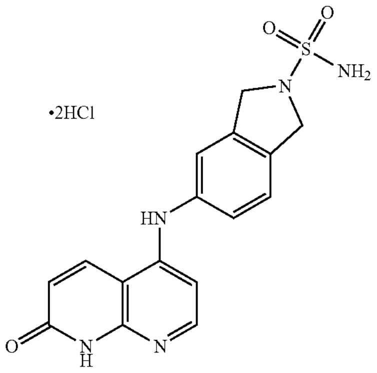 [SMILES: NS(=O)(=O)N1Cc2ccc(Nc3ccnc4[nH]c(=O)ccc34)cc2C1]

$^1$H NMR (400 MHz, DMSO-d6) δ 8.64 (s, 1H), 8.15 (d, J=5.6 Hz, 1H), 7.46 (d, J=7.9 Hz, 1H), 7.36 (s, 1H), 7.30 (d, J=8.2 Hz, 1H), 6.99 (s, 1H), 6.65 (d, J=6.7 Hz, 1H), 4.54 (s, 4H).

[Example 102]: 7-((7-oxo-7,8-dihydro-1,8-naphthyridin-4-yl)amino)-3,4-dihydroisoquinolin-2(1H)-yl) sulfamide dihydrochloride

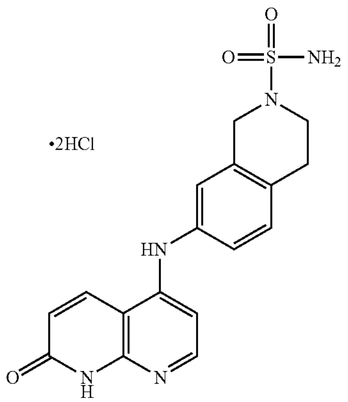 [SMILES: NS(=O)(=O)N1CCc2ccc(Nc3ccnc4[nH]c(=O)ccc34)cc2C1]

$^1$H NMR (400 MHz, DMSO-d6) δ 10.70 (s, 1H), 8.83 (d, J=8.1 Hz, 1H), 8.17 (d, J=7.0 Hz, 1H), 7.34 (d, J=7.9 Hz, 1H), 7.23 (d, J=8.1 Hz, 2H), 6.99 (s, 2H), 6.92 (d, J=8.0 Hz, 1H), 6.67 (d, J=7.1 Hz, 1H), 4.25 (s, 2H), 3.31 (t, J=5.8 Hz, 2H), 2.96 (t, J=5.8 Hz, 2H).

[Example 103]: (8-((7-oxo-7,8-dihydro-1,8-naphthyridin-4-yl)amino)-1,3,4,5-tetrahydro-2 (1H)-benzo [c]azepin-2-yl)sulfamide dihydrochloride

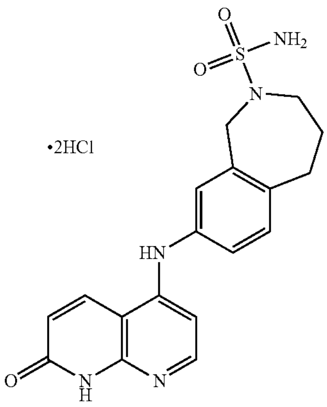 [SMILES: NS(=O)(=O)N1CCCc2ccc(Nc3ccnc4[nH]c(=O)ccc34)cc2C1]

$^1$H NMR (400 MHz, DMSO-d6) δ 10.58 (s, 1H), 8.79 (d, J=8.7 Hz, 1H), 8.17 (d, J=7.0 Hz, 1H), 7.33 (d, J=8.0 Hz, 1H), 7.22 (dd, J=11.8, 3.8 Hz, 2H), 6.89 (s, 1H), 6.79 (s, 1H), 6.69 (d, J=7.0 Hz, 1H), 4.32 (s, 2H), 3.50 (s, 2H), 2.99 (d, J=9.9 Hz, 2H), 1.82 (s, 2H).

[Example 104]: (6-((7-oxo-7,8-dihydro-1,8-naphthyridin-4-yl)amino)-3,4-dihydroisoquinolin-2(1H)-yl) sulfamide dihydrochloride

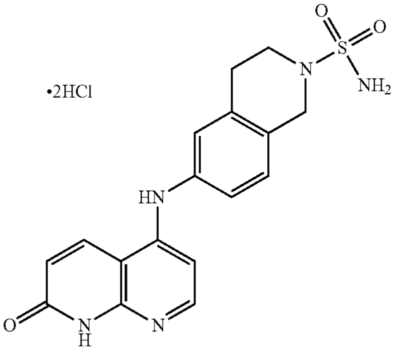 [SMILES: NS(=O)(=O)N1CCc2cc(Nc3ccnc4[nH]c(=O)ccc34)ccc2C1]

$^1$H NMR (400 MHz, DMSO-d6) δ 10.47 (s, 1H), 8.77 (s, 1H), 8.16 (d, J=6.9 Hz, 1H), 7.37 (d, J=25.5 Hz, 1H), 7.29 (d, J=17.5 Hz, 1H), 7.14- (t, J=17.2 Hz, 2H), 6.97 (s, 1H), 6.83 (s, 1H), 6.67 (d, J=6.9 Hz, 1H), 4.25 (s, 2H), 3.32-3.28 (m, 2H), 2.96 (t, J=5.5 Hz, 2H).

[Example 105]: 6-fluoro-7-((7-oxo-7,8-dihydro-1,8-naphthyridin-4-yl)amino)-3,4-dihydroisoquinoline-2(1H)-yl)sulfamide dihydrochloride

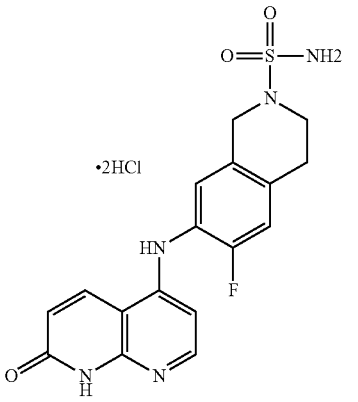 [SMILES: NS(=O)(=O)N1CCc2cc(F)c(Nc3ccnc4[nH]c(=O)ccc34)cc2C1]

LC-MS (ESI) calcd for $C_{17}H_{16}FN_5O_3S$ [M+H]$^+$ 389.10, found m/z 390.23.

[Example 106]: (7-fluoro-6-((7-oxo-7,8-dihydro-1,8-naphthyridin-4-yl)amino)-3,4-dihydroisoquinolin-2(1H)-yl) sulfamide dihydrochloride

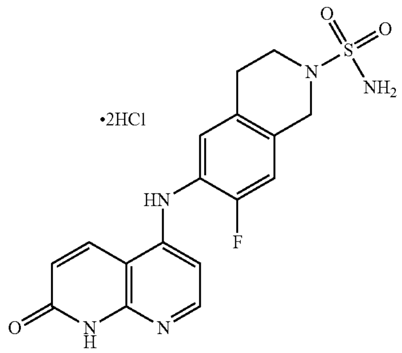 [SMILES: NS(=O)(=O)N1CCc2cc(Nc3ccnc4[nH]c(=O)ccc34)c(F)cc2C1]

$^1$H NMR (400 MHz, DMSO-d6) δ 10.39 (s, 1H), 8.76 (d, J=6.4 Hz, 1H), 8.19 (d, J=6.9 Hz, 1H), 7.37 (d, J=11.0 Hz, 1H), 7.31 (d, J=7.8 Hz, 1H), 7.00 (s, 1H), 6.90 (s, 1H), 6.36 (dd, J=6.7, 2.1 Hz, 1H), 4.27 (s, 2H), 3.30 (t, J=5.8 Hz, 2H), 2.94 (d, J=5.1 Hz, 2H).

[Example 107]: N-(5-((7-oxo-7,8-dihydro-1,8-naphthyridin-4-yl)amino)-2,3-dihydro-1H-inden-2-yl) sulfamide dihydrochloride

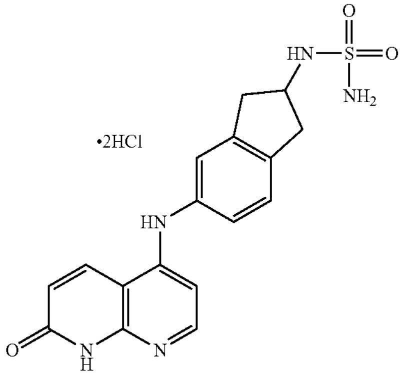 [SMILES: NS(=O)(=O)NC1Cc2ccc(Nc3ccnc4[nH]c(=O)ccc34)cc2C1]

$^1$H NMR (400 MHz, DMSO-d6) δ 10.46 (s, 1H), 8.75 (s, 1H), 8.15 (d, J=6.9 Hz, 1H), 7.35 (d, J=7.9 Hz, 1H), 7.23 (s, 1H), 7.16 (d, J=7.7 Hz, 1H), 6.98 (s, 1H), 6.89 (s, 1H), 6.61 (d, J=6.9 Hz, 2H), 4.23-4.04 (m, 1H), 3.23 (dd, J=15.8, 6.9 Hz, 2H), 3.03-2.80 (m, 2H).

[Example 108]: (7-(methyl(7-oxo-7,8-dihydro-1,8-naphthyridin-4-yl)amino)-3,4-dihydroisoquinolin-2(1H)-yl)sulfamide dihydrochloride

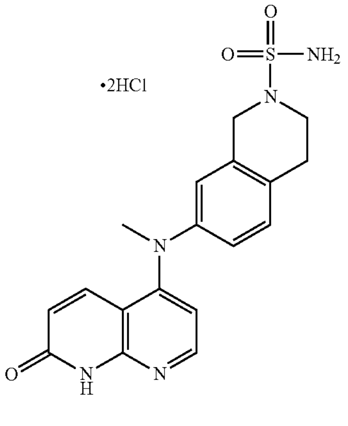 [SMILES: CN(c1ccc2c(c1)CN(S(N)(=O)=O)CC2)c1ccnc2[nH]c(=O)ccc12]

$^1$H NMR (400 MHz, DMSO-d6) δ 8.42 (d, J=5.9 Hz, 1H), 7.37 (d, J=9.8 Hz, 1H), 7.18 (d, J=8.3 Hz, 1H), 7.09 (s, 1H), 7.02 (d, J=6.2 Hz, 1H), 6.97 (d, J=7.6 Hz, 1H), 6.92 (s, 2H), 6.42 (d, J=9.0 Hz, 1H), 4.15 (s, 3H), 3.49 (s, 3H), 3.27 (s, 2H), 2.90 (s, 2H).

Preparation Example 3

Preparation Example 3 includes a process of preparing product 3, product 4, product 7, or product 8.

Preparation Example 3

[Reaction Scheme 3]

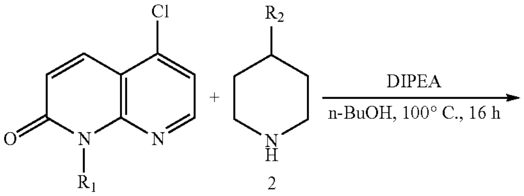

1 2

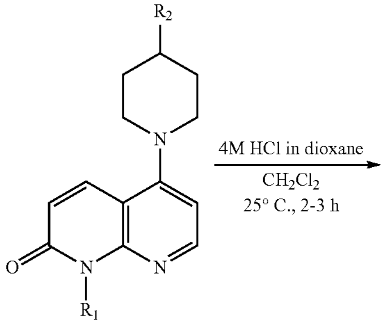

3

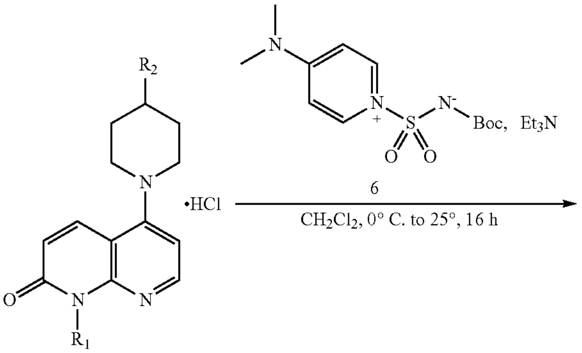

4

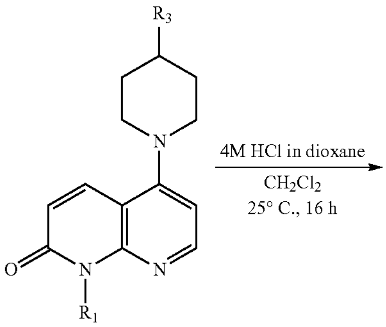

7

-continued

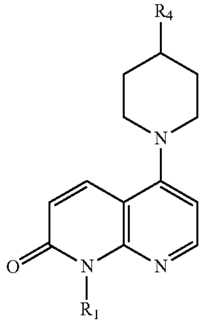

8

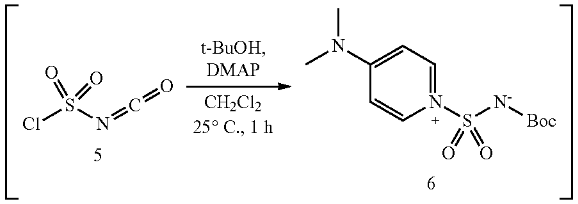

Step 1: 1 (1.0 equiv.), 2 (1.3 equiv.), and N,N-diisopropylethylamine (3.0 equiv.) were dissolved in n-butanol (0.1 M) in a round bottom flask, followed by refluxing for 16 hours. After the reaction was completed, the reaction product was cooled to room temperature, followed by filtering the precipitated solid to obtain 3, or water was poured into the mixture, followed by extraction with dichloromethane. The organic layer was dried over anhydrous magnesium sulfate and concentrated under reduced pressure. The obtained residue was purified by column chromatography (1:10 MeOH:$CH_2C_{12}$) to obtain 3 (40-60% yield).

[Example 109]: tert-butyl(1-(7-oxo-7,8-dihydro-1,8-naphthyridin-4-yl)piperidin-4-yl)carbamate

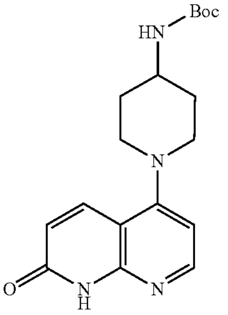 [SMILES: CC(C)(C)OC(=O)NC1CCN(c2ccnc3[nH]c(=O)ccc23)CC1]

$^1$H NMR (400 MHz, DMSO-d6) δ 11.90 (s, 1H), 8.26 (d, J=5.5 Hz, 1H), 7.79 (d, J=9.7 Hz, 1H), 6.96 (d, J=7.6 Hz, 1H), 6.75 (d, J=5.6 Hz, 1H), 6.46 (d, J=9.7 Hz, 1H), 2.89 (t, J=11.8 Hz, 2H), 1.88 (d, J=13.9 Hz, 2H), 1.70-1.54 (m, 3H), 1.40 (s, 9H).

[Example 110]: tert-butyl((1-(7-oxo-7,8-dihydro-1,8-naphthyridin-4-yl)piperidin-4-yl)methyl)carbamate

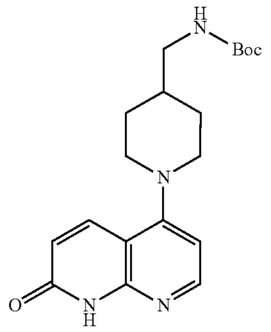 [SMILES: CC(C)(C)OC(=O)NCC1CCN(c2ccnc3[nH]c(=O)ccc23)CC1]

$^1$H NMR (400 MHz, MeOD-d6) δ 8.29 (d, J=5.6 Hz, 1H), 8.02 (dd, J=9.8, 1.2 Hz, 1H), 6.82 (d, J=5.7 Hz, 1H), 6.57 (d, J=9.7 Hz, 1H), 3.57 (d, J=12.5 Hz, 2H), 3.04 (d, J=6.6 Hz, 2H), 2.91 (t, J=12.1 Hz, 2H), 1.87 (d, J=15.7 Hz, 2H), 1.77-1.63 (m, 1H), 1.55-1.47 (m, 2H), 1.45 (s, 9H).

[Example 111]: tert-butyl(2-(1-(7-oxo-7,8-dihydro-1,8-naphthyridin-4-yl)piperidin-4-yl)ethyl) carbamate

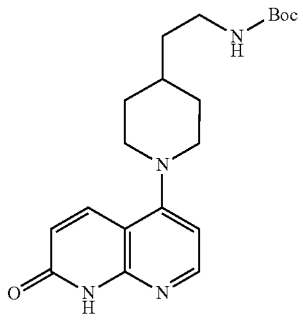 [SMILES: CC(C)(C)OC(=O)NCCC1CCN(c2ccnc3[nH]c(=O)ccc23)CC1]

$^1$H NMR (400 MHz, DMSO-d6) δ 11.87 (s, 1H), 8.25 (d, J=5.5 Hz, 1H), 7.81 (d, J=9.7 Hz, 1H), 6.81 (t, J=5.4 Hz, 1H), 6.74 (d, J=5.6 Hz, 1H), 6.44 (d, J=9.7 Hz, 1H), 3.41 (d, J=12.2 Hz, 2H), 3.00 (q, J=6.6 Hz, 2H), 2.80 (t, J=11.8 Hz, 2H), 1.79 (d, J=12.2 Hz, 2H), 1.53-1.33 (m, 14H).

[Example 112]: tert-butyl((1-(8-methyl-7-oxo-7,8-dihydro-1,8-naphthyridin-4-yl)piperidin-4-yl)methyl)carbamate

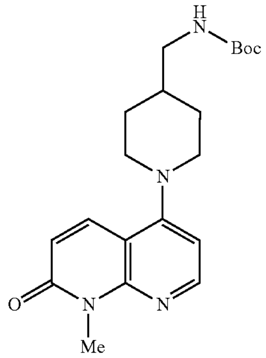 [SMILES: Cn1c(=O)ccc2c(N3CCC(CNC(=O)OC(C)(C)C)CC3)ccnc21]

$^1$H NMR (400 MHz, DMSO-d6) δ 8.39 (d, J=5.5 Hz, 1H), 7.84 (d, J=9.8 Hz, 1H), 6.92 (t, J=5.8 Hz, 1H), 6.85 (d, J=5.6 Hz, 1H), 6.59 (d, J=9.7 Hz, 1H), 3.64 (s, 3H), 3.42 (d, J=11.3 Hz, 2H), 2.91 (t, J=6.3 Hz, 2H), 2.82 (t, J=11.9 Hz, 2H), 1.76 (d, J=12.8 Hz, 2H), 1.64-1.51 (m, 1H), 1.44-1.34 (m, 11H).

Step 2: 3 (1.0 equiv.) was dissolved in dichloromethane (0.040 M) in a round bottom flask. Then, a hydrochloride solution (4.0 M in 1,4-dioxane, 0.2 M) was added thereto, followed by stirring at room temperature for 4 hours. After the reaction was completed, the reaction mixture was concentrated under reduced pressure, was washed with diethyl ether, filtered and dried to obtain 4 (60-80% yield).

[Example 113]: 5-(4-aminopiperidin-1-yl)-1,8-naphthyridin-2(1H)-one hydrochloride

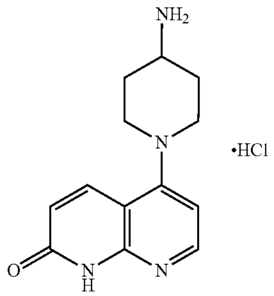 [SMILES: NC1CCN(c2ccnc3[nH]c(=O)ccc23)CC1 ; Cl]

$^1$H NMR (400 MHz, DMSO-d6) δ 8.30 (d, J=6.0 Hz, 1H), 8.17 (s, 3H), 7.91 (s, 1H), 6.87 (d, J=6.0 Hz, 1H), 6.58 (s, 1H), 3.69-3.58 (m, 4H), 3.15-2.97 (m, 2H), 2.06 (d, J=12.1 Hz, 2H), 1.84-1.69 (m, 2H).

[Example 114]: 5-(4-(aminomethyl)piperidin-1-yl)-1,8-naphthyridin-2(1H)-one hydrochloride

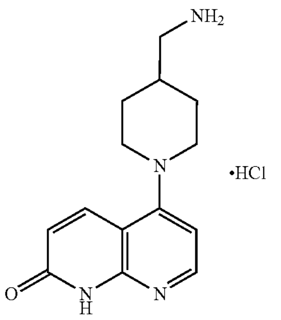 [SMILES: NCC1CCN(c2ccnc3[nH]c(=O)ccc23)CC1 ; Cl]

$^1$H NMR (400 MHz, MeOD-d4) δ 8.27-8.22 (m, 2H), 7.04 (d, J=7.0 Hz, 1H), 6.86 (d, J=9.4 Hz, 1H), 4.10 (d, J=13.1 Hz, 2H), 3.41 (t, J=12.7 Hz, 2H), 2.96 (d, J=6.9 Hz, 2H), 2.13-2.05 (m, 1H), 2.06-1.97 (m, 2H), 1.67-1.54 (m, 2H).

[Example 115]: 5-(4-(2-aminoethyl)piperidin-1-yl)-1,8-naphthyridin-2(1H)-one hydrochloride

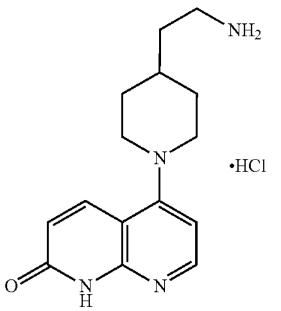 [SMILES: NCCC1CCN(c2ccnc3[nH]c(=O)ccc23)CC1 ; Cl]

$^1$H NMR (400 MHz, MeOD-d4) δ 8.22 (dd, J=8.2, 5.6 Hz, 2H), 7.01 (d, J=7.0 Hz, 1H), 6.83 (d, J=9.5 Hz, 1H), 4.06 (d, J=13.1 Hz, 2H), 3.38 (t, J=13.3 Hz, 2H), 3.04 (t, J=7.9 Hz, 2H), 1.97 (d, J=13.0 Hz, 2H), 1.89-1.78 (m, 1H), 1.71 (dt, J=9.9, 7.1 Hz, 2H), 1.62-1.47 (m, 2H).

[Example 116]: 5-(1,4-diazepan-1-yl)-1,8-naphthyridin-2(1H)-one hydrochloride

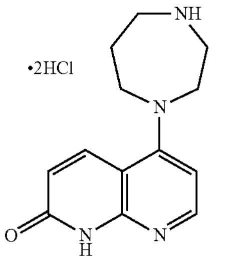 [SMILES: O=c1ccc2c(N3CCCNCC3)ccnc2[nH]1]

$^1$H NMR (400 MHz, DMSO-d6) δ 9.45 (s, 2H), 8.26 (d, J=6.9 Hz, 2H), 6.90 (d, J=7.0 Hz, 1H), 6.71 (s, 1H), 4.03 (s, 2H), 3.88 (s, 2H), 3.42 (s, 2H), 3.21 (s, 2H), 2.21 (s, 2H).

[Example 117]: 5-(2,8-diazaspiro[4,5]decan-8-yl)-1,8-naphthyridin-2(1H)-one hydrochloride

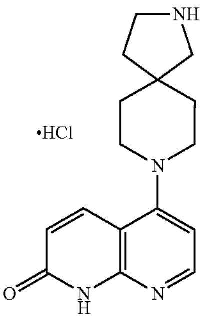 [SMILES: O=c1ccc2c(N3CCC4(CCNC4)CC3)ccnc2[nH]1 ; Cl]

$^1$H NMR (400 MHz, MeOD-d4) δ 8.29 (d, J=9.5 Hz, 1H), 8.24 (d, J=7.2 Hz, 1H), 7.07 (d, J=7.2 Hz, 1H), 6.89 (d, J=9.5 Hz, 1H), 3.88-3.73 (m, 4H), 3.47 (t, J=7.4 Hz, 2H), 3.26 (s, 2H), 2.11 (t, J=7.5 Hz, 2H), 2.02-1.89 (m, 4H).

[Example 118]: 5-(4-(aminomethyl)piperidin-1-yl)-1-methyl-1,8-naphthyridin-2(1H)-one hydrochloride

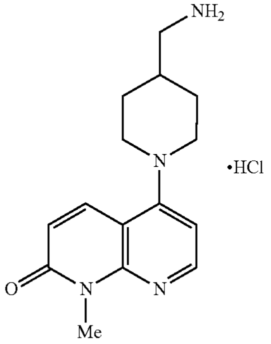 [SMILES: Cn1c(=O)ccc2c(N3CCC(CN)CC3)ccnc21 ; Cl]

$^1$H NMR (400 MHz, MeOD-d4) δ 8.20 (d, J=6.9 Hz, 1H), 7.98 (d, J=9.9 Hz, 1H), 7.12 (d, J=6.9 Hz, 1H), 6.70 (d, J=9.9 Hz, 1H), 4.01 (d, J=13.1 Hz, 2H), 3.76 (s, 3H), 3.42-3.34 (m, 2H), 2.96 (d, J=6.8 Hz, 2H), 2.12-2.04 (m, 1H), 2.01 (d, J=13.0 Hz, 2H), 1.67-1.51 (m, 2H).

[Preparation of sulfamide 6]: A solution of tert-butanol (1.0 equiv.) in anhydrous dichloromethane (1.4 M) was added to a round bottom flask and 5 (1.0 equiv.) was slowly added dropwise thereto. Then, N,N-dimethylpyridin-4-amine (2.0 equiv.) was added thereto. The solution was stirred at room temperature for 1 hour. After the reaction was complete, the reaction product was washed several times with water. The organic layer was dried over anhydrous sodium sulfate and concentrated in vacuo. The obtained colorless powder 6 (80% yield) was used as a reactant without further purification.

Step 3: A solution of 4 (1.0 equiv.) and triethylamine (2.5 equiv.) in dichloromethane (0.1 M) was added to a round bottom flask. Then, 6 (1.1 equiv.) was added thereto, followed by stirring at room temperature for one day. After the reaction was completed, the reaction product was concentrated under reduced pressure and dried, and the obtained residue was extracted using dichloromethane and water. The resulting residue was purified through column chromatography (1:20 MeOH:$CH_2Cl_2$) to obtain 7 (30-60% yield).

[Example 119]: tert-butyl(N-(1-(7-oxo-7,8-dihydro-1,8-naphthyridin-4-yl)piperidin-4-yl) sulfamoyl) carbamate

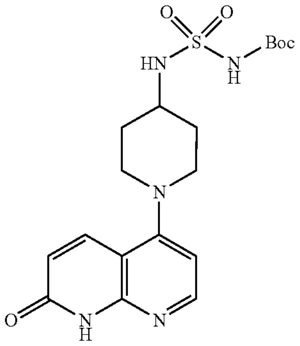 [SMILES: CC(C)(C)OC(=O)NS(=O)(=O)NC1CCN(c2ccnc3[nH]c(=O)ccc23)CC1]

$^1$H NMR (400 MHz, MeOD-d4) δ 8.30 (d, J=5.6 Hz, 1H), 8.03 (d, J=9.7 Hz, 1H), 6.84 (d, J=5.6 Hz, 1H), 6.59 (d, J=9.7 Hz, 1H), 3.57-3.41 (m, 3H), 3.03 (t, J=11.7 Hz, 2H), 2.13 (d, J=13.2 Hz, 2H), 1.92-1.76 (m, 2H), 1.48 (s, 9H).

[Example 120]: tert-butyl(N-((1-(7-oxo-7,8-dihydro-1,8-naphthyridin-4-yl)piperidin-4-yl)methyl)sulfamoyl)carbamate

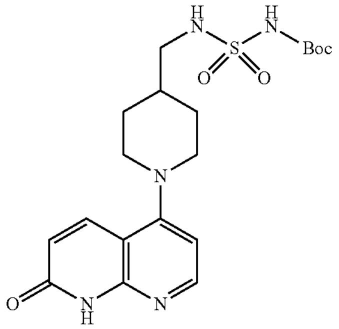 [SMILES: CC(C)(C)OC(=O)NS(=O)(=O)NCC1CCN(c2ccnc3[nH]c(=O)ccc23)CC1]

$^1$H NMR (400 MHz, DMSO-d6) δ 11.88 (s, 1H), 8.25 (d, J=5.5 Hz, 1H), 7.81 (d, J=9.7 Hz, 1H), 6.75 (d, J=5.6 Hz, 1H), 6.44 (d, J=9.7 Hz, 1H), 3.41-3.37 (m, 4H), 2.87-2.70 (m, 4H), 1.81 (d, J=12.8 Hz, 2H), 1.68-1.58 (m, 1H), 1.37 (s, 9H).

[Example 121]: tert-butyl(N-(2-(1-(7-oxo-7,8-dihydro-1,8-naphthyridin-4-yl)piperidin-4-yl)ethyl) sulfamoyl) carbamate

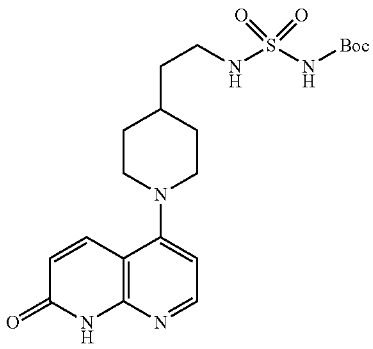 [SMILES: CC(C)(C)OC(=O)NS(=O)(=O)NCCC1CCN(c2ccnc3[nH]c(=O)ccc23)CC1]

$^1$H NMR (400 MHz, MeOD-d4) δ 8.29 (d, J=5.6 Hz, 1H), 8.02 (d, J=9.7 Hz, 1H), 6.82 (d, J=5.7 Hz, 1H), 6.57 (d, J=9.7 Hz, 1H), 3.61-3.51 (m, 2H), 3.09 (t, J=7.0 Hz, 2H), 2.94 (t, J=12.0 Hz, 2H), 1.91 (d, J=8.0 Hz, 2H), 1.73-1.65 (m, 1H), 1.60 (q, J=6.9 Hz, 2H), 1.56-1.50 (m, 2H), 1.48 (s, 9H).

[Example 122]: tert-butyl(N-((1-(8-methyl-7-oxo-7,8-dihydro-1,8-naphthyridin-4-yl)piperidin-4-yl) methyl)sulfamoyl)carbamate

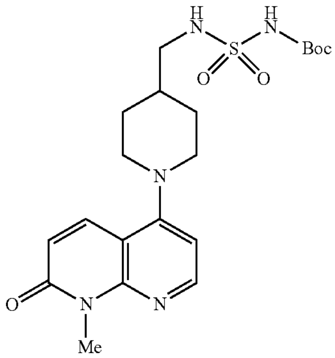 [SMILES: Cn1c(=O)ccc2c(N3CCC(CNS(=O)(=O)NC(=O)OC(C)(C)C)CC3)ccnc21]

$^1$H NMR (400 MHz, MeOD-d4) δ 8.44 (d, J=5.7 Hz, 1H), 8.04 (d, J=9.7 Hz, 1H), 6.92 (d, J=5.8 Hz, 1H), 6.68 (d, J=9.7 Hz, 1H), 3.82 (s, 3H), 3.60-3.54 (m, 2H), 3.02 (d, J=6.7 Hz, 2H), 2.95 (t, J=12.0 Hz, 2H), 1.98 (d, J=13.0 Hz, 2H), 1.87-1.76 (m, 1H), 1.62-1.48 (m, 11H).

Step 4: 7 (1.0 equiv.) was dissolved in dichloromethane (0.04 M) in a round bottom flask. Then, a hydrochloride solution (4.0 M in 1,4-dioxane, 0.2M) was added thereto, followed by stirring at room temperature for 16 hours. After the reaction was completed, the reaction product was concentrated under reduced pressure and the resulting residue was washed with diethyl ether, filtered and dried to obtain 8 (40-80% yield).

[Example 123]: N-(1-(7-oxo-7,8-dihydro-1,8-naphthyridin-4-yl)piperidin-4-yl)sulfamide

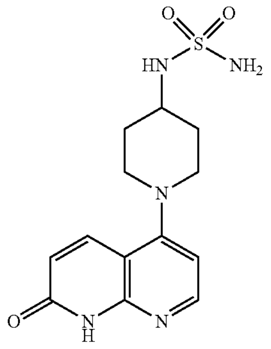 [SMILES: NS(=O)(=O)NC1CCN(c2ccnc3[nH]c(=O)ccc23)CC1]

$^1$H NMR (400 MHz, MeOD-d4) δ 8.29 (d, J=9.4 Hz, 1H), 8.20 (d, J=7.3 Hz, 1H), 7.07 (d, J=7.3 Hz, 1H), 6.91 (d, J=9.3 Hz, 1H), 4.12 (d, J=13.7 Hz, 2H), 3.72-3.54 (m, 3H), 2.31-2.19 (m, 2H), 1.91-1.74 (m, 2H).

[Example 124]: N-((1-(7-oxo-7,8-dihydro-1,8-naphthyridin-4-yl)piperidin-4-yl)methyl)sulfamide

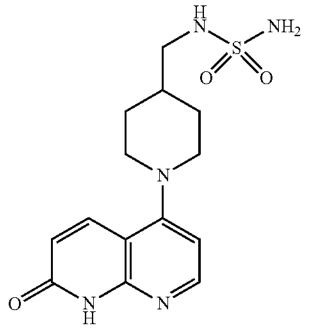 [SMILES: NS(=O)(=O)NCC1CCN(c2ccnc3[nH]c(=O)ccc23)CC1]

$^1$H NMR (400 MHz, MeOD-d4) δ 8.21 (dd, J=13.9, 8.1 Hz, 2H), 6.99 (d, J=7.0 Hz, 1H), 6.82 (d, J=9.4 Hz, 1H), 4.05 (d, J=13.1 Hz, 2H), 3.38 (d, J=13.4 Hz, 2H), 3.02 (d, J=6.3 Hz, 2H), 2.08-1.90 (m, 3H), 1.53 (q, J=12.3 Hz, 2H).

[Example 125]: N-(2-(1-(7-oxo-7,8-dihydro-1,8-naphthyridin-4-yl)piperidin-4-yl)ethyl)sulfamide

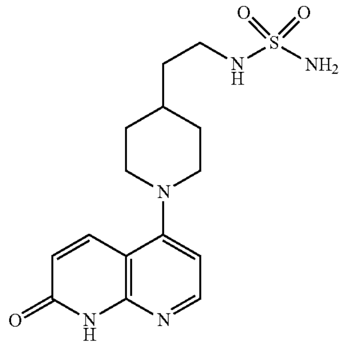 [SMILES: NS(=O)(=O)NCCC1CCN(c2ccnc3[nH]c(=O)ccc23)CC1]

$^1$H NMR (400 MHz, DMSO-d6) δ 8.27 (d, J=6.3 Hz, 1H), 8.01 (s, 1H), 6.90 (d, J=6.4 Hz, 1H), 6.70-6.40 (m, 4H), 3.78-3.69 (m, 2H), 3.15-3.08 (m, 2H), 2.96 (t, J=7.2 Hz, 2H), 1.83 (d, J=12.3 Hz, 2H), 1.76-1.64 (m, 1H), 1.50 (q, J=7.0 Hz, 2H), 1.45-1.32 (m, 2H).

[Example 126]: 8-(7-oxo-7,8-dihydro-1,8-naphthyridin-4-yl)-2,8-diazaspiro[4,5]decane-2-sulfamide

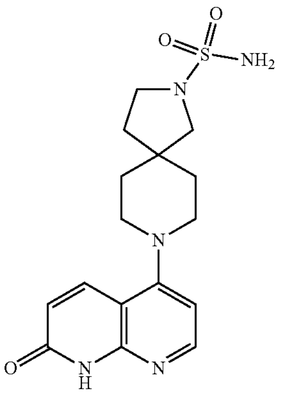 [SMILES: NS(=O)(=O)N1CCC2(CCN(c3ccnc4[nH]c(=O)ccc34)CC2)C1]

$^1$H NMR (400 MHz, Methanol-d4) δ 8.28 (d, J=9.5 Hz, 1H), 8.20 (d, J=7.2 Hz, 1H), 7.04 (d, J=7.2 Hz, 1H), 6.87 (d, J=9.5 Hz, 1H), 3.88-3.71 (m, 4H), 3.41-3.37 (m, 3H), 2.01-1.82 (m, 7H).

[Example 127]: 8-(7-oxo-7,8-dihydro-1,8-naphthyridin-4-yl)-2,8-diazaspiro[4,5]decane-2-sulfamide

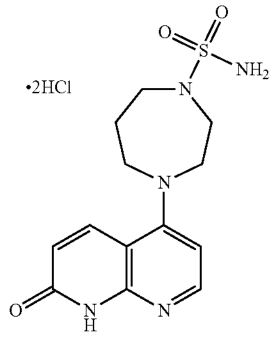 [SMILES: NS(=O)(=O)N1CCCN(c2ccnc3[nH]c(=O)ccc23)CC1]

$^1$H NMR (400 MHz, DMSO-d6) δ 8.33 (d, J=8.0 Hz, 1H), 8.21 (d, J=7.2 Hz, 1H), 6.91 (d, J=7.3 Hz, 1H), 6.93-6.76 (m, 3H), 6.72 (d, J=9.6 Hz, 1H), 3.93 (s, 2H), 3.54 (s, 2H), 3.33 (s, 2H), 3.30-3.26 (m, 2H), 2.04 (s, 2H).

[Example 128]: N-((1-(8-methyl-7-oxo-7,8-dihydro-1,8-naphthyridin-4-yl)piperidin-4-yl)methyl)sulfamide

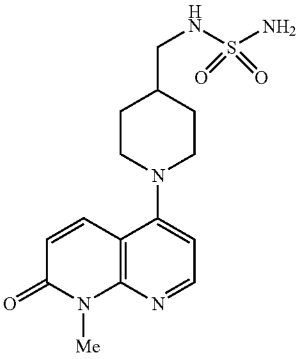 [SMILES: Cn1c(=O)ccc2c(N3CCC(CNS(N)(=O)=O)CC3)ccnc21]

$^1$H NMR (400 MHz, MeOD-d4) δ 8.13 (d, J=7.2 Hz, 1H), 7.98 (d, J=9.9 Hz, 1H), 7.10 (d, J=7.1 Hz, 1H), 6.68 (d, J=9.9 Hz, 1H), 4.02 (d, J=13.3 Hz, 2H), 3.75 (s, 3H), 3.40 (d, J=12.8 Hz, 2H), 3.02 (d, J=6.3 Hz, 2H), 2.08-1.92 (m, 3H), 1.62-1.43 (m, 2H).

Preparation Example 4

Preparation Example 4 includes a process of preparing product 3, product 4, product 7, or product 8.

Preparation Example 4

[Reaction Scheme 4]

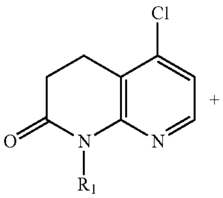

1

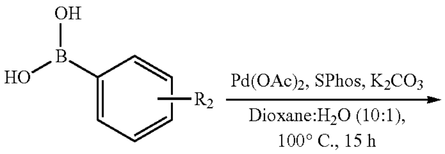

2

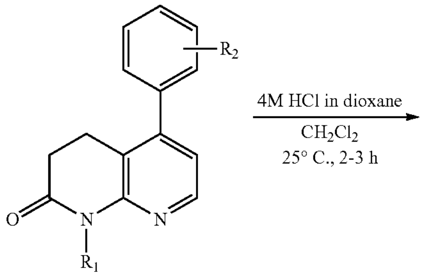

3

-continued

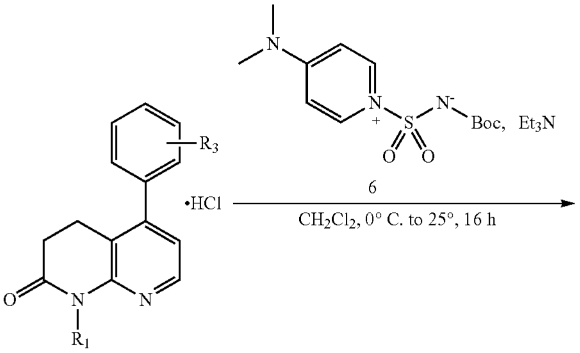

4

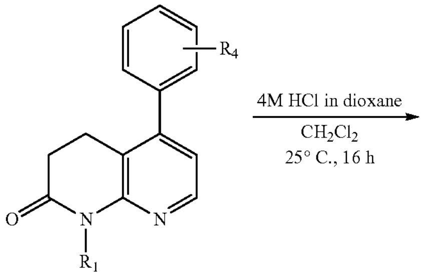

7

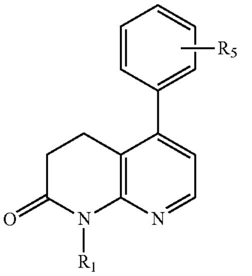

8

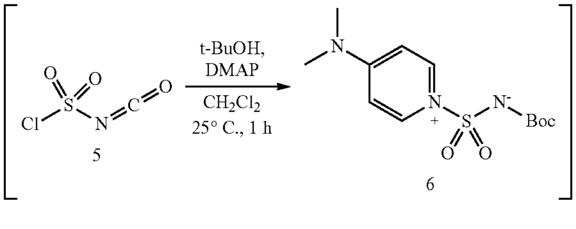

Step 1: 1 (1.0 equiv.), palladium(II) acetate (0.050 equiv.), 2-dicyclohexylphosphino-2',6'-dimethoxybiphenyl (0.10 equiv.), 2 (1.3 equiv.) and potassium carbonate (3.0 equiv.) were dissolved in 1,4-dioxane (0.090 M) and water (0.90 M) in a round bottom flask and refluxed under nitrogen for 16 hours. After the reaction was completed, the mixture was filtered through celite, poured into water, and extracted with dichloromethane. The organic layer was dried over anhydrous magnesium sulfate and concentrated under reduced pressure. The resulting residue was purified by column chromatography (1:20 MeOH:CH$_2$Cl$_2$) to obtain 3 (40-60% yield).

[Example 129]: tert-butyl(3-(7-oxo-5,6,7,8-tetrahydro-1,8-naphthyridin-4-yl)benzyl)carbamate

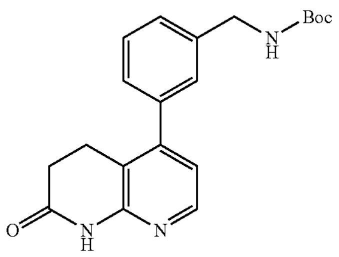 [SMILES: CC(C)(C)OC(=O)NCc1cccc(-c2ccnc3c2CCC(=O)N3)c1]

$^1$H NMR (400 MHz, MeOD-d4) δ 8.15 (d, J=5.2 Hz, 1H), 7.45 (t, J=7.6 Hz, 1H), 7.36 (d, J=7.8 Hz, 1H), 7.32-7.24 (m, 2H), 6.99 (d, J=5.1 Hz, 1H), 4.29 (s, 2H), 2.94 (t, J=7.6 Hz, 2H), 2.54 (t, J=7.6 Hz, 2H), 1.45 (s, 9H).

Step 2: 3 (1.0 equiv.) was dissolved in dichloromethane (0.040 M) in a round bottom flask. Then, a hydrochloride solution (4.0 M in 1,4-dioxane, 0.2 M) was added thereto, followed by stirring at room temperature for 4 hours. After the reaction was completed, the reaction mixture was concentrated under reduced pressure, and then the resulting residue was washed with diethyl ether, filtered and dried to obtain 4 (60-80% yield).

[Example 130]: tert-butyl(4-(7-oxo-5,6,7,8-tetrahydro-1,8-naphthyridin-4-yl)benzyl)carbamate

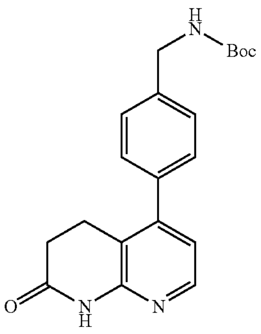

$^1$H NMR (400 MHz, DMSO-d6) δ 10.48 (s, 1H), 8.14 (d, J=5.2 Hz, 1H), 7.45 (t, J=6.4 Hz, 1H), 7.36 (d, J=3.9 Hz, 4H), 6.93 (d, J=5.2 Hz, 1H), 4.18 (d, J=6.2 Hz, 2H), 2.84 (t, J=7.6 Hz, 2H), 2.42 (t, J=7.5 Hz, 2H), 1.40 (s, 9H).

[Example 131]: 5-(3-(aminophenyl)-3,4-dihydro-1,8-naphthyridin-2(1H)-one hydrochloride

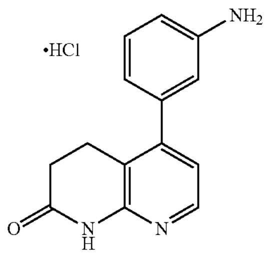 [SMILES: Nc1cccc(-c2ccnc3c2CCC(=O)N3)c1 ; Cl]

$^1$H NMR (400 MHz, MeOD-d4) δ 8.29 (d, J=6.0 Hz, 1H), 7.75 (t, J=7.9 Hz, 1H), 7.64-7.53 (m, 3H), 7.31 (d, J=6.0 Hz, 1H), 3.06 (dd, J=8.5, 6.6 Hz, 2H), 2.68 (dd, J=8.5, 6.6 Hz, 2H).

[Example 132]: 5-(3-(aminomethyl)phenyl)-3,4-dihydro-1,8-naphthyridin-2(1H)-one hydrochloride

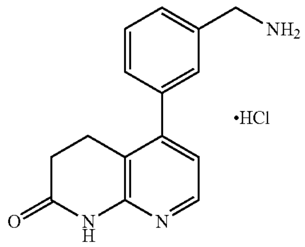 [SMILES: NCc1cccc(-c2ccnc3c2CCC(=O)N3)c1 ; Cl]

$^1$H NMR (400 MHz, MeOD-d4) δ 8.25 (d, J=5.8 Hz, 1H), 7.68-7.60 (m, 2H), 7.58 (s, 1H), 7.56-7.52 (m, 1H), 7.25 (d, J=5.8 Hz, 1H), 4.23 (s, 2H), 3.05 (t, J=7.6 Hz, 2H), 2.65 (t, J=7.6 Hz, 2H).

[Example 133]: 5-(4-(aminomethyl)phenyl)-3,4-dihydro-1,8-naphthyridin-2(1H)-one hydrochloride

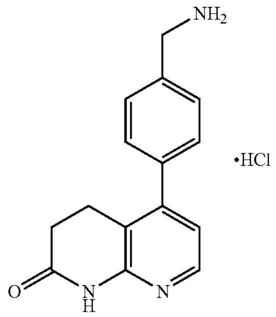 [SMILES: NCc1ccc(-c2ccnc3c2CCC(=O)N3)cc1 ; Cl]

$^1$H NMR (400 MHz, MeOD-d4) δ 8.17 (d, J=5.2 Hz, 1H), 7.57 (d, J=8.0 Hz, 2H), 7.48 (d, J=8.1 Hz, 2H), 6.98 (d, J=5.2 Hz, 1H), 4.15 (s, 2H), 2.93 (t, J=7.6 Hz, 2H), 2.55 (t, J=7.6 Hz, 2H).

[Example 134]: 5-(4-(2-aminopropan-2-yl)phenyl)-3,4-dihydro-1,8-naphthyridin-2(1H)-one hydrochloride

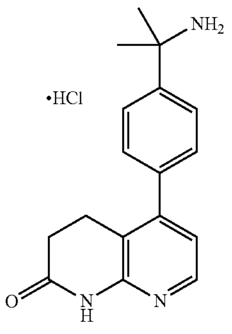 [SMILES: CC(C)(N)c1ccc(-c2ccnc3c2CCC(=O)N3)cc1 ; Cl]

$^1H$ NMR (400 MHz, MeOD-d4) δ 8.27 (d, J=6.0 Hz, 1H), 7.73 (d, J=8.6 Hz, 2H), 7.62 (d, J=8.6 Hz, 2H), 7.32 (d, J=6.0 Hz, 1H), 3.08 (dd, J=8.5, 6.6 Hz, 2H), 2.68 (dd, J=8.5, 6.6 Hz, 2H), 1.80 (s, 6H).

[Example 135]: 5-(1,2,3,4-tetrahydroisoquinolin-7-yl)-3,4-dihydro-1,8-naphthyridin-2(1H)-one hydrochloride

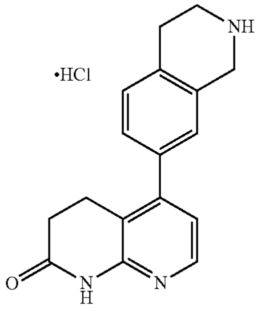 [SMILES: O=C1CCc2c(-c3ccc4c(c3)CNCC4)ccnc2N1 ; Cl]

$^1H$ NMR (400 MHz, DMSO-d6) δ 10.65 (s, 1H), 9.68 (s, 2H), 8.19 (d, J=5.2 Hz, 1H), 7.39-7.28 (m, 3H), 6.96 (d, J=5.3 Hz, 1H), 4.30 (s, 2H), 3.38 (s, 2H), 3.08 (t, J=6.1 Hz, 2H), 2.86 (t, J=7.5 Hz, 2H), 2.45 (t, J=7.5 Hz, 2H).

[Preparation of sulfamide 6]: A solution of tert-butanol (1.0 equiv.) in anhydrous dichloromethane (1.4 M) was added to a round bottom flask and 5 (1.0 equiv.) was slowly added dropwise thereto. Then, N,N-dimethylpyridin-4-amine (2.0 equiv.) was added thereto. The solution was stirred at room temperature for 1 hour. After the reaction was complete, the reaction product was washed several times with water. The organic layer was dried over anhydrous sodium sulfate and concentrated in vacuo. The obtained colorless powder 6 (80% yield) was used as a reactant without further purification.

Step 3: A solution of triethylamine (2.5 equiv.) in dichloromethane (0.1 M) was added to a round bottom flask. Then, 4 (1.0 equiv.) and 6 (1.1 equiv.) were added thereto, followed by stirring at room temperature for one day. After the reaction was completed, the reaction product was concentrated under reduced pressure and dried, and the obtained residue was extracted using dichloromethane and water. The resulting residue was purified through column chromatography (1:20 MeOH:$CH_2Cl_2$) to obtain 7 (30-60% yield).

[Example 136]: tert-butyl(N-(3-(7-oxo-5,6,7,8-tetrahydro-1,8-naphthyridin-4-yl)benzyl)sulfamoyl)carbamate

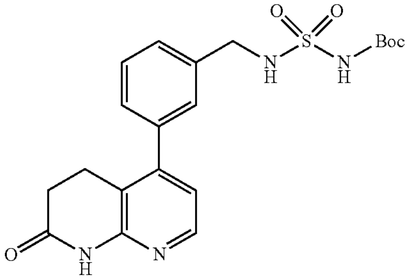 [SMILES: CC(C)(C)OC(=O)NS(=O)(=O)NCc1cccc(-c2ccnc3c2CCC(=O)N3)c1]

$^1H$ NMR (400 MHz, MeOD-d4) δ 8.15 (d, J=5.2 Hz, 1H), 7.48-7.42 (m, 3H), 7.31-7.27 (m, 1H), 7.02 (d, J=5.2 Hz, 1H), 4.17 (s, 2H), 2.97 (t, J=7.5 Hz, 2H), 2.55 (t, J=7.5 Hz, 2H), 1.41 (s, 9H).

[Example 137]: tert-butyl(N-(4-(7-oxo-5,6,7,8-tetrahydro-1,8-naphthyridin-4-yl)benzyl)sulfamoyl)carbamate

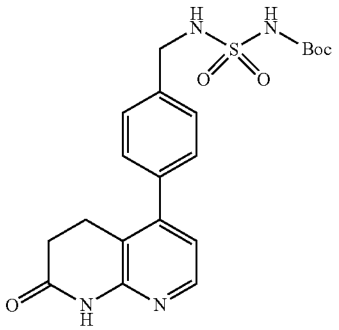

$^1H$ NMR (400 MHz, MeOD-d4) δ 8.15 (d, J=5.2 Hz, 1H), 7.51 (d, J=8.1 Hz, 2H), 7.36 (d, J=8.1 Hz, 2H), 6.99 (d, J=5.1 Hz, 1H), 4.21 (s, 2H), 2.96 (t, J=7.5 Hz, 2H), 2.54 (t, J=7.5 Hz, 2H), 1.45 (s, 9H).

[Example 138]: tert-butyl((7-(7-oxo-5,6,7,8-tetrahydro-1,8-naphthyridin-4-yl)-3,4-diisoquinoline-2(1H)-yl)sulfonyl)carbamate

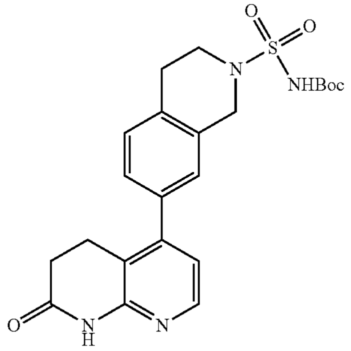 [SMILES: CC(C)(C)OC(=O)NS(=O)(=O)N1CCc2ccc(-c3ccnc4c3CCC(=O)N4)cc2C1]

$^1H$ NMR (400 MHz, DMSO-d6) δ 11.15 (s, 1H), 10.52 (s, 1H), 8.15 (d, J=5.1 Hz, 1H), 7.31-7.26 (m, 2H), 7.23 (d, J=7.7 Hz, 1H), 6.92 (d, J=5.2 Hz, 1H), 4.53 (s, 2H), 3.57 (t, J=5.9 Hz, 2H), 2.94 (t, J=5.8 Hz, 2H), 2.85 (d, J=7.9 Hz, 2H), 2.43 (t, J=7.5 Hz, 2H), 1.33 (s, 9H).

Step 4: 7 (1.0 equiv.) was dissolved in dichloromethane (0.04 M) in a round bottom flask. Then, a hydrochloride solution (4.0 M in 1,4-dioxane, 0.2M) was added thereto, followed by stirring at room temperature for 16 hours. After the reaction was completed, the reaction product was concentrated under reduced pressure and the resulting residue was washed with diethyl ether, filtered and dried to obtain 8 (40-80% yield).

[Example 139]: N-(3-(7-oxo-5,6,7,8-tetrahydro-1,8-naphthyridin-4-yl)phenyl)sulfamide

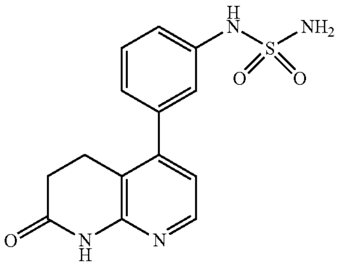 [SMILES: NS(=O)(=O)Nc1cccc(-c2ccnc3c2CCC(=O)N3)c1]

$^1$H NMR (400 MHz, MeOD-d4) δ 8.23 (d, J=6.0 Hz, 1H), 7.48 (t, J=7.9 Hz, 1H), 7.36-7.30 (m, 3H), 7.15 (dt, J=7.9, 1.2 Hz, 1H), 3.11 (t, J=8.4, 6.6 Hz, 2H), 2.66 (dd, J=8.4, 6.6 Hz, 2H).

[Example 140]: N-(3-(7-oxo-5,6,7,8-tetrahydro-1,8-naphthyridin-4-yl)benzyl)sulfamide

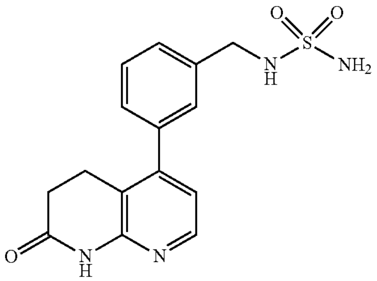 [SMILES: NS(=O)(=O)NCc1cccc(-c2ccnc3c2CCC(=O)N3)c1]

$^1$H NMR (400 MHz, MeOD-d4) δ 8.27 (d, J=6.2 Hz, 1H), 7.60-7.53 (m, 3H), 7.41 (d, J=6.3 Hz, 2H), 4.31 (s, 2H), 3.14 (t, J=7.5 Hz, 2H), 2.70 (t, J=7.5 Hz, 2H).

[Example 141]: N-(4-(7-oxo-5,6,7,8-tetrahydro-1,8-naphthyridin-4-yl)benzyl)sulfamide

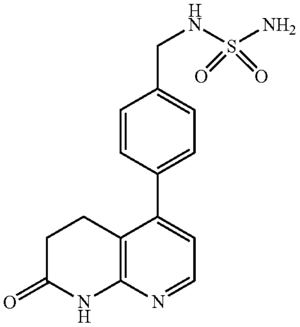

$^1$H NMR (400 MHz, DMSO-d6) δ 10.48 (s, 1H), 8.14 (d, J=5.1 Hz, 1H), 7.46 (d, J=8.0 Hz, 2H), 7.37 (d, J=8.0 Hz, 2H), 6.93 (d, J=5.2 Hz, 1H), 4.13 (s, 2H), 2.84 (t, J=7.6 Hz, 2H), 2.42 (t, J=7.6 Hz, 2H).

[Example 142]: N-(2-fluoro-4-(7-oxo-5,6,7,8-tetrahydro-1,8-naphthyridin-4-yl)benzyl)sulfamide

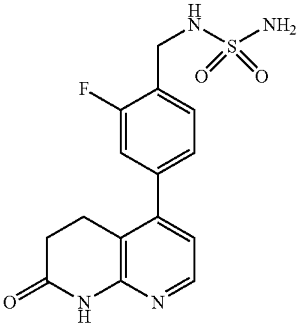

$^1$H NMR (400 MHz, MeOD-d4) δ 8.26 (d, J=6.1 Hz, 1H), 7.73 (t, J=7.7 Hz, 1H), 7.35 (d, J=6.1 Hz, 1H), 7.32-7.25 (m, 2H), 4.36 (s, 2H), 3.10 (dd, J=8.4, 6.6 Hz, 2H), 2.68 (t, J=8.4, 6.6 Hz, 2H).

[Example 143]: 5-(7-oxo-5,6,7,8-tetrahydro-1,8-naphthyridin-4-yl)isoindoline-2-sulfamide hydrochloride

•HCl

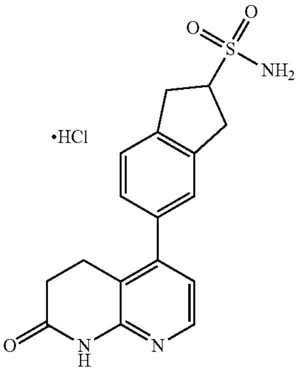 [SMILES: NS(=O)(=O)C1Cc2ccc(-c3ccnc4c3CCC(=O)N4)cc2C1 ; Cl]

LC-MS (ESI) calcd for $C_{16}H_{16}N_4O_3S$ $[M+H]^+$ 344.09, found m/z 345.35.

[Example 144]: (7-(7-oxo-5,6,7,8-tetrahydro-1,8-naphthyridin-4-yl)amino)-3,4-dihydroisoquinoline-2(1H)-sulfamide hydrochloride

•2HCl

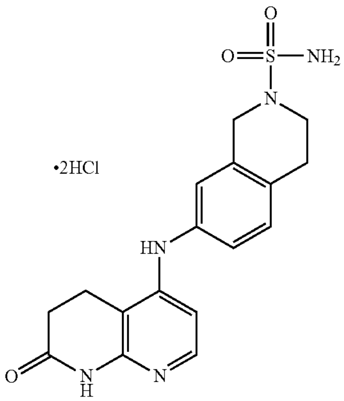 [SMILES: NS(=O)(=O)N1CCc2ccc(Nc3ccnc4c3CCC(=O)N4)cc2C1 ; "·2HCl"]

$^1$H NMR (400 MHz, DMSO-d6) δ 10.92 (s, 1H), 9.26 (s, 1H), 7.85 (s, 1H), 7.31-7.21 (m, 1H), 7.08 (d, J=17.5 Hz, 2H), 6.96 (d, J=7.4 Hz, 2H), 6.61 (d, J=6.8 Hz, 1H), 4.22 (s, 2H), 3.29 (s, 1H), 2.93 (brs, 4H), 2.67 (t, J=7.4 Hz, 2H).

[Example 145]: (7-(7-oxo-5,6,7,8-tetrahydro-1,8-naphthyridin-4-yl)-3,4-dihydroisoguinolin-2(1H)-yl) sulfamide hydrochloride

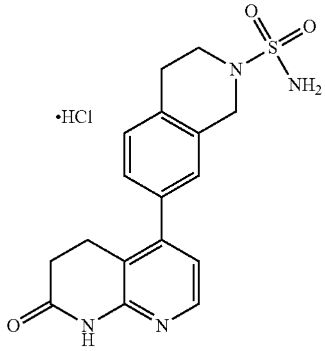 [SMILES: NS(=O)(=O)N1CCc2ccc(-c3ccnc4c3CCC(=O)N4)cc2C1 ; Cl]

$^1$H NMR (400 MHz, DMSO-d6) δ 10.61 (s, 1H), 8.17 (d, J=5.2 Hz, 1H), 7.30 (d, J=8.2 Hz, 12H), 7.24 (d, J=7.2 Hz, 2H), 6.99 (d, J=5.2 Hz, 2H), 4.27-4.22 (m, 2H), 3.31 (t, J=5.9 Hz, 2H), 2.97 (t, J=5.8 Hz, 2H), 2.88 (t, J=7.5 Hz, 2H), 2.44 (t, J=7.5 Hz, 2H).

[Reaction Scheme 4-1]

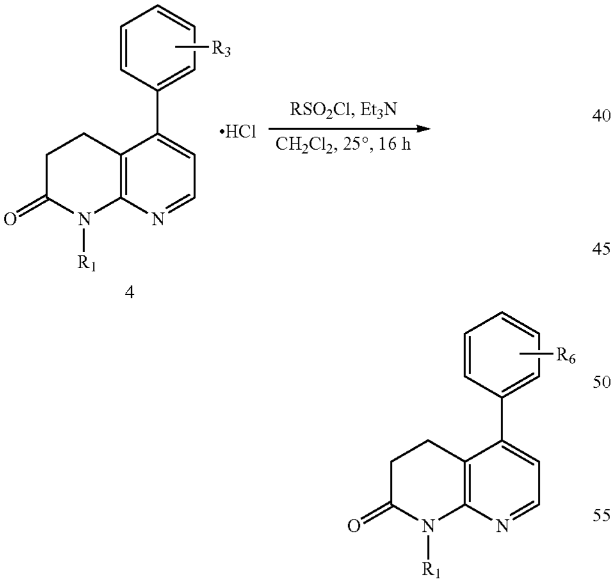

4

9

4 (1.0 equiv.) and $RSO_2Cl$ (1.1 equiv.) were dissolved in dichloromethane (0.08 M) in a round bottom flask and then triethylamine (4.5 equiv.) was added thereto, followed by stirring at room temperature for 16 hours. After the reaction was completed, water was poured into the mixture, followed by extraction with dichloromethane. The organic layer was dried over anhydrous magnesium sulfate and concentrated under reduced pressure. The resulting residue was purified by column chromatography (1:20 $MeOH:CH_2Cl_2$) to obtain 9 (30-50% yield).

[Example 146]: N-(3-(7-oxo-5,6,7,8-tetrahydro-1,8-naphthyridin-4-yl)benzyl)methanesulfonamide

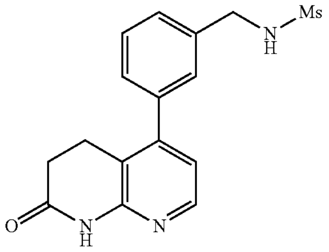 [SMILES: CS(=O)(=O)NCc1cccc(-c2ccnc3c2CCC(=O)N3)c1]

$^1$H NMR (400 MHz, MeOD-d4) δ 8.16 (d, J=5.1 Hz, 1H), 7.52-7.45 (m, 2H), 7.42 (s, 1H), 7.33 (d, J=6.9 Hz, 1H), 7.00 (d, J=5.2 Hz, 1H), 4.33 (s, 2H), 2.95 (t, J=7.6 Hz, 2H), 2.91 (s, 3H), 2.55 (t, J=7.6 Hz, 2H).

[Example 147]: 4-methyl-N-(3-(7-oxo-5,6,7,8-tetrahydro-1,8-naphthyridin-4-yl)benzyl)benzenesulfonamide

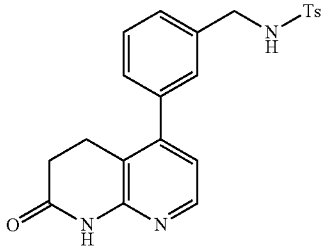 [SMILES: Cc1ccc(S(=O)(=O)NCc2cccc(-c3ccnc4c3CCC(=O)N4)c2)cc1]

$^1$H NMR (400 MHz, MeOD-d4) δ 8.15 (d, J=5.2 Hz, 1H), 7.71 (d, J=8.2 Hz, 2H), 7.39 (t, J=7.6 Hz, 1H), 7.32 (d, J=7.8 Hz, 3H), 7.25 (d, J=7.6 Hz, 1H), 7.17 (s, 1H), 6.90 (d, J=5.2 Hz, 1H), 4.15 (s, 2H), 2.86 (t, J=7.5 Hz, 2H), 2.53 (t, J=7.5 Hz, 2H), 2.39 (s, 3H).

[Example 148]: N-(3-(7-oxo-5,6,7,8-tetrahydro-1,8-naphthyridin-4-yl)benzyl)thiophene-2-sulfonamide

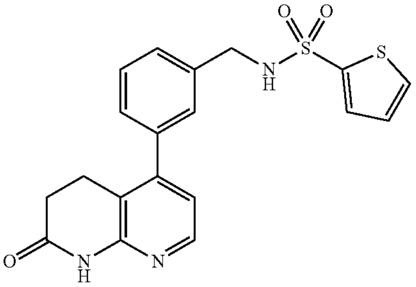 [SMILES: O=C1CCc2c(-c3cccc(CNS(=O)(=O)c4cccs4)c3)ccnc2N1]

$^1$H NMR (400 MHz, MeOD-d4) δ 8.15 (d, J=5.2 Hz, 1H), 7.73 (dd, J=5.0, 1.3 Hz, 1H), 7.56 (dd, J=3.8, 1.3 Hz, 1H), 7.42 (t, J=7.9 Hz, 1H), 7.35 (d, J=7.9 Hz, 1H), 7.30-7.24 (m, 2H), 7.10 (dd, J=5.0, 3.7 Hz, 1H), 6.95 (d, J=5.3 Hz, 1H), 4.23 (s, 2H), 2.90 (t, J=7.6 Hz, 2H), 2.54 (t, J=7.6 Hz, 2H).

Experimental Example

The following experiments were conducted on the Examples 1 to 148 prepared as described above.

Experimental Example 1: ENPP1 Enzyme Assay with cGAMP Substrate

ENPP1 hydrolyzes nucleotides or nucleotide derivatives to produce nucleoside-5'-monophosphate and pyrophosphate. In addition, ENPP1 hydrolyzes 2',3'-cGAMP to produce 5'-adenosine monophosphate (AMP) and 5'-guanosine monophosphate (GMP). AMP produced from the reaction is measured using the AMP-Glo® kit (Promega). The AMP-Glo® kit contains two reagents. The first reagent terminates the AMP-producing enzymatic reaction, removes ATP and converts the produced AMP into ADP. The second reagent converts ADP to ATP which is used to generate luminescence in the luciferase reaction. The amount of luminescence measured is proportional to the amount of AMP produced by ENPP1.

The final reaction mixture contains 50 mM Tris (pH 8.5) buffer, 250 mM NaCl, 0.5 mM $CaCl_2$), 1 μM $ZnCl_2$, 5% glycerol and 1% DMSO. Serially diluted ENPP1 inhibitors (typically in the range of 10 μM to 0.5 nM) were pre-stored with human recombinant ENPP1 enzymes (R & D systems) at 3 ng/reaction and room temperature (RT) for 5 to 10 minutes. The reaction was initiated by addition of cGAMP (at a final concentration of 5 μM) and reacted at 37° C. for 90 minutes. At the end of the reaction, 10 μl of the AMP-Glo first reagent was added to stop the reaction and the result was stored at room temperature for 1 hour. After storage, 20 μl of an AMP detection solution (a mixture of AMP-Glo II reagent and Kinase-Glo at a ratio of 1:100) was added and stored at room temperature for 1 hour. Luminescence signals were measured using a Victor® plate reader (Perkin Elmer). The maximal activity control (containing enzymes and substrates in the presence of 1% DMSO; MAX) and the minimal activity control (containing substrates and 1% DMSO; MIN) were evaluated simultaneously. In each experiment, serially diluted reference ENPP1 inhibitors were tested as well. $IC_{50}$, indicating % residual activity versus compound concentration was determined by fitting inhibition curves using the 3-parameter analysis of GraphPad Prism® software. Serially diluted samples of one compound were tested two or more times and an average $IC_{50}$ of each compound was calculated.

The experimental results are shown in Tables 1 and 2 below.

TABLE 1

| Example | Enzymatic activity |
|---|---|
| 1 | B |
| 2 | B |
| 3 | B |
| 7 | A |
| 8 | C |
| 10 | A |
| 11 | A |
| 12 | A |
| 13 | A |
| 14 | A |
| 15 | A |

TABLE 1-continued

| Example | Enzymatic activity |
|---|---|
| 16 | B |
| 17 | B |
| 18 | A |
| 20 | B |
| 21 | C |
| 22 | B |
| 23 | B |
| 24 | C |
| 25 | B |
| 26 | A |
| 27 | B |
| 28 | A |
| 29 | B |
| 32 | A |
| 35 | A |
| 36 | A |
| 37 | A |
| 38 | A |
| 39 | B |
| 40 | A |
| 42 | A |
| 43 | A |
| 44 | A |
| 45 | A |
| 46 | A |
| 47 | A |
| 48 | A |
| 50 | A |
| 51 | A |
| 52 | A |
| 53 | A |
| 54 | A |
| 55 | A |
| 56 | A |
| 57 | C |
| 58 | A |
| 59 | A |
| 60 | B |
| 61 | A |
| 64 | A |
| 65 | A |
| 66 | A |
| 67 | A |
| 70 | A |
| 71 | B |
| 74 | B |
| 75 | A |
| 77 | A |
| 78 | A |
| 79 | B |
| 81 | A |
| 82 | A |
| 84 | A |
| 85 | A |
| 86 | B |
| 87 | C |
| 88 | A |
| 89 | A |
| 90 | A |
| 91 | A |
| 92 | A |
| 93 | A |
| 94 | A |
| 95 | A |
| 97 | A |
| 98 | B |
| 99 | B |
| 100 | B |
| 101 | A |
| 102 | A |
| 103 | B |
| 104 | B |
| 106 | A |
| 107 | A |
| 108 | C |
| 113 | A |
| 114 | A |
| 115 | A |

TABLE 1-continued

| Example | Enzymatic activity |
|---|---|
| 117 | B |
| 118 | C |
| 123 | A |
| 124 | A |
| 125 | A |
| 126 | A |
| 127 | B |
| 128 | A |
| 131 | B |
| 132 | C |
| 133 | A |
| 134 | A |
| 135 | C |
| 138 | B |
| 139 | A |
| 140 | A |
| 141 | A |
| 142 | A |
| 143 | A |
| 144 | A |
| 145 | A |
| 146 | B |
| 147 | A |

TABLE 2

| Enzymatic activity | A | B | C | NA |
|---|---|---|---|---|
| $IC_{50}$ (μM) | activity <1 μM | 1 μM < activity <10 μM | activity >10 μM | No activity |

Experimental Example 2

The following experiments were conducted on the Examples prepared as described above.

Experimental Example 2: HCT116-Dual Cell Luciferase Assay

HCT116-Dual™ cells express genes encoding luciferase secreted under the control of the interferon-stimulated gene 54 (ISG54) promoter along with five interferon-stimulated response elements. The HCT116-Dual™ cell line was used to measure and monitor the activity of interferon regulatory factor 3 (IRF3), which induces production of type I interferon and relates to downstream signaling, and Lucia secreted in the culture medium was used to generate luminescence in a luciferase reaction.

HCT116-Dual™ cells were cultured at $2\times10^4$ cells/well (93.4 μL) in a 96-well plate for one day in a DMEM medium containing 10% FBS and 25 mM HEPES (pH 7.2-7.5). The cells were treated with 3.3 μL of ENPP1 inhibitor (usually 10 μM) and then 3.3 μL of cGAMP (10 μM) to set the final volume to 100 μL (The final fraction of DMSO was 0.1%). The cells treated with ENPP1 inhibitor and cGAMP were cultured at 37° C. for 48 hours and 50 μL of Quanti-Luc reaction solution was added to 20 μL of cell culture medium to measure luciferase activity. The increase in interferon regulatory factor 3 (IRF3) by the compound compared to cGAMP was determined as fold.

The experimental results are shown in Tables 3 and 4 below.

TABLE 3

| Example | Cellular activity |
|---|---|
| 8 | B |
| 10 | B |
| 11 | A |
| 12 | A |
| 13 | A |
| 14 | B |
| 15 | B |
| 20 | A |
| 21 | B |
| 22 | B |
| 23 | B |
| 24 | B |
| 25 | A |
| 28 | B |
| 35 | B |
| 36 | B |
| 37 | B |
| 38 | B |
| 41 | B |
| 42 | A |
| 43 | B |
| 45 | B |
| 52 | B |
| 53 | B |
| 54 | B |
| 55 | B |
| 56 | B |
| 58 | B |
| 61 | B |
| 64 | B |
| 65 | B |
| 79 | B |
| 93 | B |
| 94 | B |
| 97 | B |
| 102 | A |
| 140 | B |
| 142 | B |
| 143 | B |
| 145 | B |

TABLE 4

| Cellular activity | A | B |
|---|---|---|
| Fold | >2 | 1< Fold <2 |

FORMULATION EXAMPLE

Meanwhile, the novel compound represented by Formula 1 according to the present invention may be formulated in various forms according to purpose. Examples of some formulation methods for incorporating the compound represented by Formula 1 according to the present invention as an active ingredient are as follows, but the present invention is not limited thereto.

Formulation Example 1: Tablet (Direct Pressurization)

5.0 mg of the active ingredient was sieved, 14.1 mg of lactose, 0.8 mg of crospovidone USNF, and 0.1 mg of magnesium stearate were mixed therewith, and the mixture was compressed into tablets.

Formulation Example 2: Tablet (Vet Granulation)

5.0 mg of the active ingredient was sieved and mixed with 16.0 mg of lactose and 4.0 mg of starch. 0.3 mg of Polysorbate 80 was dissolved in pure water, and an appropriate amount of the resulting solution was added to the resulting mixture, followed by granulation. The granules were dried, sieved, and mixed with 2.7 mg of colloidal silicon dioxide and 2.0 mg of magnesium stearate. The granules were compressed into tablets.

Formulation Example 3: Powders and Capsules 5.0 mg of the active ingredient was sieved and then mixed with 14.8 mg of lactose, 10.0 mg of polyvinylpyrrolidone, and 0.2 mg of magnesium stearate. Hard No. 5 gelatin capsules were filled with the resulting mixture using an appropriate device.

Formulation Example 4: Injection

Injections were prepared by incorporating 100 mg of the active ingredient as well as 180 mg of mannitol, 26 mg of $Na_2HPO_4 \cdot 12H_2O$, and 2,974 mg of distilled water.

Although embodiments of the present invention have been described above, it will be obvious to those skilled in the art that the present invention can be implemented in other specific embodiments without changing the technical concepts or essential features of the present invention. Therefore, it should be construed that the aforementioned embodiments are illustrative and not restrictive in all respects.

The invention claimed is:

1. A compound selected from a naphthyridinone derivative compound represented by the following Formula 1, a pharmaceutically acceptable salt thereof, a hydrate thereof, or a stereoisomer thereof:

[Formula 1]

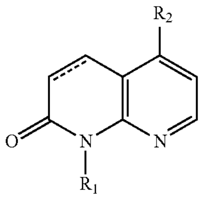

wherein $R_1$ is hydrogen, or a $C_1$-$C_6$ alkyl group;

$R_2$ is —Z-A;

Z is present or absent, wherein when Z is present, Z is —NH—, or —$(NC_nH_{2n+1})$—;

n is an integer from 1 to 6;

A is selected from the group consisting of:

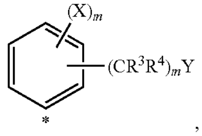
,
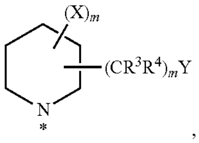
,
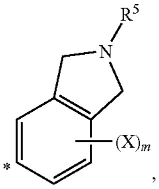
,

-continued

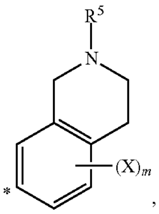
,
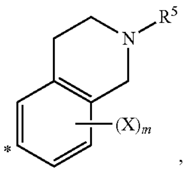
,
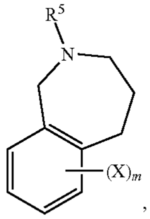
,
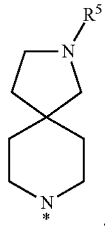
, and
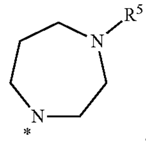
;

X is halogen;

m is an integer from 0 to 3;

$R_3$ and $R_4$ are each independently hydrogen, or branched- or straight-chain $C_1$-$C_6$ alkyl;

$R_5$ is hydrogen, $S(O)_2NH_2$, or $S(O)_2NH$-Boc;

Y is $NR^6R^7$ or $P(O)R^8R^9$;

$R^6$ is hydrogen, branched- or straight-chain $C_1$-$C_6$ alkyl, or $C_3$-$C_6$ cycloalkyl;

$R^7$ is hydrogen, Boc, branched- or straight-chain $C_1$-$C_6$ alkyl, $C_3$-$C_6$ cycloalkyl, $C_5$-$C_6$ aryl, $C_5$-$C_6$ heteroaryl, $S(O)_2NH_2$, $S(O)_2NH$-Boc, $S(O)_2$(branched- or straight-chain $C_1$-$C_6$ alkyl), $S(O)_2(C_3$-$C_6$ cycloalkyl), $S(O)_2(C_5$-$C_6$ aryl), or $S(O)_2(C_5$-$C_6$ heteroaryl), wherein said cycloalkyl, aryl, or heteroaryl is optionally substituted by branched- or straight-chain $C_1$-$C_6$ alkyl; and $R^8$ and $R^9$ are each independently hydroxy or $C_1$-$C_6$ alkyloxy.

2. The compound according to claim 1, wherein $R_1$ is hydrogen or a $C_1$-$C_5$ alkyl group.

3. The compound according to claim 1, wherein $R_1$ is hydrogen or a $C_1$-$C_3$ alkyl group.

4. The compound according to claim 1, wherein the pharmaceutically acceptable salt is a salt of an inorganic or organic acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

5. A pharmaceutical composition comprising the compound according to claim 1 as an active ingredient.

6. An ENPP 1 inhibitor comprising the compound according to claim 1 as an active ingredient.

7. A STING pathway activator comprising the compound according to claim 1 as an active ingredient.

* * * * *